US009957479B2

(12) United States Patent
Wutz et al.

(10) Patent No.: US 9,957,479 B2
(45) Date of Patent: May 1, 2018

(54) MAMMALIAN HAPLOID EMBRYONIC STEM CELLS

(76) Inventors: Anton Wutz, Cambridge (GB); Martin Leeb, Cambridge (GB)

( * ) Notice: Subject to any disclaimer, the term of this patent is extended or adjusted under 35 U.S.C. 154(b) by 0 days. days.

(21) Appl. No.: 14/002,557

(22) PCT Filed: Mar. 2, 2012

(86) PCT No.: PCT/GB2012/050469
§ 371 (c)(1),
(2), (4) Date: Nov. 11, 2013

(87) PCT Pub. No.: WO2012/117254
PCT Pub. Date: Sep. 7, 2012

(65) Prior Publication Data

US 2014/0057801 A1 Feb. 27, 2014

(30) Foreign Application Priority Data

Mar. 2, 2011 (GB) .................................. 1103559.9
Sep. 6, 2011 (GB) .................................. 1115343.4

(51) Int. Cl.
*C12N 5/0735* (2010.01)
*C12N 15/10* (2006.01)

(52) U.S. Cl.
CPC ....... *C12N 5/0606* (2013.01); *C12N 15/1079* (2013.01); *C12N 2501/235* (2013.01); *C12N 2501/727* (2013.01)

(58) Field of Classification Search
CPC .................................................. C12N 5/0606
See application file for complete search history.

(56) References Cited

FOREIGN PATENT DOCUMENTS

| | | | | |
|---|---|---|---|---|
| EP | 2599859 | | 6/2013 | |
| EP | 12708382.2 | | 1/2014 | |
| GB | 1103559.9 | | 3/2011 | |
| GB | 1115343.4 | | 9/2011 | |
| WO | WO2001/30978 | | 5/2001 | |
| WO | WO 2001/32015 | * | 5/2001 | ............... A01N 1/00 |
| WO | WO2001/32015 | | 5/2001 | |
| WO | WO 2001/32015 | * | 10/2001 | ............... A01N 1/00 |

OTHER PUBLICATIONS

Elling et al. (Dec. 2011, Cell Stem Cell, vol. 9, pp. 563-574).*
Davidson et al. (2015, Development, vol. 142, pp. 3090-3099).*
Blakely et al. (2015, Development, vol. 142, pp. 3151-3165).*
Schofield et al. (1992, FEBS, vol. 298(2,3), pp. 154-158).*
Kaufman et al. (1983, J. Embryol. exp. Morph., vol. 73, pp. 249-261).*
Zalm et al. (2009, Reproductive BioMedicine Online, vol. 18(4), pp. 529-535).*
Yi et al. (2010, Nature Protocols, vol. 5(8), pp. 1418-1430) (Year: 2010).*
Elling U et al., "Forward and reverse genetics through derivation of haploid mouse embryonic stem cells," *Cell Stem Cell*, 2011; 9(6):563-574.
Yi et al., "Generation of Medaka Fish Haploid Embryonic Stem Cells", *Science*, 2009; 326( 5951): pp. 430-433.
Freed JJ et al., "Stable haploid cultured cell lines from frog embryos," Proc Natl Acad Sci U S A., 1970;65(2):337-344.
Kaufman MH et al., "Establishment of pluripotential cell lines from haploid mouse embryos," *J Embryol Exp Morphol.*, 1983; 73:249-61.
Sato H et al., "Stable generation of serum- and feeder-free embryonic stem cell-derived mice with full germline-competency by using a GSK3 specific inhibitor," *Genesis*, 2009; 47(6):414-422.
Silva et al., "Promotion of Reprogramming to Ground State Pluripotency by Signal Inhibition," *PLoS Biol.*, 2008; 6: e253.
Otaegui PJ, "Parthenogenetic activation of mouse oocytes by exposure to strontium as a source of cytoplasts for nuclear transfer," *Cloning*, 1999;1(2):111-117.
Skottman H et al., "Culture conditions for human embryonic stem cells," *Reproduction*, 2006; 132(5):691-698.
Leeb M et al., "Derivation of haploid embryonic stem cells from mouse embryos," *Nature*, 2011;479(7371):131-134.
Sritanaudomchai et al., "Discovery of a novel imprinted gene by transcriptional analysis of parthenogenetic embryonic stem cells," *Human Reproduction*, 2010; 25(8):1927-1941.
Lui et al., "Haploidy but not parthenogenetic activation leads to increased incidence of apoptosis in mouse embryos," *Biology of Reproduction*, 2002; 66:204-210.
United Kingdom Intellectual Property Office Search Report for GB1103559.9, completed Aug. 18, 2011.
PCT International Search Report/Written Opinion for PCT/GB2012/050469, completed Jul. 26, 2012.
Wang et al. "Generation and Characterization of Rabbit Embryonic Stem Cells", Stem Cells 2007; 25: 481-489.
Lin et al. A highly homozygous and parthenogenetic human embryonic stem cell line derived from a one-pronuclear oocyte following in vitro fertilization procedure, Cell Research (2007) 12:999-1007.
Huang et al. "Human Trophoblasts Recruited T Lymphocytes and Monocytes into Decidua by Secretion of Chemokine CXCL16 and Interaction with CXCR6 in the First-Trimester Pregnancy", the Journal of Immunology 2008.
Vrana et al. "Nonhuman primate parthenogenetic stem cells", PNAS, vol. 100, Sep. 30, 2003, pp. 11911-11916.
Revazova et al. "Patient-Specific Stem Cell Lines Derived from Human Parthenogenetic Blastocysts" Clone and Stem Cells, vol. 9, No. 3, 2007.
Lin et al. "Multilineage Potential of Homozygous Stem Cells Derived from Metaphase II Oocytes", Stem Cells 2003; 21:152-161.
Tang, F. et al. Tracing the Derivation of Embryonic Stem Cells from the Inner Cell Mass by Single-Cell RNA-Seq Analysis. Cell Stem Cell 6, 468-478 (2010).
Reijo Pera, R. A. et al. Gene expression profiles of human inner cell mass cells and embryonic stem cells. Differentiation 78, 18-23 (2009).

(Continued)

*Primary Examiner* — Thaian N Ton
*Assistant Examiner* — David A. Montanari
(74) *Attorney, Agent, or Firm* — Barnes & Thornburg LLP

(57) ABSTRACT

The invention relates to mammalian haploid embryonic stem cells and methods for the production of such stem cells. The inventions also relates to a cell culture and a cell line of mammalian haploid embryonic stem cells.

6 Claims, 47 Drawing Sheets

(56) References Cited

OTHER PUBLICATIONS

Petropoulos, S., Panula, S. P., Schell, J. P. & Lanner, F. Single-cell RNA sequencing: revealing human pre-implantation development, pluripotency and germline development. J. Intern. Med. 280, 252-264 (2016).
Yan, L. et al. Single-cell RNA-Seq profiling of human preimplantation embryos and embryonic stem cells. Nat. Struct. Mol. Biol. 20, 1131-1139 (2013).
Elling et al. “Forward and reverse genetics through derivation of haploid mouse embryonic stem cells”. Cell Stem Cell (2011) 9: 563-574.
Yang et al. “Generation of genetically modified mice by oocyte injection of androgenetic haploid embryonic stem cells”. Cell (2012) 149: 605-617.
Takahashi et al. “Induction of the G2/M transition stabilizes haploid embryonic stem cells. Development”. (2014) 141: 3842-3847.
Shuai et al. “Durable pluripotency and haploidy in epiblast stem cells derived from haploid embryonic stem cells in vitro”. J Mol Cell Biol . (2015) 7: 326-337.
Zhong et al. “CRISPR-Cas9-Mediated Genetic Screening in Mice with Haploid Embryonic Stem Cells Carrying a Guide RNA Library”. Cell Stem Cell (2015) 17: 221-232.
Zhong et al. “Parthenogenetic haploid embryonic stem cells efficiently support mouse generation by oocyte injection”. Cell Res. (2016) 26: 131-134.
Basu et al., “Purification of Specific Cell Population by fluorescence Activated Cell Sorting (FACS),” Journal of Visualized Experiments, www.jove.com; vol. 41, Jul. 2010, e1546.
Carette et al., “Haploid Genetic Screens in Human Cells Identify Host Factors Used by Pathogens,” Science, vol. 326, Nov. 27, 2009, pp. 1231-1235.
EPO Notice of Opposition of EP2681310, filed Sep. 22, 2017.
Kishigami et al., “Efficient Strontium-Induced activation of Mouse Oocytes in Standard Culture Media by Chelating Calcium,” Journal of Reproduction and Development, vol. 53, No. 6, 2007, pp. 1207-1215.
Kotecki et al., “Isolation and Characterization of a Near-Haploid Human Cell Line,” Experimental Cell Research, No. 252, (1999) pp. 273-280.
Li et al., “Genetic Modification and Screening in Rat Using Haploid Embryonic Stem Cells,” Cell Stem Cell, No. 14, Mar. 6, 2014, pp. 404-414.
Nichols et al., “Validated germline-competent embryonic stem cell lines from nonobese diabetic mice,” Nature Medicine, vol. 15, No. 7, Jul. 2009, pp. 814-819.
Notice of Opposition of EP2681310 from Sonn & Partner, dated Sep. 22, 2017.
Punt-van der Zalm, A., “Toxicity testing of human assisted reproduction devices using the mouse embryo assay,” Reproductive BioMedicine Online, vol. 18, No. 4, (2009), pp. 529-535.
Sagi et al., “Derivation and differentiation of haploid human embryonic stem cells,” Nature, vol. 532, Apr. 7, 2016, pp. 107-125.
Sternberg et al., “Activation of a histone H1 kinase by tyrosine phosphorylation in v-src-transformed fibroblasts,” The EMBO Journal, vol. 12, No. 1, (1993) pp. 323-330.
Szollosi et al., “Inhibition of protein kinases by 6-dimethylaminopurine accelerates the transition to interphase in activated mouse oocytes,” Journal of Cell Science, No. 104, (1993) pp. 861-872.
ThermoFisher Scientific, Ham’s F-10 Nutrient Mix, Catalog No. 11550043, https://www.thermofisher.com/order/catalog/product/11550043.
Wikipedia EGTA (chemical), retrieved from https://en.wikipedia.org/w/index.php?title=EGTA_(chemical&oldid=415311835.
Wikipedia Stem Cell, retrieved from https://en.wikipedia.org/w/index.php?title=Stem_cell&oldid=416090762.
Wikipedia Subculture (biology), retrieved from https://en.wikipedia.org/w/index.php?title=Subculture_(biology) &oldid=417268817.
Wikipedia Subculture (biology), Revised retrieved from https://en.wikipedia.org/w/index/php?title=Subculture_(biology) &oldid=332287779.
Yang et al., “Generation of haploid embryonic stem cells from *Macaca fascicularis* monkey parthenotes,” Cell Research (2013), 23:1187-1200.
Ying et al., “The ground state of embryonic stem cell self-renewal,” Nature, vol. 453, May 22, 2008, pp. 519-524.

* cited by examiner

Strategy for the derivation of haploid mouse embryonic stem (ES) cell lines

FIG. 2A

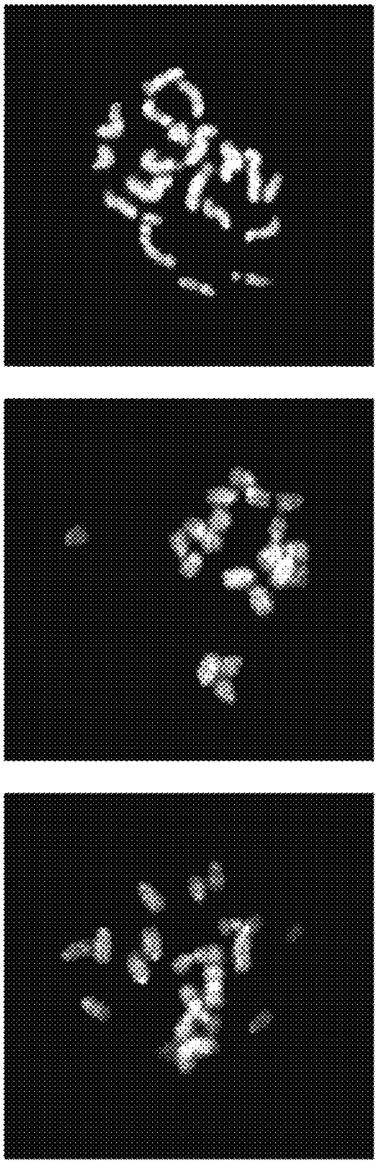

FIG. 2B

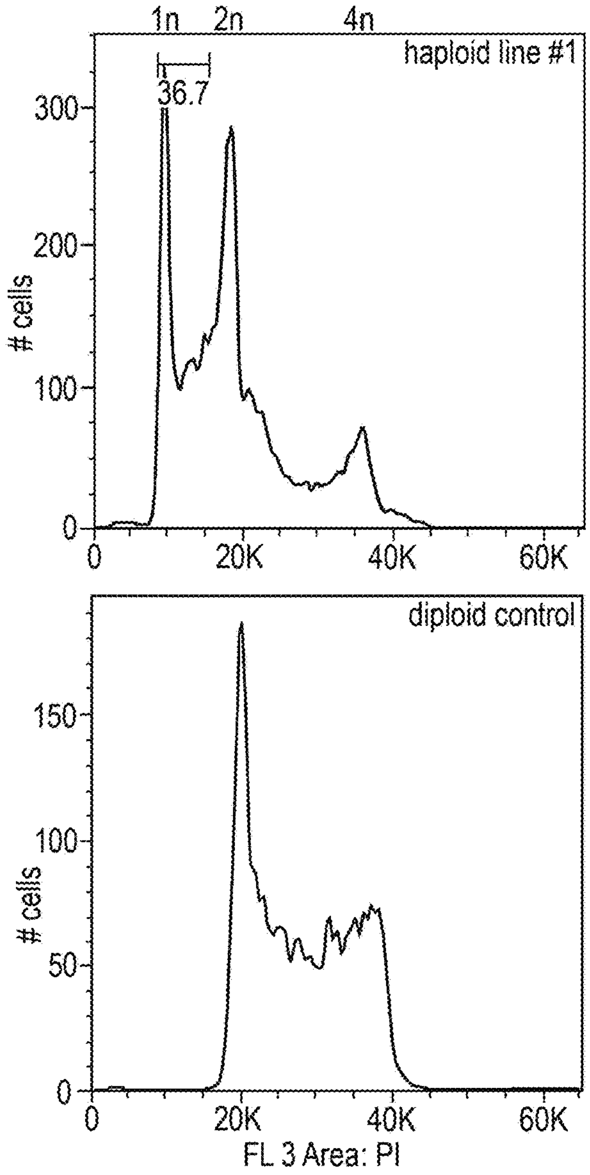

Characterization of a haploid mouse embryonic stem (ES) cell line

A) Three representative pictures of metaphase spreads of a haploid mouse ES cell line showing a haploid set of 20 chromosomes. DNA was stained with DAPI.

B) FACS analysis of fixed ES cells after DNA staining with propidium iodide. Position of haploid (1n), diploid (2n), and tetraploid (4n) DNA content is indicated. The haploid line (upper panel) one shows a predominantly 1n DNA content with some G2 cells after DNA replication showing as 2n. The contamination with diploid cells is low as judged from the 4n peak corresponding to G2 cells. A diploid control ES cell line (lower panel) shows a 2n G1 peak and a 4n G2 peak.

FIG. 3

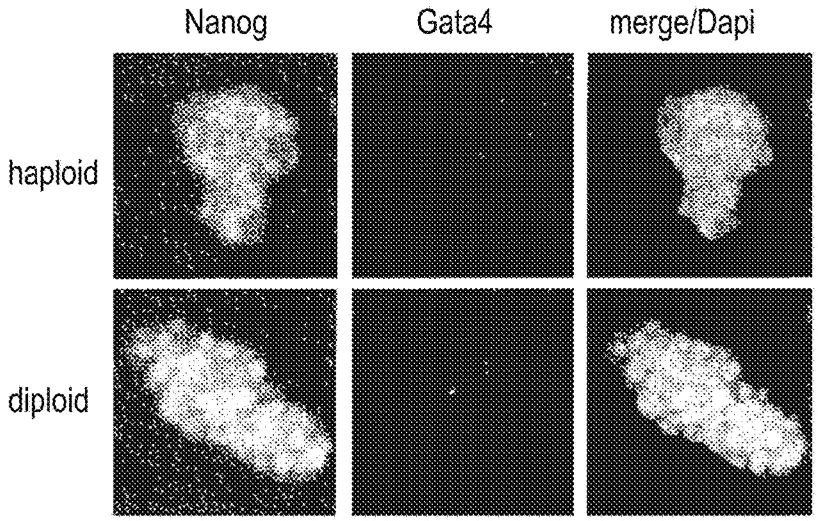

Characterization of a haploid mouse embryonic stem (ES) cell line

Immunofluorescence staining of haploid and control diploid ES cells for detecting Nanog, a marker of pluripotent ES cells, and Gata4, a marker of early ES differentiation marker. Colonies of both haploid and control diploid ES cells express the pluripotency marker Nanog but do not express markers that are indicative of differentiation.

Derivation of CBA/B6 hybrid haploid ES cells in KSR

(a) A flow profile of DNA content after PI staining recorded from diploid control shows a 2n and 4n peak.
(b) A flow profile of DNA content of an ES cell line (HAP-9, p8) derived from haploid blastocysts using Knockout Serum Replacement shows an additional 1n peak.

Derivation of haploid ES cells from a mixed genetic background in 2i medium

(a) A flow profile shows the DNA content of a diploid control ES cell line after PI staining.

(b) A flow profile of a haploid ES cell line (HTG-1, p8) derived from blastocysts with a mixed genetic background shows a nearly pure haploid cell population with 1n and 2n peaks but no 4n peak.

FIG. 10A

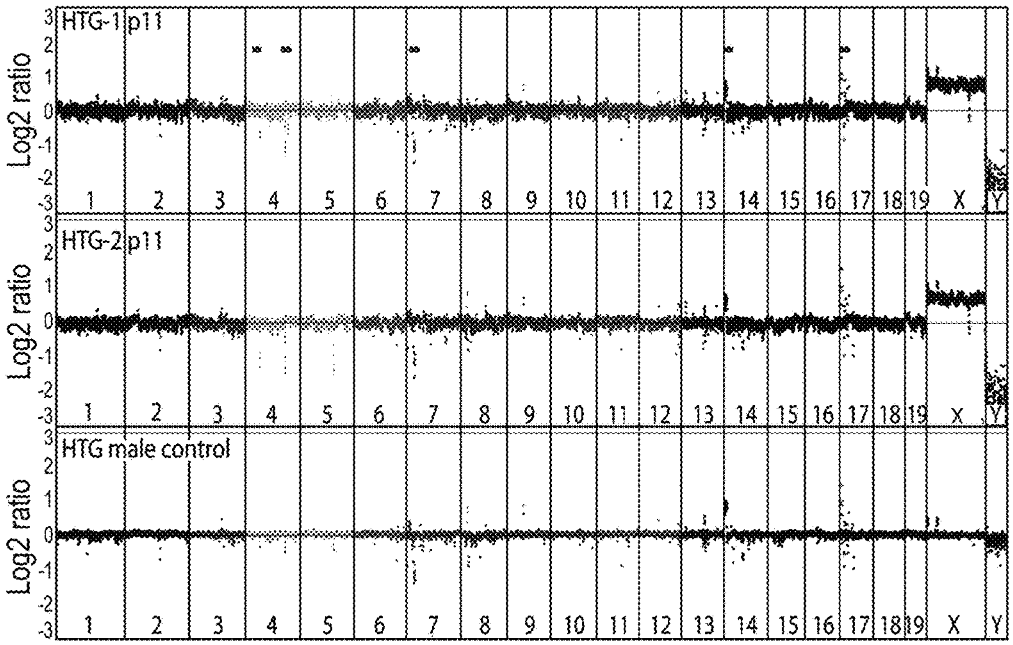

FIG. 10B

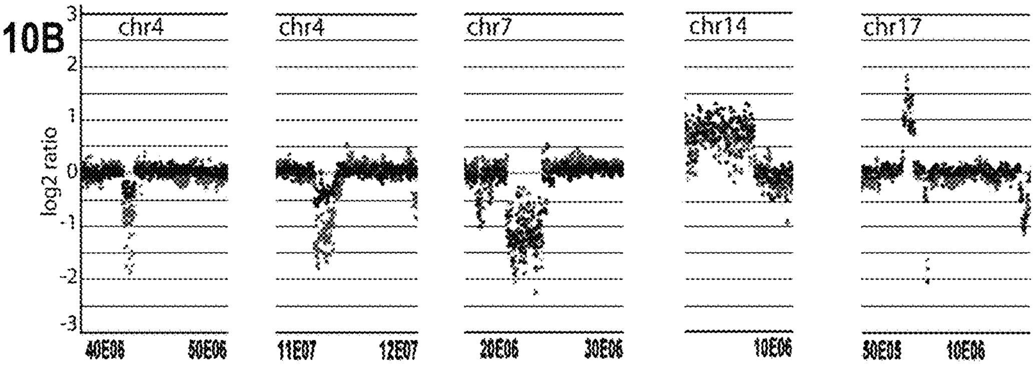

CGH analysis of HTG haploid ES cells.

(a) Genomic overview of copy number variations (CNVs) in 200kb resolution in HTG-1 and HTG-2 haploid ES cells and control male kidney DNA from the mixed strain background of which the ES cells were derived. Average values of log2 ratios are plotted using somatic C57BL6 DNA as a reference. Blue bars on top indicate the positions of regions enlarged in panel b.

(b) Zoom in views of regions with CNVs on chromosomes 4, 7, 14 and X are shown.

Signals from somatic kidney DNA from HTG genetic background mouse strain (black), HTG-1 (green) and HTG-2 (red) ES cells are overlaid and shown at 40 kb resolution. The positions of CNVs overlap indicating they are likely resulting from genomic variation between the strain of origin and C57BL6 mouse strains.

FIG. 11

CGH analysis of haploid ES cells

CGH profiles of HAP-1, HAP-2, HTG-1 and HTG-2 haploid mouse ES cells are shown along genomic coordinates. Kidney DNA from a CBA male mouse and from a male of the transgenic mixed background strain from which HTG ES cells were derived were analysed as controls. All hybridizations were performed using a C57BL6 male DNA reference. Average values of log2 ratios are plotted at a 40 kb resolution.

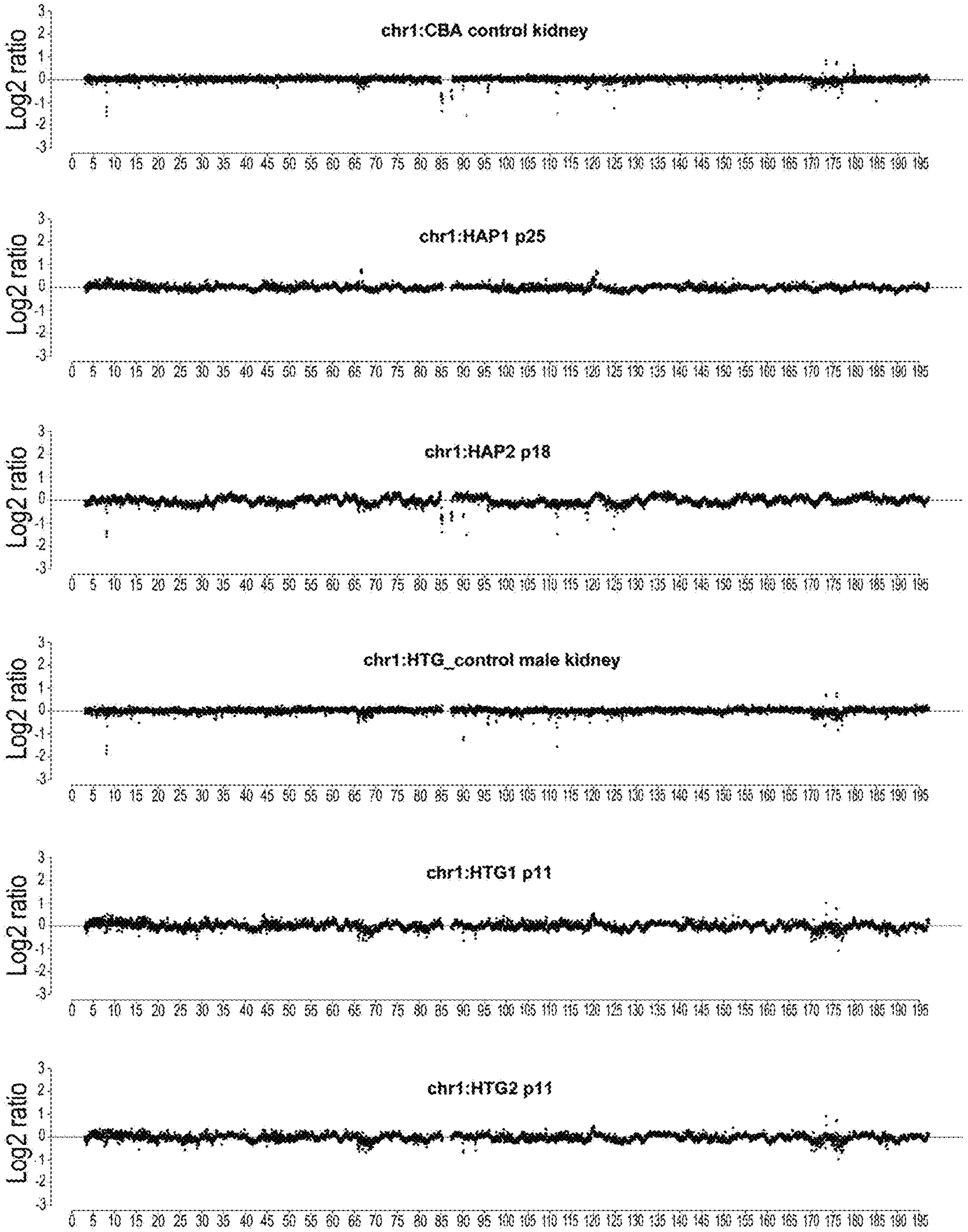

FIG. 11 continued
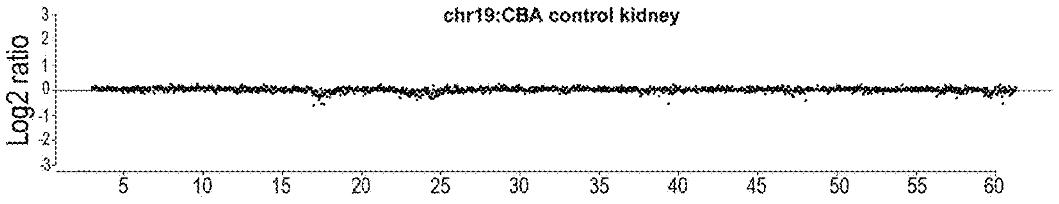
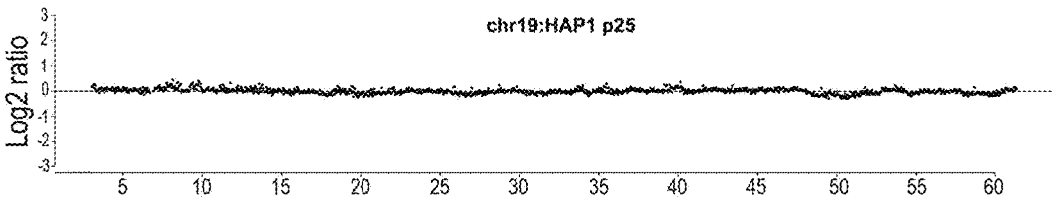
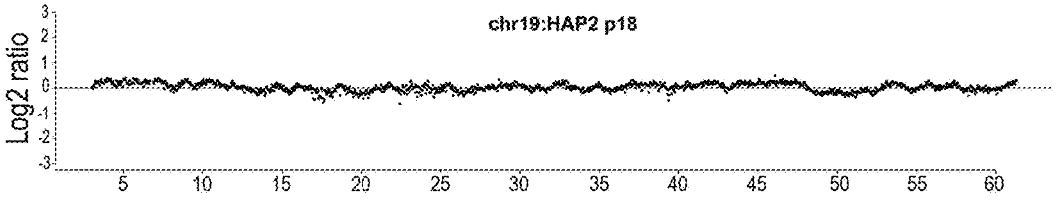
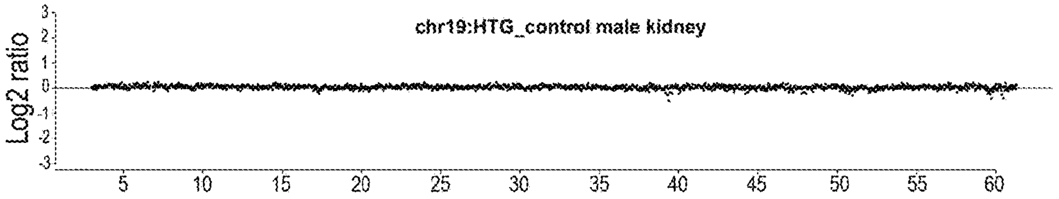
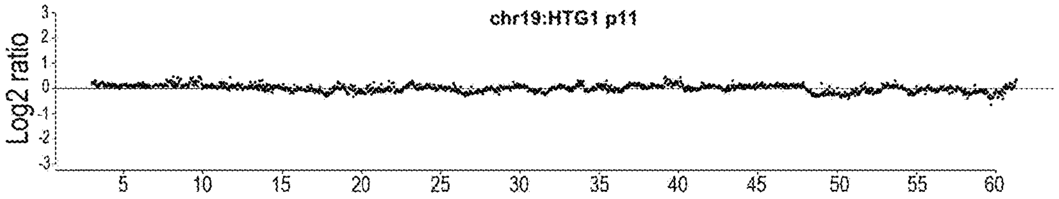
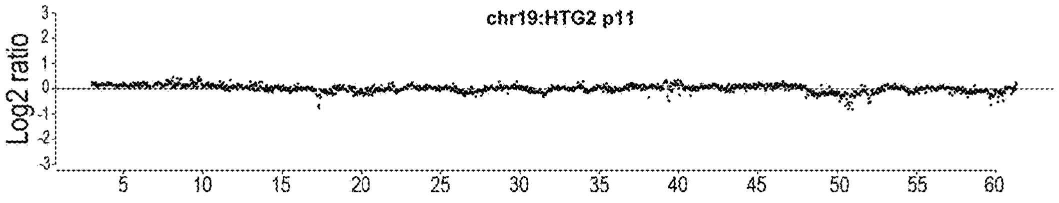

FIG. 12

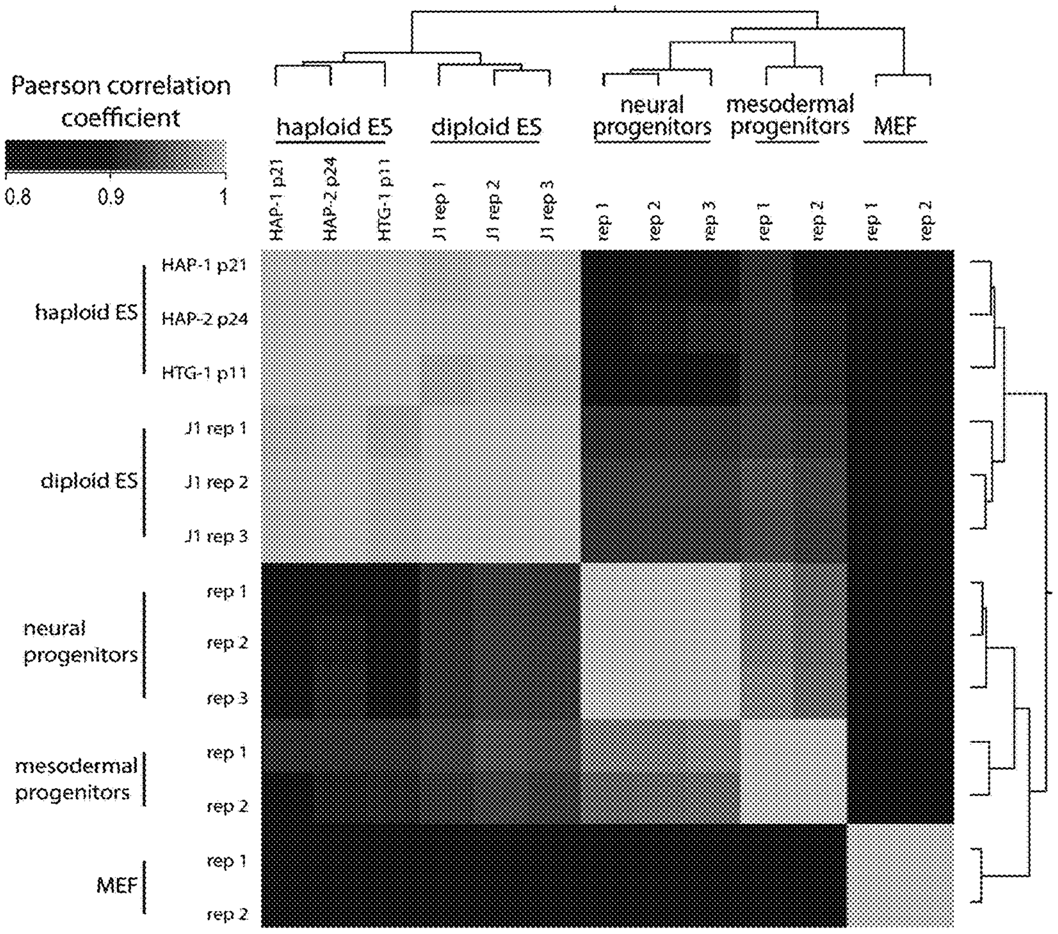

Analysis of similarity between haploid and diploid ES cells

An overview of the gene expression profiles of haploid and diploid ES cells is shown. Gene expression profiles were clustered using all genes and the Paerson correlation coefficient was calculated (indicated by red color). Three different haploid ES cell lines (HAP-1, HAP-2, and HTG-1) cluster together showing highly similar expression profiles. Gene expression of haploid ES cells is highly similar to control diploid J1 ES cells but different from mouse embryonic fibroblasts (MEF) or neural and mesodermal progenitors. The dendrogram (top and right) was generated by hierarchical clustering by Euclidean distance and complete linkage analysis (rep1, rep2, rep3 indicate biological replicates).

Stable integration of a GFP transgene into haploid ES cells

Flow profiles show the (a) DNA content and (b) DNA content combined with GFP intensity of HAP-2 ES cells transfected with a piggyBac vector for expressing GFP. The 1n / GFP positive population was purified for analysis of the developmental potential of haploid ES cells.

FIG. 14A

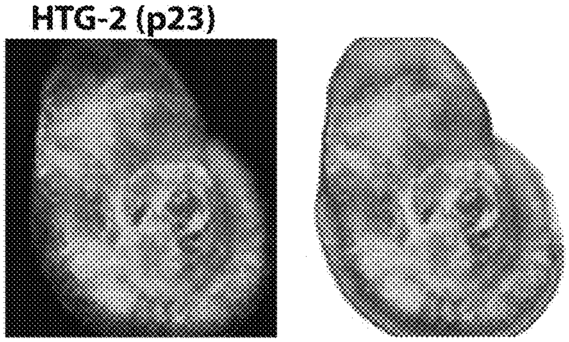

FIG. 14B

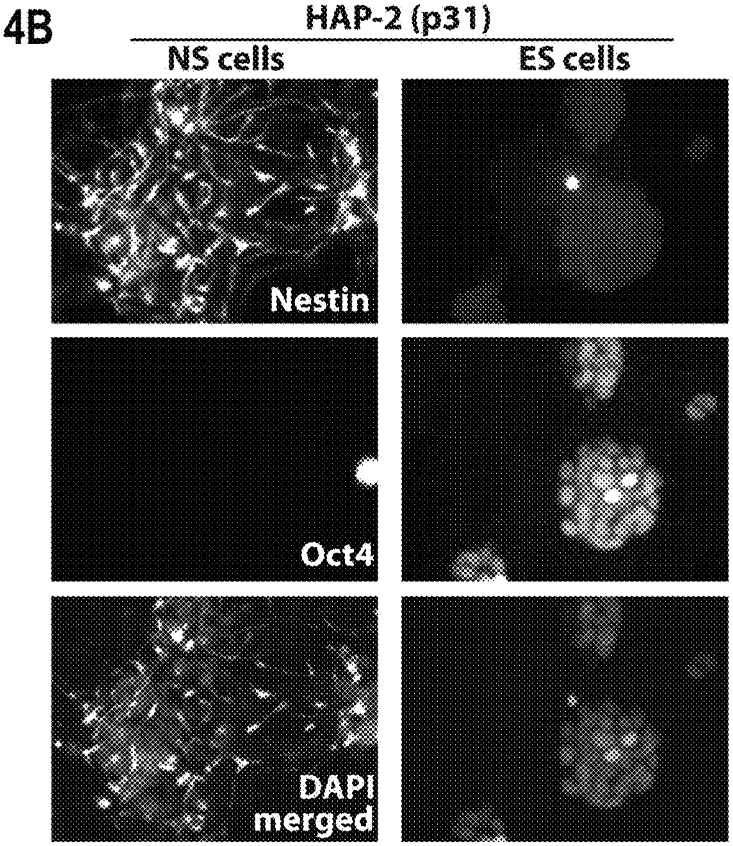

Developmental potential of haploid ES cells.

(a) A GFP image and merged GFP brightfield image of a chimeric E9.5 embryo from injection of GFP labeled HTG-2 ES cells (p23) into C57BL6 host blastocysts.

(b) Immunofluorescence analysis of Nestin (green) and Oct4 (white) expression in HAP-2 (p31) ES cells and HAP-2 derived neural stem (NS) cells. A merged image with DNA stained with DAPI (blue) is shown below.

FIG. 15A

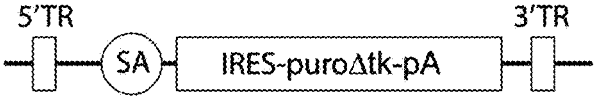

FIG. 15B

Genetrap insertions recovered in missmatch repair screen

(a) A schematic representation of the piggyBac genetrap vector is shown (SA, splice acceptor).

(b) Genome browser view shows BLAST hits for sequences recovered by Splinkerette PCR from 6-TG resistant clones obtained from a missmatch repair screen using haploid mouse ES cells (see text). Seven clones were analysed and three insertions into genes previously identified to mediate 6-TG sensitivity were identified. Two independent insertions in the *Msh2* and one insertion in the *Hprt* gene are shown. The integration sites were mapped to intron three and fifteen of *Msh2* on chromosome 17 at base position 88,081,425 and 88,121,546, respectively. A further insertion was identified in intron 1 of the *Hprt* gene at base position 50,349,004 on the X chromosome. All gene trap insertions were in forward orientation trapping the gene transcripts as expected. Genomic positions and gene structure are based on the NCBI37/mm9 assembly of the mouse genome.

FIG. 16

Segmentation table of the CGH analysis of haploid ES cells

Segmentation analysis of the CGH profiles of HAP-1, HAP-2, HTG-1 and HTG-2 haploid mouse ES cells and CBA and HTG control male somatic samples was performed using the NimbleScan software (Roche). Copynumber deviations with a cut-off log2 value of 0.8 were determined and listed with chromosome and genomic position.

HAP1

| CHROMOSOMI | START | STOP | SIZE | DATAPOINTS | LOG2_RATIO_ |
|---|---|---|---|---|---|
| chr7 | 3699999 | 3819999 | 120000 | 43 | -1.4371 |
| chr7 | 20699999 | 24059999 | 3360000 | 637 | -1.88153 |
| chr12 | 89299999 | 89379999 | 80000 | 34 | -0.89872 |
| chr13 | 68619999 | 68699999 | 80000 | 32 | -1.03683 |
| chr14 | 42059999 | 42219999 | 160000 | 54 | -1.32819 |
| chr14 | 42259999 | 42339999 | 80000 | 29 | -0.89743 |
| chr14 | 42379999 | 42419999 | 40000 | 14 | -1.37748 |
| chr14 | 42459999 | 42539999 | 80000 | 28 | -0.84389 |
| chr14 | 42579999 | 42659999 | 80000 | 33 | -1.58313 |
| chr14 | 42699999 | 42859999 | 160000 | 49 | -1.15406 |
| chr14 | 42899999 | 43019999 | 120000 | 40 | -1.66039 |
| chr14 | 43059999 | 43379999 | 320000 | 92 | -1.39357 |
| chr14 | 43419999 | 43619999 | 200000 | 48 | -1.70756 |
| chr14 | 43659999 | 43859999 | 200000 | 63 | -1.0446 |
| chr14 | 43899999 | 44099999 | 200000 | 66 | -1.44165 |
| chr14 | 44139999 | 44259999 | 120000 | 38 | -0.81347 |
| chr14 | 44539999 | 44579999 | 40000 | 22 | -1.67539 |
| chr14 | 44739999 | 44819999 | 80000 | 33 | -0.90922 |
| chr14 | 44859999 | 45179999 | 320000 | 84 | -1.32847 |
| chr14 | 45219999 | 45259999 | 40000 | 22 | -1.68286 |
| chr14 | 45299999 | 45339999 | 40000 | 21 | -1.2028 |
| chr14 | 52259999 | 52379999 | 120000 | 43 | -0.83266 |
| chrX | 1.22E+08 | 1.22E+08 | 400000 | 26 | -1.31437 |
| chrX | 1.22E+08 | 1.23E+08 | 440000 | 37 | -1.45574 |

HAP2

| CHROMOSOMI | START | STOP | SIZE | DATAPOINTS | LOG2_RATIO_ |
|---|---|---|---|---|---|
| chr1 | 8139999 | 8219999 | 80000 | 32 | -1.15655 |
| chr2 | 1E+08 | 1.01E+08 | 280000 | 89 | -0.91674 |
| chr8 | 19339999 | 19379999 | 40000 | 20 | -1.06806 |
| chr8 | 22179999 | 22299999 | 120000 | 41 | -0.97395 |
| chr8 | 22539999 | 22699999 | 160000 | 47 | -1.10896 |
| chr13 | 68619999 | 68699999 | 80000 | 32 | -0.82539 |
| chr16 | 35499999 | 35539999 | 40000 | 24 | 0.88028 |
| chr17 | 6259999 | 6899999 | 640000 | 180 | 1.45984 |
| chr17 | 30619999 | 31019999 | 400000 | 124 | 1.01428 |
| chr17 | 35539999 | 35579999 | 40000 | 22 | -1.37624 |
| chrX | 3019999 | 4939999 | 1920000 | 288 | 0.84469 |
| chrX | 6659999 | 8019999 | 1360000 | 391 | 0.85511 |
| chrX | 19699999 | 20699999 | 1000000 | 291 | 0.80541 |
| chrX | 70699999 | 71699999 | 1000000 | 295 | 0.91882 |

CBA

| CHROMOSOMI | START | STOP | SIZE | DATAPOINTS | LOG2_RATIO_ |
|---|---|---|---|---|---|
| chr1 | 8139999 | 8219999 | 80000 | 32 | -1.12563 |
| chr3 | 93579999 | 93659999 | 80000 | 34 | 0.91478 |
| chr4 | 41739999 | 42779999 | 1040000 | 218 | -1.07415 |
| chr4 | 1.12E+08 | 1.12E+08 | 520000 | 152 | -1.31422 |
| chr4 | 1.12E+08 | 1.14E+08 | 1080000 | 302 | -1.22262 |
| chr4 | 1.21E+08 | 1.22E+08 | 760000 | 190 | -1.51206 |
| chr5 | 14939999 | 15179999 | 240000 | 65 | -0.81371 |
| chr5 | 1.05E+08 | 1.05E+08 | 320000 | 98 | -0.83343 |
| chr6 | 1.14E+08 | 1.15E+08 | 80000 | 21 | 0.80806 |
| chr6 | 1.3E+08 | 1.3E+08 | 200000 | 67 | -1.26461 |
| chr6 | 1.32E+08 | 1.32E+08 | 120000 | 42 | -1.17524 |
| chr7 | 3699999 | 3819999 | 120000 | 43 | -1.36942 |
| chr7 | 20699999 | 24059999 | 3360000 | 637 | -1.7698 |
| chr7 | 1.11E+08 | 1.11E+08 | 40000 | 22 | -1.44423 |
| chr8 | 19339999 | 19379999 | 40000 | 20 | -1.03835 |
| chr8 | 22179999 | 22299999 | 120000 | 41 | -0.87322 |
| chr8 | 22539999 | 22699999 | 160000 | 47 | -1.0725 |
| chr10 | 1.14E+08 | 1.14E+08 | 560000 | 166 | 0.82654 |
| chr14 | 42059999 | 42219999 | 160000 | 54 | -1.2489 |
| chr14 | 42259999 | 42539999 | 280000 | 71 | -1.0259 |
| chr14 | 42579999 | 43379999 | 800000 | 214 | -1.30787 |
| chr14 | 43419999 | 43499999 | 80000 | 18 | -1.72834 |
| chr14 | 43539999 | 43579999 | 40000 | 20 | -0.91193 |
| chr14 | 43619999 | 43659999 | 40000 | 20 | -1.53924 |
| chr14 | 43699999 | 44099999 | 400000 | 119 | -1.14346 |
| chr14 | 44539999 | 44579999 | 40000 | 22 | -1.29833 |
| chr14 | 44779999 | 45339999 | 560000 | 149 | -1.1872 |
| chr16 | 36259999 | 36299999 | 40000 | 23 | -1.03884 |
| chr17 | 6259999 | 6899999 | 640000 | 180 | 1.33058 |
| chr17 | 30619999 | 31059999 | 440000 | 135 | 0.81562 |
| chr17 | 35539999 | 35579999 | 40000 | 22 | -1.38383 |

FIG. 16 continued

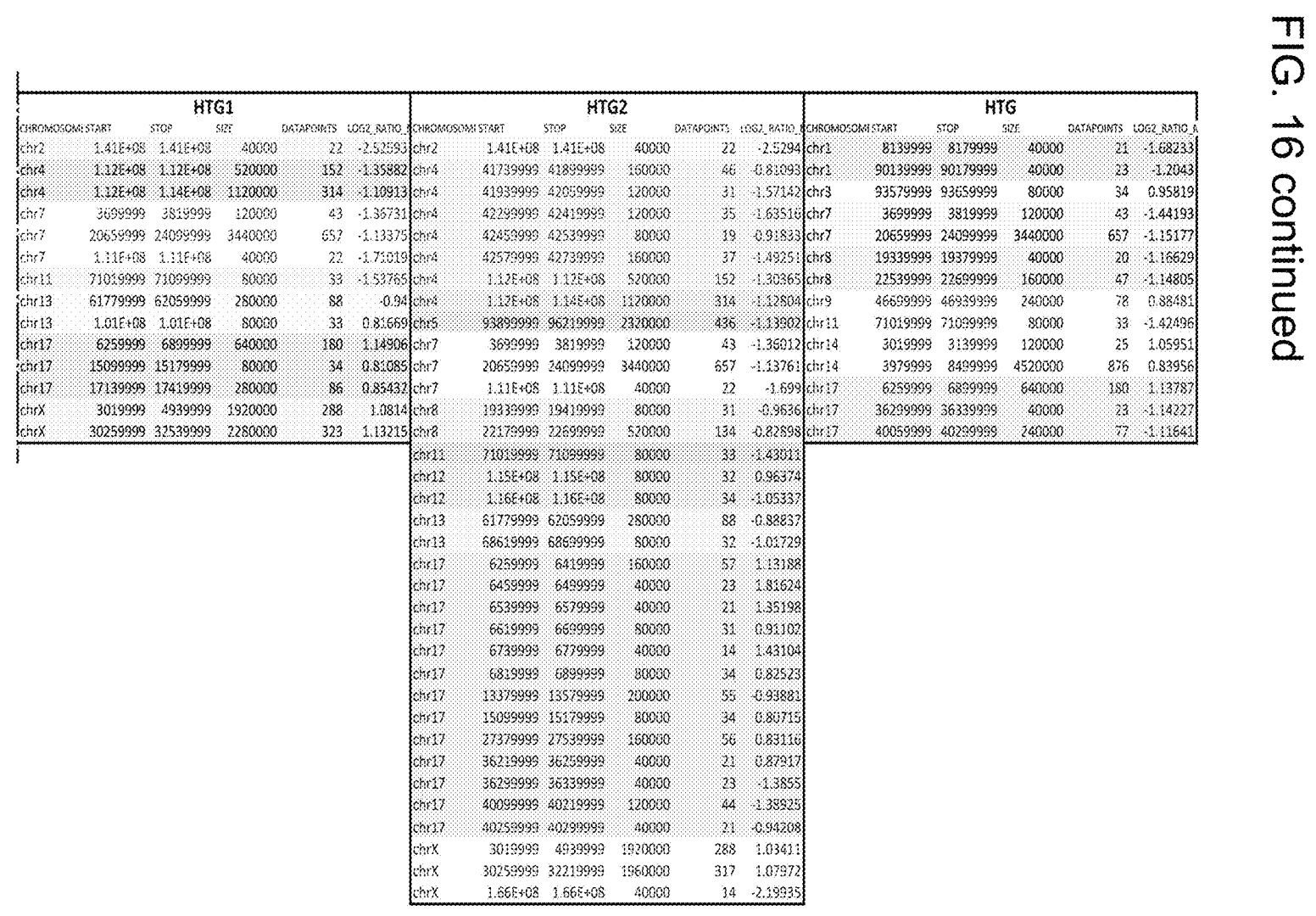

HTG1

| CHROMOSOME | START | STOP | SIZE | DATAPOINTS | LOG2_RATIO_ |
|---|---|---|---|---|---|
| chr2 | 1.41E+08 | 1.41E+08 | 40000 | 22 | -2.52593 |
| chr4 | 1.12E+08 | 1.12E+08 | 520000 | 152 | -1.35882 |
| chr4 | 1.12E+08 | 1.14E+08 | 1120000 | 314 | -1.10913 |
| chr7 | 3699999 | 3819999 | 120000 | 43 | -1.36731 |
| chr7 | 20659999 | 24099999 | 3440000 | 657 | -1.13375 |
| chr7 | 1.11E+08 | 1.11E+08 | 40000 | 22 | -1.71019 |
| chr11 | 71019999 | 71099999 | 80000 | 33 | -1.53765 |
| chr13 | 61779999 | 62059999 | 280000 | 88 | -0.94 |
| chr13 | 1.01E+08 | 1.01E+08 | 80000 | 33 | 0.81669 |
| chr17 | 6259999 | 6899999 | 640000 | 180 | 1.14906 |
| chr17 | 15099999 | 15179999 | 80000 | 34 | 0.81085 |
| chr17 | 17139999 | 17419999 | 280000 | 86 | 0.85432 |
| chrX | 3019999 | 4939999 | 1920000 | 288 | 1.0814 |
| chrX | 30259999 | 32539999 | 2280000 | 323 | 1.13215 |

HTG2

| CHROMOSOME | START | STOP | SIZE | DATAPOINTS | LOG2_RATIO_ |
|---|---|---|---|---|---|
| chr2 | 1.41E+08 | 1.41E+08 | 40000 | 22 | -2.5294 |
| chr4 | 41739999 | 41899999 | 160000 | 46 | -0.81093 |
| chr4 | 41939999 | 42059999 | 120000 | 31 | -1.57142 |
| chr4 | 42299999 | 42419999 | 120000 | 35 | -1.63516 |
| chr4 | 42459999 | 42539999 | 80000 | 19 | -0.91833 |
| chr4 | 42579999 | 42739999 | 160000 | 37 | -1.49251 |
| chr4 | 1.12E+08 | 1.12E+08 | 520000 | 152 | -1.30365 |
| chr4 | 1.12E+08 | 1.14E+08 | 1120000 | 314 | -1.12804 |
| chr5 | 93899999 | 96219999 | 2320000 | 436 | -1.13902 |
| chr7 | 3699999 | 3819999 | 120000 | 43 | -1.36012 |
| chr7 | 20659999 | 24099999 | 3440000 | 657 | -1.13761 |
| chr7 | 1.11E+08 | 1.11E+08 | 40000 | 22 | -1.699 |
| chr8 | 19339999 | 19419999 | 80000 | 31 | -0.9636 |
| chr8 | 22179999 | 22699999 | 520000 | 134 | -0.82898 |
| chr11 | 71019999 | 71099999 | 80000 | 33 | -1.43011 |
| chr12 | 1.15E+08 | 1.15E+08 | 80000 | 32 | 0.96374 |
| chr12 | 1.16E+08 | 1.16E+08 | 80000 | 34 | -1.05337 |
| chr13 | 61779999 | 62059999 | 280000 | 88 | -0.88837 |
| chr13 | 68619999 | 68699999 | 80000 | 32 | -1.01729 |
| chr17 | 6259999 | 6419999 | 160000 | 57 | 1.13188 |
| chr17 | 6459999 | 6499999 | 40000 | 23 | 1.81624 |
| chr17 | 6539999 | 6579999 | 40000 | 21 | 1.35198 |
| chr17 | 6619999 | 6699999 | 80000 | 31 | 0.91102 |
| chr17 | 6739999 | 6779999 | 40000 | 14 | 1.43104 |
| chr17 | 6819999 | 6899999 | 80000 | 34 | 0.82523 |
| chr17 | 13379999 | 13579999 | 200000 | 55 | -0.93881 |
| chr17 | 15099999 | 15179999 | 80000 | 34 | 0.80715 |
| chr17 | 27379999 | 27539999 | 160000 | 56 | 0.83116 |
| chr17 | 36219999 | 36259999 | 40000 | 21 | 0.87917 |
| chr17 | 36299999 | 36339999 | 40000 | 23 | -1.3855 |
| chr17 | 40099999 | 40219999 | 120000 | 44 | -1.38925 |
| chr17 | 40259999 | 40299999 | 40000 | 21 | -0.94208 |
| chrX | 3019999 | 4939999 | 1920000 | 288 | 1.03411 |
| chrX | 30259999 | 32219999 | 1960000 | 317 | 1.07972 |
| chrX | 1.66E+08 | 1.66E+08 | 40000 | 14 | -2.19935 |

HTG

| CHROMOSOME | START | STOP | SIZE | DATAPOINTS | LOG2_RATIO_A |
|---|---|---|---|---|---|
| chr1 | 8139999 | 8179999 | 40000 | 21 | -1.68233 |
| chr1 | 90139999 | 90179999 | 40000 | 23 | -1.2043 |
| chr3 | 93579999 | 93659999 | 80000 | 34 | 0.95819 |
| chr7 | 3699999 | 3819999 | 120000 | 43 | -1.44193 |
| chr7 | 20659999 | 24099999 | 3440000 | 657 | -1.15177 |
| chr8 | 19339999 | 19379999 | 40000 | 20 | -1.16629 |
| chr8 | 22539999 | 22699999 | 160000 | 47 | -1.14805 |
| chr9 | 46699999 | 46939999 | 240000 | 78 | 0.88481 |
| chr11 | 71019999 | 71099999 | 80000 | 33 | -1.42496 |
| chr14 | 3019999 | 3139999 | 120000 | 25 | 1.05951 |
| chr14 | 3979999 | 8499999 | 4520000 | 876 | 0.83956 |
| chr17 | 6259999 | 6899999 | 640000 | 180 | 1.13787 |
| chr17 | 36299999 | 36339999 | 40000 | 23 | -1.14227 |
| chr17 | 40059999 | 40299999 | 240000 | 77 | -1.11641 |

FIG. 17 differentially regulated genes in haploid ES cells (> 2 fold; p<0.05)

Upregulated genes in haploid vs diploid ES cells

| | Probe Set ID | Fold change | Gene Symbol | Entrez Gene | Gene Description |
|---|---|---|---|---|---|
| 1 | 1434068_s_at | 11.99 | AI662270 | 103814 | expressed sequence AI662270 |
| 2 | 1416749_at | 10.76 | Htra1 | 56213 | HtrA serine peptidase 1 |
| 3 | 1419540_at | 8.46 | EG434726 /// Fthl17 | 434726 /// 434727 /// | predicted gene 14458 |
| 4 | 1460670_at | 8.39 | Riok3 | 66878 | RIO kinase 3 (yeast) |
| 5 | 1419134_at | 7.66 | Rhbg | 58176 | Rhesus blood group-associated B glycoprotein |
| 6 | 1436107_at | 7.51 | Lsm8 | 76522 | LSM8 homolog, U6 small nuclear RNA associated (S. cerevisiae) |
| 7 | 1427512_a_at | 7.47 | Lama3 | 16774 | laminin, alpha 3 |
| 8 | 1450001_a_at | 7.34 | Ush1c | 72088 | Usher syndrome 1C homolog (human) |
| 9 | 1456036_x_at | 7.24 | Gsto1 | 14873 | glutathione S-transferase omega 1 |
| 10 | 1454799_at | 7.01 | Agpat9 | 231510 | 1-acylglycerol-3-phosphate O-acyltransferase 9 |
| 11 | 1424692_at | 6.90 | 2810055F11Rik | 67217 | RIKEN cDNA 2810055F11 gene |
| 12 | 1436355_at | 6.73 | Fads6 | 328035 | fatty acid desaturase domain family, member 6 |
| 13 | 1454869_at | 6.60 | Wdr40b | 245404 | WD repeat domain 40B |
| 14 | 1453977_at | 6.54 | Exoc4 | 20336 | exocyst complex component 4 |
| 15 | 1437152_at | 6.40 | Mex3b | 108797 | mex3 homolog B (C. elegans) |
| 16 | 1454737_at | 6.27 | Dusp9 | 75590 | dual specificity phosphatase 9 |
| 17 | 1437867_at | 5.95 | | | |
| 18 | 1416531_at | 5.83 | Gsto1 | 14873 | glutathione S-transferase omega 1 |
| 19 | 1426988_at | 5.80 | Klhdc5 | 232539 | kelch domain containing 5 |
| 20 | 1450460_at | 5.53 | Aqp3 | 11828 | aquaporin 3 |
| 21 | 1422008_a_at | 5.53 | Aqp3 | 11828 | aquaporin 3 |
| 22 | 1421385_a_at | 5.33 | Myo7a | 17921 | myosin VIIA |
| 23 | 1445281_a_at | 5.28 | B230311B06Rik | 381914 | RIKEN cDNA B230311B06 gene |
| 24 | 1444416_at | 5.26 | Cenpa | 12615 | centromere protein A |
| 25 | 1429308_at | 5.23 | Prdm16 | 70673 | PR domain containing 16 |
| 26 | 1433845_x_at | 5.15 | Dusp9 | 75590 | dual specificity phosphatase 9 |
| 27 | 1438251_x_at | 4.82 | Htra1 | 56213 | HtrA serine peptidase 1 |
| 28 | 1449031_at | 4.79 | Cited1 | 12705 | Cbp/p300-interacting transactivator with Glu/Asp-rich carboxy-terminal domain 1 |
| 29 | 1437409_s_at | 4.78 | Gpr126 | 215798 | G protein-coupled receptor 126 |
| 30 | 1438238_at | 4.72 | 2010315B03Rik | 630836 | RIKEN cDNA 2010315B03 gene |
| 31 | 1426223_at | 4.66 | Ttc39c | 72747 | tetratricopeptide repeat domain 39C |
| 32 | 1435948_at | 4.40 | Tmem181 /// Tmem | 100040525 /// 77106 | transmembrane protein 181C, pseudogene |
| 33 | 1448596_at | 4.13 | Slc6a8 | 102857 | solute carrier family 6 (neurotransmitter transporter, creatine), member 8 |
| 34 | 1438842_at | 4.09 | Mtch2 | 56428 | mitochondrial carrier homolog 2 (C. elegans); predicted gene, 100039384; predi |
| 35 | 1417120_at | 4.08 | Miip | 28010 | migration and invasion inhibitory protein |
| 36 | 1449036_at | 4.05 | Rnf128 | 66889 | ring finger protein 128 |
| 37 | 1439422_a_at | 4.04 | Fam132a | 67389 | family with sequence similarity 132, member A |
| 38 | 1429169_at | 4.03 | Rbm3 | 19652 | predicted gene 15453; RNA binding motif protein 3 |
| 39 | 1424082_at | 4.03 | Tbc1d13 | 70296 | TBC1 domain family, member 13 |
| 40 | 1429504_at | 3.97 | Rnpc3 | 67225 | RNA-binding region (RNP1, RRM) containing 3 |

FIG. 17 continued

| | Probe Set ID | Fold change | Gene Symbol | Entrez Gene | Gene Description |
|---|---|---|---|---|---|
| 41 | 1444226_at | 3.78 | Foxo3 | 56484 | forkhead box O3 |
| 42 | 1418681_at | 3.75 | Alg13 | 67574 | asparagine-linked glycosylation 13 homolog (S. cerevisiae) |
| 43 | 1451754_a_at | 3.71 | Wdr45 | 54636 | WD repeat domain 45 |
| 44 | 1433844_a_at | 3.60 | Dusp9 | 75590 | dual specificity phosphatase 9 |
| 45 | 1456804_at | 3.57 | EG627821 | 627821 | predicted gene 6792 |
| 46 | 1437302_at | 3.56 | Adrb2 | 11555 | adrenergic receptor, beta 2 |
| 47 | 1450843_a_at | 3.55 | Serpinh1 | 12406 | serine (or cysteine) peptidase inhibitor, clade H, member 1 |
| 48 | 1459740_s_at | 3.55 | Ucp2 | 22228 | uncoupling protein 2 (mitochondrial, proton carrier) |
| 49 | 1428933_at | 3.53 | Hdac8 | 70315 | histone deacetylase 8 |
| 50 | 1451148_at | 3.52 | LOC100047214 /// F | 100047214 /// 68943 | similar to PTEN induced putative kinase 1 |
| 51 | 1422743_at | 3.48 | Phka1 | 18679 | phosphorylase kinase alpha 1 |
| 52 | 1454009_at | 3.45 | 1700008O03Rik | 69349 | RIKEN cDNA 1700008O03 gene |
| 53 | 1438750_at | 3.42 | Atrx | 22589 | alpha thalassemia/mental retardation syndrome X-linked homolog (human) |
| 54 | 1448599_s_at | 3.39 | Miip | 28010 | migration and invasion inhibitory protein |
| 55 | 1426241_a_at | 3.38 | Scmh1 | 29871 | sex comb on midleg homolog 1 |
| 56 | 1435069_at | 3.35 | BC064078 | 408064 | cDNA sequence BC064078 |
| 57 | 1425601_a_at | 3.34 | Rtkn | 20166 | rhotekin |
| 58 | 1430538_at | 3.28 | 2210013O21Rik | 70123 | RIKEN cDNA 2210013O21 gene |
| 59 | 1417116_at | 3.26 | Slc6a8 | 102857 | solute carrier family 6 (neurotransmitter transporter, creatine), member 8 |
| 60 | 1422823_at | 3.26 | Eps8 /// LOC63263ε | 13860 /// 632638 | epidermal growth factor receptor pathway substrate 8 |
| 61 | 1434092_at | 3.22 | Atg9b | 213948 | ATG9 autophagy related 9 homolog B (S. cerevisiae) |
| 62 | 1416239_at | 3.20 | Ass1 | 11898 | argininosuccinate synthetase 1 |
| 63 | 1455721_at | 3.20 | Gspt2 | 14853 | G1 to S phase transition 2 |
| 64 | 1436200_at | 3.19 | Lonrf3 | 74365 | LON peptidase N-terminal domain and ring finger 3 |
| 65 | 1425466_s_at | 3.19 | Rps6kl1 | 238323 | ribosomal protein S6 kinase-like 1 |
| 66 | 1418318_at | 3.16 | Rnf128 | 66889 | ring finger protein 128 |
| 67 | 1435514_at | 3.14 | Lztfl1 | 93730 | leucine zipper transcription factor-like 1; predicted gene 6776 |
| 68 | 1449476_at | 3.14 | Rage | 26448 | renal tumor antigen |
| 69 | 1447957_at | 3.09 | D7Ertd128e | 52222 | DNA segment, Chr 7, ERATO Doi 128, expressed |
| 70 | 1422711_a_at | 3.08 | Pnck | 93843 | pregnancy upregulated non-ubiquitously expressed CaM kinase |
| 71 | 1417850_at | 3.04 | Rb1 | 19645 | retinoblastoma 1 |
| 72 | 1422744_at | 3.02 | Phka1 | 18679 | phosphorylase kinase alpha 1 |
| 73 | 1427564_at | 3.02 | Diap2 | 54004 | diaphanous homolog 2 (Drosophila) |
| 74 | 1451169_at | 3.02 | Nomo1 | 211548 | nodal modulator 1 |
| 75 | 1448330_at | 3.01 | Gstm1 | 14862 | similar to Glutathione S-transferase Mu 1 (GST class-mu 1) (Glutathione S-trans |
| 76 | 1455817_x_at | 3.00 | Zxdb | 668166 | zinc finger, X-linked, duplicated B |
| 77 | 1451269_at | 2.99 | Pdzd11 | 72621 | PDZ domain containing 11 |
| 78 | 1446583_at | 2.97 | | | |
| 79 | 1449119_at | 2.97 | Arih2 | 23807 | ariadne homolog 2 (Drosophila); predicted gene 12263 |
| 80 | 1437369_at | 2.97 | Fgd1 | 14163 | FYVE, RhoGEF and PH domain containing 1 |
| 81 | 1460600_at | 2.96 | AA414768 | 245350 | expressed sequence AA414768 |
| 82 | 1453040_at | 2.96 | Mcart6 | 67062 | mitochondrial carrier triple repeat 6 |
| 83 | 1424838_at | 2.95 | A330049M08Rik | 230822 | RIKEN cDNA A330049M08 gene |
| 84 | 1450919_at | 2.93 | Mpp1 | 17524 | membrane protein, palmitoylated |
| 85 | 1425068_a_at | 2.91 | Tex264 | 21767 | testis expressed gene 264 |
| 86 | 1444057_at | 2.91 | | | UBX domain protein 4 |
| 87 | 1434493_at | 2.91 | 1810022K09Rik | 69126 | predicted gene 4540; RIKEN cDNA 1810022K09 gene |
| 88 | 1421896_at | 2.91 | Elk1 | 13712 | ELK1, member of ETS oncogene family |
| 89 | 1422327_s_at | 2.90 | G6pd2 /// G6pdx | 14380 /// 14381 | glucose-6-phosphate dehydrogenase 2 |
| 90 | 1437449_at | 2.90 | Rsad1 | 237926 | radical S-adenosyl methionine domain containing 1 |

FIG. 17 continued

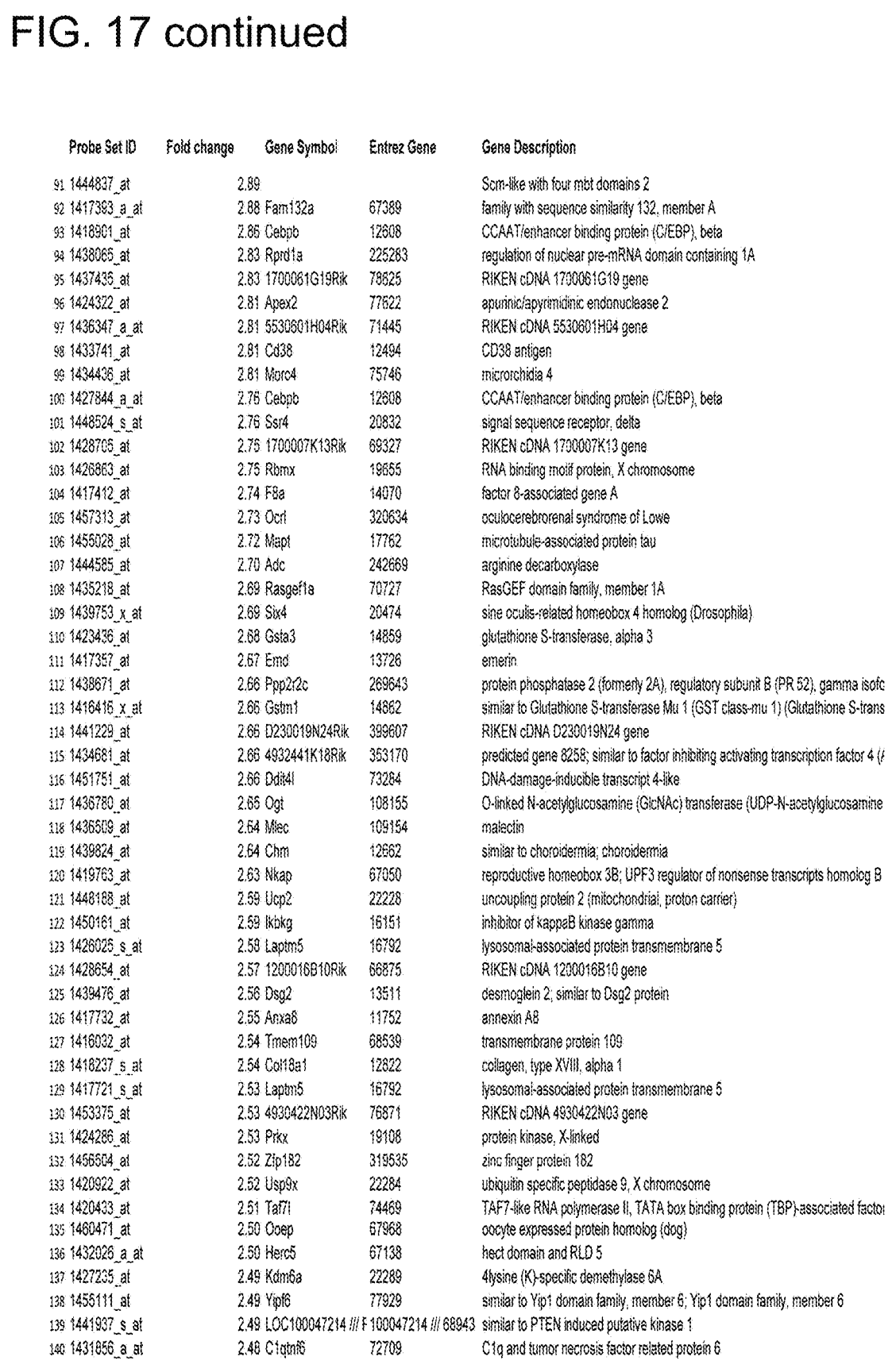

| | Probe Set ID | Fold change | Gene Symbol | Entrez Gene | Gene Description |
|---|---|---|---|---|---|
| 91 | 1444837_at | 2.89 | | | Scm-like with four mbt domains 2 |
| 92 | 1417393_a_at | 2.88 | Fam132a | 67389 | family with sequence similarity 132, member A |
| 93 | 1418901_at | 2.86 | Cebpb | 12608 | CCAAT/enhancer binding protein (C/EBP), beta |
| 94 | 1438065_at | 2.83 | Rprd1a | 225283 | regulation of nuclear pre-mRNA domain containing 1A |
| 95 | 1437436_at | 2.83 | 1700061G19Rik | 78625 | RIKEN cDNA 1700061G19 gene |
| 96 | 1424322_at | 2.81 | Apex2 | 77622 | apurinic/apyrimidinic endonuclease 2 |
| 97 | 1436347_a_at | 2.81 | 5530601H04Rik | 71445 | RIKEN cDNA 5530601H04 gene |
| 98 | 1433741_at | 2.81 | Cd38 | 12494 | CD38 antigen |
| 99 | 1434436_at | 2.81 | Morc4 | 75746 | microrchidia 4 |
| 100 | 1427844_a_at | 2.76 | Cebpb | 12608 | CCAAT/enhancer binding protein (C/EBP), beta |
| 101 | 1448524_s_at | 2.76 | Ssr4 | 20832 | signal sequence receptor, delta |
| 102 | 1428705_at | 2.75 | 1700007K13Rik | 69327 | RIKEN cDNA 1700007K13 gene |
| 103 | 1426863_at | 2.75 | Rbmx | 19655 | RNA binding motif protein, X chromosome |
| 104 | 1417412_at | 2.74 | F8a | 14070 | factor 8-associated gene A |
| 105 | 1457313_at | 2.73 | Ocrl | 320634 | oculocerebrorenal syndrome of Lowe |
| 106 | 1455028_at | 2.72 | Mapt | 17762 | microtubule-associated protein tau |
| 107 | 1444585_at | 2.70 | Adc | 242669 | arginine decarboxylase |
| 108 | 1435218_at | 2.69 | Rasgef1a | 70727 | RasGEF domain family, member 1A |
| 109 | 1439753_x_at | 2.69 | Six4 | 20474 | sine oculis-related homeobox 4 homolog (Drosophila) |
| 110 | 1423436_at | 2.68 | Gsta3 | 14859 | glutathione S-transferase, alpha 3 |
| 111 | 1417357_at | 2.67 | Emd | 13726 | emerin |
| 112 | 1438671_at | 2.66 | Ppp2r2c | 269643 | protein phosphatase 2 (formerly 2A), regulatory subunit B (PR 52), gamma isofc |
| 113 | 1416416_x_at | 2.66 | Gstm1 | 14862 | similar to Glutathione S-transferase Mu 1 (GST class-mu 1) (Glutathione S-trans |
| 114 | 1441229_at | 2.66 | D230019N24Rik | 399607 | RIKEN cDNA D230019N24 gene |
| 115 | 1434681_at | 2.66 | 4932441K18Rik | 353170 | predicted gene 8258; similar to factor inhibiting activating transcription factor 4 (/ |
| 116 | 1451751_at | 2.66 | Ddit4l | 73284 | DNA-damage-inducible transcript 4-like |
| 117 | 1436780_at | 2.65 | Ogt | 108155 | O-linked N-acetylglucosamine (GlcNAc) transferase (UDP-N-acetylglucosamine |
| 118 | 1436509_at | 2.64 | Mlec | 109154 | malectin |
| 119 | 1439824_at | 2.64 | Chm | 12662 | similar to choroidermia; choroidermia |
| 120 | 1419763_at | 2.63 | Nkap | 67050 | reproductive homeobox 3B; UPF3 regulator of nonsense transcripts homolog B |
| 121 | 1448188_at | 2.59 | Ucp2 | 22228 | uncoupling protein 2 (mitochondrial, proton carrier) |
| 122 | 1450161_at | 2.59 | Ikbkg | 16151 | inhibitor of kappaB kinase gamma |
| 123 | 1426025_s_at | 2.58 | Laptm5 | 16792 | lysosomal-associated protein transmembrane 5 |
| 124 | 1428654_at | 2.57 | 1200016B10Rik | 66875 | RIKEN cDNA 1200016B10 gene |
| 125 | 1439476_at | 2.56 | Dsg2 | 13511 | desmoglein 2; similar to Dsg2 protein |
| 126 | 1417732_at | 2.55 | Anxa8 | 11752 | annexin A8 |
| 127 | 1416032_at | 2.54 | Tmem109 | 68539 | transmembrane protein 109 |
| 128 | 1418237_s_at | 2.54 | Col18a1 | 12822 | collagen, type XVIII, alpha 1 |
| 129 | 1417721_s_at | 2.53 | Laptm5 | 16792 | lysosomal-associated protein transmembrane 5 |
| 130 | 1453375_at | 2.53 | 4930422N03Rik | 76871 | RIKEN cDNA 4930422N03 gene |
| 131 | 1424286_at | 2.53 | Prkx | 19108 | protein kinase, X-linked |
| 132 | 1456504_at | 2.52 | Zfp182 | 319535 | zinc finger protein 182 |
| 133 | 1420922_at | 2.52 | Usp9x | 22284 | ubiquitin specific peptidase 9, X chromosome |
| 134 | 1420433_at | 2.51 | Taf7l | 74469 | TAF7-like RNA polymerase II, TATA box binding protein (TBP)-associated facto |
| 135 | 1460471_at | 2.50 | Ooep | 67968 | oocyte expressed protein homolog (dog) |
| 136 | 1432026_a_at | 2.50 | Herc5 | 67138 | hect domain and RLD 5 |
| 137 | 1427235_at | 2.49 | Kdm6a | 22289 | 4lysine (K)-specific demethylase 6A |
| 138 | 1456111_at | 2.49 | Yipf6 | 77929 | similar to Yip1 domain family, member 6; Yip1 domain family, member 6 |
| 139 | 1441937_s_at | 2.49 | LOC100047214 /// F | 100047214 /// 68943 | similar to PTEN induced putative kinase 1 |
| 140 | 1431856_a_at | 2.48 | C1qtnf6 | 72709 | C1q and tumor necrosis factor related protein 6 |

FIG. 17 continued

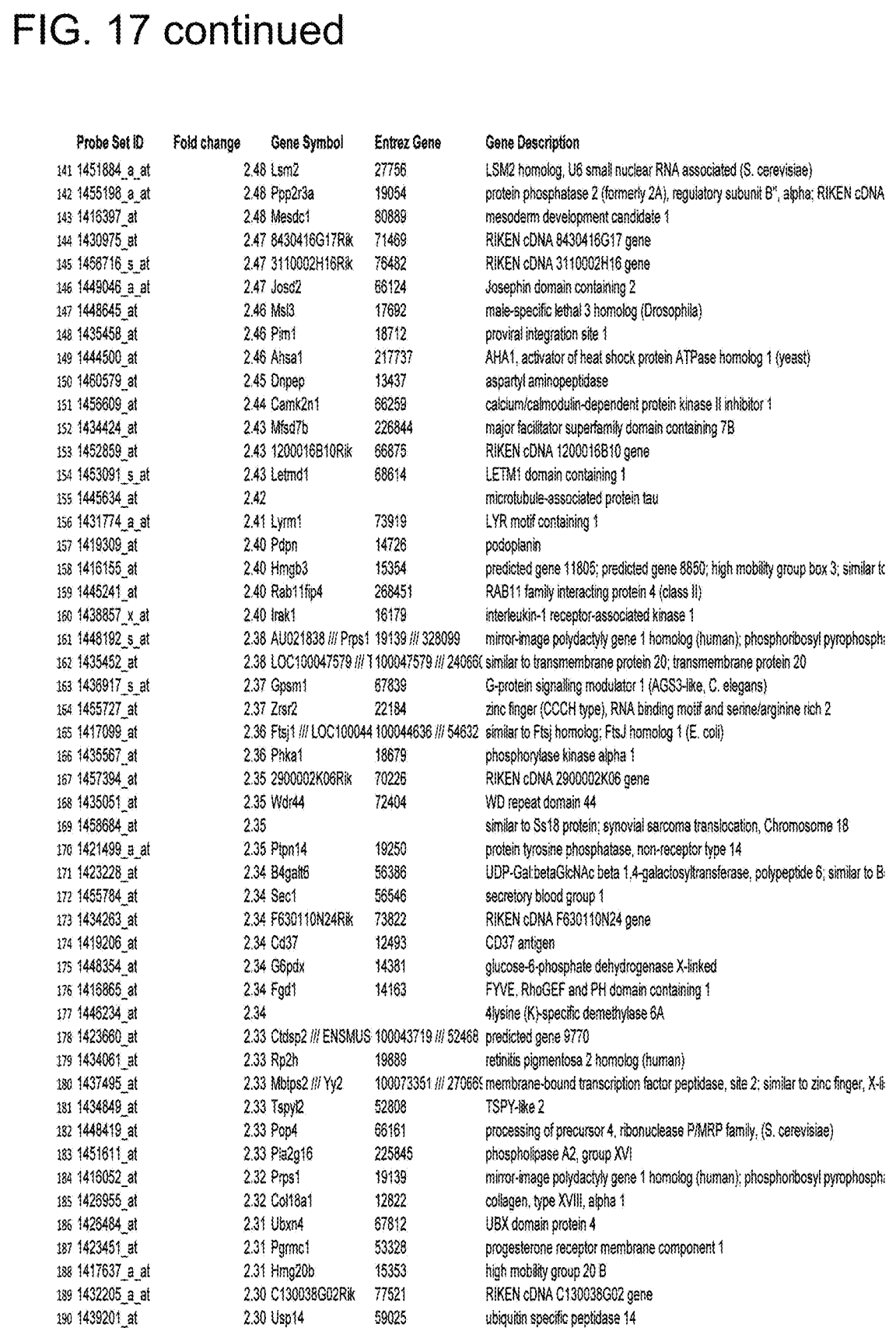

| | Probe Set ID | Fold change | Gene Symbol | Entrez Gene | Gene Description |
|---|---|---|---|---|---|
| 141 | 1451884_a_at | 2.48 | Lsm2 | 27756 | LSM2 homolog, U6 small nuclear RNA associated (S. cerevisiae) |
| 142 | 1455198_a_at | 2.48 | Ppp2r3a | 19054 | protein phosphatase 2 (formerly 2A), regulatory subunit B'', alpha; RIKEN cDNA |
| 143 | 1416397_at | 2.48 | Mesdc1 | 80889 | mesoderm development candidate 1 |
| 144 | 1430975_at | 2.47 | 8430416G17Rik | 71469 | RIKEN cDNA 8430416G17 gene |
| 145 | 1456716_s_at | 2.47 | 3110002H16Rik | 76482 | RIKEN cDNA 3110002H16 gene |
| 146 | 1449046_a_at | 2.47 | Josd2 | 66124 | Josephin domain containing 2 |
| 147 | 1448645_at | 2.46 | Msl3 | 17692 | male-specific lethal 3 homolog (Drosophila) |
| 148 | 1435458_at | 2.46 | Pim1 | 18712 | proviral integration site 1 |
| 149 | 1444500_at | 2.46 | Ahsa1 | 217737 | AHA1, activator of heat shock protein ATPase homolog 1 (yeast) |
| 150 | 1460579_at | 2.45 | Dnpep | 13437 | aspartyl aminopeptidase |
| 151 | 1456609_at | 2.44 | Camk2n1 | 66259 | calcium/calmodulin-dependent protein kinase II inhibitor 1 |
| 152 | 1434424_at | 2.43 | Mfsd7b | 226844 | major facilitator superfamily domain containing 7B |
| 153 | 1452859_at | 2.43 | 1200016B10Rik | 66875 | RIKEN cDNA 1200016B10 gene |
| 154 | 1453091_s_at | 2.43 | Letmd1 | 68614 | LETM1 domain containing 1 |
| 155 | 1445634_at | 2.42 | | | microtubule-associated protein tau |
| 156 | 1431774_a_at | 2.41 | Lyrm1 | 73919 | LYR motif containing 1 |
| 157 | 1419309_at | 2.40 | Pdpn | 14726 | podoplanin |
| 158 | 1416155_at | 2.40 | Hmgb3 | 15354 | predicted gene 11805; predicted gene 8850; high mobility group box 3; similar tc |
| 159 | 1445241_at | 2.40 | Rab11fip4 | 268451 | RAB11 family interacting protein 4 (class II) |
| 160 | 1438857_x_at | 2.40 | Irak1 | 16179 | interleukin-1 receptor-associated kinase 1 |
| 161 | 1448192_s_at | 2.38 | AU021838 /// Prps1 | 19139 /// 328099 | mirror-image polydactyly gene 1 homolog (human); phosphoribosyl pyrophosph: |
| 162 | 1435452_at | 2.38 | LOC100047579 /// T | 100047579 /// 24066( | similar to transmembrane protein 20; transmembrane protein 20 |
| 163 | 1436917_s_at | 2.37 | Gpsm1 | 67839 | G-protein signalling modulator 1 (AGS3-like, C. elegans) |
| 164 | 1455727_at | 2.37 | Zrsr2 | 22184 | zinc finger (CCCH type), RNA binding motif and serine/arginine rich 2 |
| 165 | 1417099_at | 2.36 | Ftsj1 /// LOC100044 | 100044636 /// 54632 | similar to Ftsj homolog; FtsJ homolog 1 (E. coli) |
| 166 | 1435567_at | 2.36 | Phka1 | 18679 | phosphorylase kinase alpha 1 |
| 167 | 1457394_at | 2.35 | 2900002K06Rik | 70226 | RIKEN cDNA 2900002K06 gene |
| 168 | 1435051_at | 2.35 | Wdr44 | 72404 | WD repeat domain 44 |
| 169 | 1458684_at | 2.35 | | | similar to Ss18 protein; synovial sarcoma translocation, Chromosome 18 |
| 170 | 1421499_a_at | 2.35 | Ptpn14 | 19250 | protein tyrosine phosphatase, non-receptor type 14 |
| 171 | 1423228_at | 2.34 | B4galt6 | 56386 | UDP-Gal:betaGlcNAc beta 1,4-galactosyltransferase, polypeptide 6; similar to B: |
| 172 | 1455784_at | 2.34 | Sec1 | 56546 | secretory blood group 1 |
| 173 | 1434263_at | 2.34 | F630110N24Rik | 73822 | RIKEN cDNA F630110N24 gene |
| 174 | 1419206_at | 2.34 | Cd37 | 12493 | CD37 antigen |
| 175 | 1448354_at | 2.34 | G6pdx | 14381 | glucose-6-phosphate dehydrogenase X-linked |
| 176 | 1418865_at | 2.34 | Fgd1 | 14163 | FYVE, RhoGEF and PH domain containing 1 |
| 177 | 1446234_at | 2.34 | | | 4lysine (K)-specific demethylase 6A |
| 178 | 1423660_at | 2.33 | Ctdsp2 /// ENSMUS | 100043719 /// 52468 | predicted gene 9770 |
| 179 | 1434061_at | 2.33 | Rp2h | 19889 | retinitis pigmentosa 2 homolog (human) |
| 180 | 1437495_at | 2.33 | Mbtps2 /// Yy2 | 100073351 /// 27066! | membrane-bound transcription factor peptidase, site 2; similar to zinc finger, X-li |
| 181 | 1434849_at | 2.33 | Tspyl2 | 52808 | TSPY-like 2 |
| 182 | 1448419_at | 2.33 | Pop4 | 66161 | processing of precursor 4, ribonuclease P/MRP family, (S. cerevisiae) |
| 183 | 1451611_at | 2.33 | Pla2g16 | 225845 | phospholipase A2, group XVI |
| 184 | 1416052_at | 2.32 | Prps1 | 19139 | mirror-image polydactyly gene 1 homolog (human); phosphoribosyl pyrophosph: |
| 185 | 1426955_at | 2.32 | Col18a1 | 12822 | collagen, type XVIII, alpha 1 |
| 186 | 1426484_at | 2.31 | Ubxn4 | 67812 | UBX domain protein 4 |
| 187 | 1423451_at | 2.31 | Pgrmc1 | 53328 | progesterone receptor membrane component 1 |
| 188 | 1417637_a_at | 2.31 | Hmg20b | 15353 | high mobility group 20 B |
| 189 | 1432205_a_at | 2.30 | C130038G02Rik | 77521 | RIKEN cDNA C130038G02 gene |
| 190 | 1439201_at | 2.30 | Usp14 | 59025 | ubiquitin specific peptidase 14 |

FIG. 17 continued

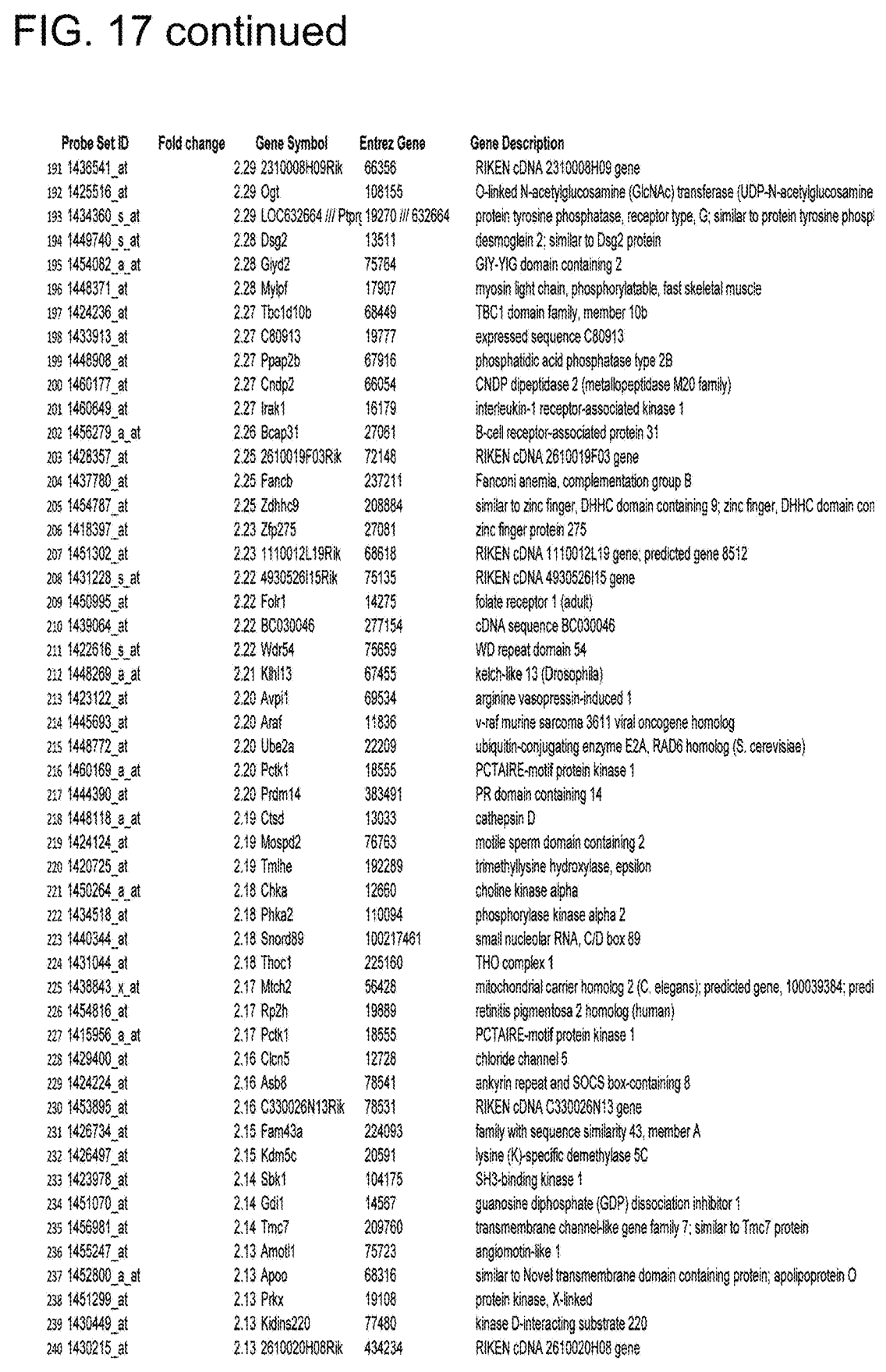

| | Probe Set ID | Fold change | Gene Symbol | Entrez Gene | Gene Description |
|---|---|---|---|---|---|
| 191 | 1436541_at | 2.29 | 2310008H09Rik | 66356 | RIKEN cDNA 2310008H09 gene |
| 192 | 1425516_at | 2.29 | Ogt | 108155 | O-linked N-acetylglucosamine (GlcNAc) transferase (UDP-N-acetylglucosamine |
| 193 | 1434360_s_at | 2.29 | LOC632664 /// Ptpr( | 19270 /// 632664 | protein tyrosine phosphatase, receptor type, G; similar to protein tyrosine phosp |
| 194 | 1449740_s_at | 2.28 | Dsg2 | 13511 | desmoglein 2; similar to Dsg2 protein |
| 195 | 1454082_a_at | 2.28 | Giyd2 | 75764 | GIY-YIG domain containing 2 |
| 196 | 1448371_at | 2.28 | Mylpf | 17907 | myosin light chain, phosphorylatable, fast skeletal muscle |
| 197 | 1424236_at | 2.27 | Tbc1d10b | 68449 | TBC1 domain family, member 10b |
| 198 | 1433913_at | 2.27 | C80913 | 19777 | expressed sequence C80913 |
| 199 | 1448908_at | 2.27 | Ppap2b | 67916 | phosphatidic acid phosphatase type 2B |
| 200 | 1460177_at | 2.27 | Cndp2 | 66054 | CNDP dipeptidase 2 (metallopeptidase M20 family) |
| 201 | 1460649_at | 2.27 | Irak1 | 16179 | interleukin-1 receptor-associated kinase 1 |
| 202 | 1456279_a_at | 2.26 | Bcap31 | 27061 | B-cell receptor-associated protein 31 |
| 203 | 1428357_at | 2.26 | 2610019F03Rik | 72148 | RIKEN cDNA 2610019F03 gene |
| 204 | 1437780_at | 2.25 | Fancb | 237211 | Fanconi anemia, complementation group B |
| 205 | 1454787_at | 2.25 | Zdhhc9 | 208884 | similar to zinc finger, DHHC domain containing 9; zinc finger, DHHC domain con |
| 206 | 1418397_at | 2.23 | Zfp275 | 27081 | zinc finger protein 275 |
| 207 | 1451302_at | 2.23 | 1110012L19Rik | 68618 | RIKEN cDNA 1110012L19 gene; predicted gene 8512 |
| 208 | 1431228_s_at | 2.22 | 4930526I15Rik | 75135 | RIKEN cDNA 4930526I15 gene |
| 209 | 1450995_at | 2.22 | Folr1 | 14275 | folate receptor 1 (adult) |
| 210 | 1439064_at | 2.22 | BC030046 | 277154 | cDNA sequence BC030046 |
| 211 | 1422616_s_at | 2.22 | Wdr54 | 75659 | WD repeat domain 54 |
| 212 | 1448269_a_at | 2.21 | Klhl13 | 67455 | kelch-like 13 (Drosophila) |
| 213 | 1423122_at | 2.20 | Avpi1 | 69534 | arginine vasopressin-induced 1 |
| 214 | 1445693_at | 2.20 | Araf | 11836 | v-raf murine sarcoma 3611 viral oncogene homolog |
| 215 | 1448772_at | 2.20 | Ube2a | 22209 | ubiquitin-conjugating enzyme E2A, RAD6 homolog (S. cerevisiae) |
| 216 | 1460169_a_at | 2.20 | Pctk1 | 18555 | PCTAIRE-motif protein kinase 1 |
| 217 | 1444390_at | 2.20 | Prdm14 | 383491 | PR domain containing 14 |
| 218 | 1448118_a_at | 2.19 | Ctsd | 13033 | cathepsin D |
| 219 | 1424124_at | 2.19 | Mospd2 | 76763 | motile sperm domain containing 2 |
| 220 | 1420725_at | 2.19 | Tmlhe | 192289 | trimethyllysine hydroxylase, epsilon |
| 221 | 1450264_a_at | 2.18 | Chka | 12660 | choline kinase alpha |
| 222 | 1434518_at | 2.18 | Phka2 | 110094 | phosphorylase kinase alpha 2 |
| 223 | 1440344_at | 2.18 | Snord89 | 100217461 | small nucleolar RNA, C/D box 89 |
| 224 | 1431044_at | 2.18 | Thoc1 | 225160 | THO complex 1 |
| 225 | 1438843_x_at | 2.17 | Mtch2 | 56428 | mitochondrial carrier homolog 2 (C. elegans); predicted gene, 100039384; predi |
| 226 | 1454816_at | 2.17 | Rp2h | 19889 | retinitis pigmentosa 2 homolog (human) |
| 227 | 1415956_a_at | 2.17 | Pctk1 | 18555 | PCTAIRE-motif protein kinase 1 |
| 228 | 1429400_at | 2.16 | Clcn5 | 12728 | chloride channel 5 |
| 229 | 1424224_at | 2.16 | Asb8 | 78541 | ankyrin repeat and SOCS box-containing 8 |
| 230 | 1453895_at | 2.16 | C330026N13Rik | 78531 | RIKEN cDNA C330026N13 gene |
| 231 | 1426734_at | 2.15 | Fam43a | 224093 | family with sequence similarity 43, member A |
| 232 | 1426497_at | 2.15 | Kdm5c | 20591 | lysine (K)-specific demethylase 5C |
| 233 | 1423978_at | 2.14 | Sbk1 | 104175 | SH3-binding kinase 1 |
| 234 | 1451070_at | 2.14 | Gdi1 | 14567 | guanosine diphosphate (GDP) dissociation inhibitor 1 |
| 235 | 1456981_at | 2.14 | Tmc7 | 209760 | transmembrane channel-like gene family 7; similar to Tmc7 protein |
| 236 | 1455247_at | 2.13 | Amotl1 | 75723 | angiomotin-like 1 |
| 237 | 1452800_a_at | 2.13 | Apoo | 68316 | similar to Novel transmembrane domain containing protein; apolipoprotein O |
| 238 | 1451299_at | 2.13 | Prkx | 19108 | protein kinase, X-linked |
| 239 | 1430449_at | 2.13 | Kidins220 | 77480 | kinase D-interacting substrate 220 |
| 240 | 1430215_at | 2.13 | 2610020H08Rik | 434234 | RIKEN cDNA 2610020H08 gene |

FIG. 17 continued

| | Probe Set ID | Fold change | Gene Symbol | Entrez Gene | Gene Description |
|---|---|---|---|---|---|
| 241 | 1450107_a_at | 2.12 | Renbp | 19703 | renin binding protein |
| 242 | 1435860_at | 2.12 | Slc5a6 | 330064 | solute carrier family 5 (sodium-dependent vitamin transporter), member 6 |
| 243 | 1422965_at | 2.11 | Agtrap | 11610 | angiotensin II, type I receptor-associated protein |
| 244 | 1424167_a_at | 2.11 | Pmm1 | 29858 | phosphomannomutase 1 |
| 245 | 1423662_at | 2.11 | Atp6ap2 | 70495 | ATPase, H+ transporting, lysosomal accessory protein 2 |
| 246 | 1420909_at | 2.11 | Vegfa | 22339 | vascular endothelial growth factor A |
| 247 | 1438270_at | 2.11 | AI846148 | 68229 | expressed sequence AI846148 |
| 248 | 1427573_at | 2.11 | Chic1 | 12212 | cysteine-rich hydrophobic domain 1 |
| 249 | 1458358_at | 2.11 | Pank2 | 74450 | pantothenate kinase 2 (Hallervorden-Spatz syndrome) |
| 250 | 1436905_x_at | 2.11 | Laptm5 | 16792 | lysosomal-associated protein transmembrane 5 |
| 251 | 1421797_a_at | 2.10 | Snx12 | 55988 | sorting nexin 12 |
| 252 | 1428334_at | 2.10 | Ostm1 | 14628 | osteopetrosis associated transmembrane protein 1 |
| 253 | 1450038_s_at | 2.10 | Usp9x | 22284 | ubiquitin specific peptidase 9, X chromosome |
| 254 | 1439631_at | 2.09 | Zcchc11 | 230594 | zinc finger, CCHC domain containing 11 |
| 255 | 1448668_a_at | 2.09 | Irak1 | 16179 | interleukin-1 receptor-associated kinase 1 |
| 256 | 1426410_at | 2.08 | Pdk3 | 236900 | pyruvate dehydrogenase kinase, isoenzyme 3 |
| 257 | 1441391_at | 2.07 | | | guanine nucleotide binding protein (G protein), beta polypeptide 1-like; similar to |
| 258 | 1449622_s_at | 2.07 | Atp6ap1 | 54411 | ATPase, H+ transporting, lysosomal accessory protein 1 |
| 259 | 1426306_a_at | 2.07 | LOC100046560 /// M | 100046560 /// 80884 | similar to melanoma antigen family D, 2; melanoma antigen, family D, 2 |
| 260 | 1457316_at | 2.07 | Mtap6 | 17760 | microtubule-associated protein 6 |
| 261 | 1417442_a_at | 2.06 | Pex3 | 56535 | peroxisomal biogenesis factor 3 |
| 262 | 1451049_at | 2.05 | Bcap31 | 27061 | B-cell receptor-associated protein 31 |
| 263 | 1435008_at | 2.05 | Slc9a6 | 236794 | solute carrier family 9 (sodium/hydrogen exchanger), member 6 |
| 264 | 1424106_at | 2.05 | 1200003C05Rik | 104771 | RIKEN cDNA 1200003C05 gene |
| 265 | 1423661_s_at | 2.04 | Ctdsp2 /// ENSMUS | 100043719 /// 52468 | predicted gene 9770 |
| 266 | 1435566_s_at | 2.04 | Araf | 11836 | v-raf murine sarcoma 3611 viral oncogene homolog |
| 267 | 1451400_at | 2.04 | Gemin8 | 237221 | similar to gem (nuclear organelle) associated protein 8; predicted gene 5455; ge |
| 268 | 1428773_s_at | 2.04 | Bcor | 71458 | BCL6 interacting corepressor |
| 269 | 1432158_a_at | 2.04 | Trappc2 | 66226 | similar to Chain A, The Crystal Structure Of The Bet3-Trs31-Sedlin Complex; tra |
| 270 | 1449916_at | 2.02 | Pbx4 | 80720 | pre-B-cell leukemia homeobox 4 |
| 271 | 1432011_at | 2.02 | 2900052L18Rik | 76835 | predicted gene 4407; RIKEN cDNA 2900052L18 gene |
| 272 | 1434908_at | 2.02 | Scaf1 | 233208 | SR-related CTD-associated factor 1 |
| 273 | 1441970_at | 2.02 | E430010N07Rik | 399572 | RIKEN cDNA E430010N07 gene |
| 274 | 1429776_a_at | 2.02 | Dnajb6 | 23950 | DnaJ (Hsp40) homolog, subfamily B, member 6; predicted gene 5917; predictec |
| 275 | 1425525_a_at | 2.01 | P2rx4 | 18438 | purinergic receptor P2X, ligand-gated ion channel 4 |
| 276 | 1436300_at | 2.01 | Dstyk | 213452 | dual serine/threonine and tyrosine protein kinase |
| 277 | 1430780_a_at | 2.01 | Pmm1 | 29858 | phosphomannomutase 1 |

FIG. 17 continued

Downregulated genes in haploid vs diploid ES cells

| | Probe Set ID | Fold change | Gene Symbol | Entrez Gene | Gene Description |
|---|---|---|---|---|---|
| 1 | 1417210_at | -46.94 | Eif2s3y | 26908 | eukaryotic translation initiation factor 2, subunit 3, structural gene Y-linked |
| 2 | 1443621_at | -34.01 | Xaf1 | 327959 | XIAP associated factor 1 |
| 3 | 1426438_at | -32.17 | Ddx3y | 26900 | DEAD (Asp-Glu-Ala-Asp) box polypeptide 3, Y-linked |
| 4 | 1445226_at | -23.48 | BC023969 | 407828 | cDNA sequence BC023969 |
| 5 | 1452077_at | -21.18 | Ddx3y | 26900 | DEAD (Asp-Glu-Ala-Asp) box polypeptide 3, Y-linked |
| 6 | 1427302_at | -12.31 | Enpp3 | 209558 | ectonucleotide pyrophosphatase/phosphodiesterase 3 |
| 7 | 1416371_at | -10.48 | Apod | 11815 | apolipoprotein D |
| 8 | 1437721_at | -9.30 | Coro1c | 23790 | coronin, actin binding protein 1C; predicted gene 5790 |
| 9 | 1438833_at | -9.18 | Casc5 | 76464 | cancer susceptibility candidate 5 |
| 10 | 1415949_at | -8.97 | Cpe /// LOC100046 | 100046434 /// 12876 | carboxypeptidase E; similar to carboxypeptidase E |
| 11 | 1438933_x_at | -7.94 | Rasgrp2 | 19395 | RAS, guanyl releasing protein 2 |
| 12 | 1415897_a_at | -7.72 | Mgst1 | 56615 | microsomal glutathione S-transferase 1 |
| 13 | 1437671_x_at | -6.76 | Prss23 | 76453 | protease, serine, 23 |
| 14 | 1450857_a_at | -6.55 | Col1a2 | 12843 | collagen, type I, alpha 2 |
| 15 | 1423110_at | -6.45 | Col1a2 | 12843 | collagen, type I, alpha 2 |
| 16 | 1417461_at | -6.33 | Cap1 | 12331 | CAP, adenylate cyclase-associated protein 1 (yeast) |
| 17 | 1426598_at | -6.23 | Uty | 22290 | ubiquitously transcribed tetratricopeptide repeat gene, Y chromosome |
| 18 | 1439757_s_at | -6.02 | Epha4 | 13838 | Eph receptor A4 |
| 19 | 1452384_at | -5.96 | Enpp3 | 209558 | ectonucleotide pyrophosphatase/phosphodiesterase 3 |
| 20 | 1417462_at | -5.72 | Cap1 | 12331 | CAP, adenylate cyclase-associated protein 1 (yeast) |
| 21 | 1439555_at | -5.52 | Rlf | 109263 | rearranged L-myc fusion sequence |
| 22 | 1433542_at | -5.44 | Inpp5f | 101490 | inositol polyphosphate-5-phosphatase F |
| 23 | 1451260_at | -5.18 | Aldh1b1 | 72535 | aldehyde dehydrogenase 1 family, member B1 |
| 24 | 1460616_at | -5.11 | Slco4c1 | 227394 | solute carrier organic anion transporter family, member 4C1 |
| 25 | 1433783_at | -5.07 | Ldb3 | 24131 | LIM domain binding 3 |
| 26 | 1425538_x_at | -4.56 | Ceacam1 | 26365 | carcinoembryonic antigen-related cell adhesion molecule 1; carcinoembryonic a |
| 27 | 1432075_a_at | -4.49 | Tekt1 | 21689 | tektin 1 |
| 28 | 1431057_a_at | -4.47 | Prss23 | 76453 | protease, serine, 23 |
| 29 | 1416008_at | -4.24 | Satb1 | 20230 | special AT-rich sequence binding protein 1 |
| 30 | 1448123_s_at | -4.16 | Tgfbi | 21810 | transforming growth factor, beta induced |
| 31 | 1421929_at | -4.10 | Epha4 | 13838 | Eph receptor A4 |
| 32 | 1426108_s_at | -4.09 | Cacnb1 | 12295 | calcium channel, voltage-dependent, beta 1 subunit |
| 33 | 1423505_at | -4.05 | Tagln | 21345 | transgelin |
| 34 | 1435836_at | -3.90 | Pdk1 | 228026 | pyruvate dehydrogenase kinase, isoenzyme 1 |
| 35 | 1427630_x_at | -3.74 | Ceacam1 | 26365 | carcinoembryonic antigen-related cell adhesion molecule 1; carcinoembryonic a |
| 36 | 1438403_s_at | -3.72 | Malat1 | 72289 | metastasis associated lung adenocarcinoma transcript 1 (non-coding RNA) |
| 37 | 1429509_at | -3.72 | Lsm12 | 268490 | LSM12 homolog (S. cerevisiae) |
| 38 | 1449071_at | -3.69 | Myl7 | 17898 | myosin, light polypeptide 7, regulatory |
| 39 | 1421100_a_at | -3.62 | Dab1 | 13131 | disabled homolog 1 (Drosophila) |
| 40 | 1418188_a_at | -3.52 | Malat1 | 72289 | metastasis associated lung adenocarcinoma transcript 1 (non-coding RNA) |
| 41 | 1420989_at | -3.51 | 4933411K20Rik | 66756 | RIKEN cDNA 4933411K20 gene |
| 42 | 1418189_s_at | -3.50 | Malat1 | 72289 | metastasis associated lung adenocarcinoma transcript 1 (non-coding RNA) |
| 43 | 1423162_s_at | -3.45 | Spred1 | 114715 | sprouty protein with EVH-1 domain 1, related sequence |
| 44 | 1418617_x_at | -3.44 | Clgn | 12745 | calmegin |
| 45 | 1423184_at | -3.35 | Itsn2 | 20403 | intersectin 2 |
| 46 | 1444616_x_at | -3.33 | | | C-type lectin domain family 2, member e |
| 47 | 1434447_at | -3.25 | Met | 17295 | met proto-oncogene |
| 48 | 1450494_x_at | -3.24 | Ceacam1 | 26365 | carcinoembryonic antigen-related cell adhesion molecule 1; carcinoembryonic a |
| 49 | 1424130_a_at | -3.23 | Ptrf | 19285 | polymerase I and transcript release factor |
| 50 | 1429021_at | -3.23 | Epha4 | 13838 | Eph receptor A4 |

FIG. 17 continued

| | Probe Set ID | Fold change | Gene Symbol | Entrez Gene | Gene Description |
|---|---|---|---|---|---|
| 51 | 1417780_at | -3.21 | Lass4 | 67260 | LAG1 homolog, ceramide synthase 4 |
| 52 | 1427311_at | -3.17 | Bptf | 207165 | bromodomain PHD finger transcription factor |
| 53 | 1416612_at | -3.17 | Cyp1b1 | 13078 | cytochrome P450, family 1, subfamily b, polypeptide 1 |
| 54 | 1417141_at | -3.16 | Igtp | 16145 | interferon gamma induced GTPase |
| 55 | 1456120_at | -3.15 | Secisbp2l | 70354 | SECIS binding protein 2-like |
| 56 | 1429778_at | -3.12 | Optn | 71648 | optineurin |
| 57 | 1427998_at | -3.10 | Lsm12 | 268490 | LSM12 homolog (S. cerevisiae) |
| 58 | 1435679_at | -3.08 | Optn | 71648 | optineurin |
| 59 | 1421129_a_at | -3.05 | Atp2a3 | 53313 | ATPase, Ca++ transporting, ubiquitous |
| 60 | 1458539_at | -2.95 | R3hdm1 | 226412 | R3H domain 1 (binds single-stranded nucleic acids) |
| 61 | 1457936_at | -2.93 | Mapk8 | 26419 | mitogen-activated protein kinase 8 |
| 62 | 1439882_at | -2.92 | Sec23ip | 207352 | Sec23 interacting protein |
| 63 | 1424598_at | -2.87 | Ddx6 | 13209 | DEAD (Asp-Glu-Ala-Asp) box polypeptide 6 |
| 64 | 1450647_at | -2.87 | Hps3 | 12807 | Hermansky-Pudlak syndrome 3 homolog (human) |
| 65 | 1438200_at | -2.87 | Sulf1 | 240725 | sulfatase 1 |
| 66 | 1450839_at | -2.85 | D0H4S114 | 27528 | DNA segment, human D4S114 |
| 67 | 1429183_at | -2.84 | Pkp2 | 67451 | plakophilin 2 |
| 68 | 1447680_at | -2.83 | Anp32e | 66471 | acidic (leucine-rich) nuclear phosphoprotein 32 family, member E |
| 69 | 1456697_x_at | -2.80 | Dmtf1 | 23857 | cyclin D binding myb-like transcription factor 1 |
| 70 | 1440146_at | -2.78 | Vps13a | 271564 | vacuolar protein sorting 13A (yeast) |
| 71 | 1450068_at | -2.77 | Baz1b | 22385 | bromodomain adjacent to zinc finger domain, 1B |
| 72 | 1417220_at | -2.76 | Fah | 14085 | fumarylacetoacetate hydrolase |
| 73 | 1424657_at | -2.74 | Taok1 | 216965 | TAO kinase 1 |
| 74 | 1448300_at | -2.73 | Mgst3 | 66447 | microsomal glutathione S-transferase 3 |
| 75 | 1449799_s_at | -2.72 | Pkp2 | 67451 | plakophilin 2 |
| 76 | 1433809_at | -2.70 | Ddx5 | 13207 | DEAD (Asp-Glu-Ala-Asp) box polypeptide 5; predicted gene 12183 |
| 77 | 1458332_x_at | -2.69 | Sox4 | 20677 | SRY-box containing gene 19; SRY-box containing gene 4 |
| 78 | 1418197_at | -2.66 | Ucp1 | 22227 | uncoupling protein 1 (mitochondrial, proton carrier) |
| 79 | 1436319_at | -2.65 | Sulf1 | 240725 | sulfatase 1 |
| 80 | 1452330_a_at | -2.63 | Mxra8 | 74761 | matrix-remodelling associated 8 |
| 81 | 1427456_at | -2.63 | Wdfy3 | 72145 | WD repeat and FYVE domain containing 3 |
| 82 | 1436311_at | -2.61 | Gemin5 | 216766 | gem (nuclear organelle) associated protein 5 |
| 83 | 1437117_at | -2.61 | Centb1 | 216859 | centaurin, beta 1 |
| 84 | 1430240_a_at | -2.60 | Clgn | 12745 | calmegin |
| 85 | 1443778_at | -2.57 | Sox4 | 20677 | SRY-box containing gene 19; SRY-box containing gene 4 |
| 86 | 1424703_at | -2.53 | Hemk1 | 69536 | HemK methyltransferase family member 1 |
| 87 | 1423066_at | -2.53 | Dnmt3a | 13435 | DNA methyltransferase 3A |
| 88 | 1416105_at | -2.52 | Nnt | 18115 | nicotinamide nucleotide transhydrogenase |
| 89 | 1436020_at | -2.52 | Zfp828 | 101994 | zinc finger protein 828 |
| 90 | 1438708_x_at | -2.51 | Ywhab | 54401 | tyrosine 3-monooxygenase/tryptophan 5-monooxygenase activation protein, bet |
| 91 | 1448632_at | -2.50 | Psmb10 | 19171 | proteasome (prosome, macropain) subunit, beta type 10 |
| 92 | 1427261_at | -2.49 | Wwc1 | 211652 | WW, C2 and coiled-coil domain containing 1 |
| 93 | 1439150_x_at | -2.49 | Grtp1 | 66790 | GH regulated TBC protein 1 |
| 94 | 1434140_at | -2.49 | Mcf2l | 17207 | mcf.2 transforming sequence-like |
| 95 | 1453293_a_at | -2.48 | 2810408A11Rik | 70419 | RIKEN cDNA 2810408A11 gene |
| 96 | 1421005_at | -2.48 | Cep110 | 26920 | centrosomal protein 110 |
| 97 | 1427231_at | -2.46 | Robo1 | 19876 | roundabout homolog 1 (Drosophila) |
| 98 | 1443787_x_at | -2.45 | Casp14 | 12365 | caspase 14 |
| 99 | 1455608_at | -2.44 | Sclt1 | 67161 | sodium channel and clathrin linker 1 |
| 100 | 1433730_at | -2.44 | Elmod2 | 244548 | ELMO domain containing 2 |
| 101 | 1439995_at | -2.41 | Nhedc2 | 97086 | Na+/H+ exchanger domain containing 2 |
| 102 | 1421928_at | -2.40 | Epha4 | 13838 | Eph receptor A4 |
| 103 | 1449311_at | -2.38 | Bach1 | 12013 | BTB and CNC homology 1 |
| 104 | 1424658_at | -2.37 | Taok1 | 216965 | TAO kinase 1 |
| 105 | 1452115_a_at | -2.36 | Plk4 | 20873 | polo-like kinase 4 (Drosophila) |

FIG. 17 continued

| | Probe Set ID | Fold change | Gene Symbol | Entrez Gene | Gene Description |
|---|---|---|---|---|---|
| 106 | 1425205_at | -2.34 | Ddx19b | 234733 | DEAD (Asp-Glu-Ala-Asp) box polypeptide 19b |
| 107 | 1427950_at | -2.34 | Rnf160 | 78913 | ring finger protein 160 |
| 108 | 1437248_at | -2.34 | 2700049A03Rik | 76967 | RIKEN cDNA 2700049A03 gene |
| 109 | 1431215_at | -2.30 | Dnajc6 | 72685 | DnaJ (Hsp40) homolog, subfamily C, member 6 |
| 110 | 1418524_at | -2.28 | Pcm1 | 18536 | pericentriolar material 1 |
| 111 | 1455604_at | -2.27 | Fzd5 | 14367 | frizzled homolog 5 (Drosophila) |
| 112 | 1443971_x_at | -2.27 | Mpp7 | 75739 | membrane protein, palmitoylated 7 (MAGUK p55 subfamily member 7) |
| 113 | 1453172_at | -2.27 | Hspa13 | 110920 | heat shock protein 70 family, member 13 |
| 114 | 1451117_a_at | -2.27 | Tom1l1 | 71943 | target of myb1-like 1 (chicken) |
| 115 | 1420410_at | -2.27 | Nr5a2 | 26424 | nuclear receptor subfamily 5, group A, member 2 |
| 116 | 1431672_at | -2.27 | 9430069I07Rik | 77358 | RIKEN cDNA 9430069I07 gene |
| 117 | 1418947_at | -2.27 | Nek3 | 23954 | NIMA (never in mitosis gene a)-related expressed kinase 3 |
| 118 | 1444749_at | -2.26 | | | apolipoprotein D |
| 119 | 1456863_at | -2.25 | Epha4 | 13838 | Eph receptor A4 |
| 120 | 1452497_a_at | -2.25 | Nfatc3 | 18021 | nuclear factor of activated T-cells, cytoplasmic, calcineurin-dependent 3 |
| 121 | 1460291_at | -2.25 | Cdk6 | 12571 | cyclin-dependent kinase 6 |
| 122 | 1419642_at | -2.24 | Purb | 19291 | purine rich element binding protein B |
| 123 | 1453562_a_at | -2.23 | Nmral1 | 67824 | NmrA-like family domain containing 1 |
| 124 | 1435155_at | -2.23 | Cgn | 70737 | cingulin; cDNA sequence BC021767 |
| 125 | 1432282_a_at | -2.23 | Tlcd2 | 380712 | TLC domain containing 2 |
| 126 | 1450093_s_at | -2.23 | Zbtb7a | 16969 | zinc finger and BTB domain containing 7a |
| 127 | 1419240_at | -2.23 | Tex14 | 83560 | testis expressed gene 14 |
| 128 | 1455905_at | -2.21 | 2610507B11Rik | 72503 | RIKEN cDNA 2610507B11 gene |
| 129 | 1449058_at | -2.21 | Gli1 | 14632 | GLI-Kruppel family member GLI1 |
| 130 | 1452670_at | -2.21 | Myl9 | 98932 | myosin, light polypeptide 9, regulatory |
| 131 | 1419350_at | -2.19 | Hook2 | 170833 | hook homolog 2 (Drosophila) |
| 132 | 1422546_at | -2.19 | Ilf3 | 16201 | interleukin enhancer binding factor 3 |
| 133 | 1430530_s_at | -2.15 | Nmral1 | 67824 | NmrA-like family domain containing 1 |
| 134 | 1416688_at | -2.15 | Snap91 | 20616 | synaptosomal-associated protein 91 |
| 135 | 1447752_x_at | -2.15 | Drg1 | 13494 | developmentally regulated GTP binding protein 1 |
| 136 | 1426753_at | -2.14 | Phf17 | 269424 | PHD finger protein 17 |
| 137 | 1454849_x_at | -2.14 | Clu /// LOC1000461 | 100046120 /// 12759 | similar to clusterin; clusterin |
| 138 | 1425608_at | -2.12 | Dusp3 | 72349 | dual specificity phosphatase 3 (vaccinia virus phosphatase VH1-related) |
| 139 | 1449126_at | -2.11 | Zfp90 | 22751 | zinc finger protein 90 |
| 140 | 1416517_at | -2.10 | Pnpla6 | 50767 | patatin-like phospholipase domain containing 6 |
| 141 | 1437224_at | -2.10 | Rtn4 | 68585 | reticulon 4 |
| 142 | 1416740_at | -2.10 | Col5a1 | 12831 | collagen, type V, alpha 1 |
| 143 | 1428835_at | -2.09 | Myh14 | 71960 | myosin, heavy polypeptide 14 |
| 144 | 1456819_at | -2.09 | Nrn1l | 234700 | neuritin 1-like |
| 145 | 1430287_s_at | -2.08 | Hemk1 | 69536 | HemK methyltransferase family member 1 |
| 146 | 1428563_at | -2.08 | Ddx10 | 77591 | DEAD (Asp-Glu-Ala-Asp) box polypeptide 10 |
| 147 | 1455998_at | -2.08 | LOC667118 | 667118 | similar to Zinc finger BED domain containing protein 4 |
| 148 | 1434279_at | -2.08 | | | Fas (TNF receptor superfamily member 6) |
| 149 | 1437213_at | -2.07 | Nudt21 | 68219 | nudix (nucleoside diphosphate linked moiety X)-type motif 21 |
| 150 | 1415973_at | -2.06 | Marcks | 17118 | myristoylated alanine rich protein kinase C substrate |
| 151 | 1434362_at | -2.06 | | | sterol O-acyltransferase 1 |
| 152 | 1458361_at | -2.05 | Dclre1c | 227525 | DNA cross-link repair 1C, PSO2 homolog (S. cerevisiae) |
| 153 | 1436302_at | -2.05 | Slc10a7 | 76775 | solute carrier family 10 (sodium/bile acid cotransporter family), member 7 |
| 154 | 1434177_at | -2.05 | Ece1 | 230857 | endothelin converting enzyme 1 |
| 155 | 1436134_at | -2.05 | Scn2b | 72821 | sodium channel, voltage-gated, type II, beta |
| 156 | 1436893_a_at | -2.05 | Mar-07 | 57438 | membrane-associated ring finger (C3HC4) 7; similar to axotrophin |
| 157 | 1428583_at | -2.04 | Nufip2 | 68564 | nuclear fragile X mental retardation protein interacting protein 2 |
| 158 | 1416610_a_at | -2.03 | Clcn3 | 12725 | chloride channel 3 |
| 159 | 1429886_at | -2.02 | Rnf160 | 78913 | ring finger protein 160 |
| 160 | 1447766_x_at | -2.01 | Limd2 | 67803 | similar to epithelial protein lost in neoplasm; LIM domain containing 2 |
| 161 | 1421142_s_at | -2.01 | Foxp1 | 108655 | forkhead box P1 |
| 162 | 1450644_at | -2.00 | Zfp36l1 | 12192 | zinc finger protein 36, C3H type-like 1 |

MAMMALIAN HAPLOID EMBRYONIC STEM CELLS

FIELD OF THE INVENTION

The present invention relates to a mammalian haploid embryonic stem cell and methods for the production of the mammalian haploid embryonic stem cell. In an additional aspect, the invention also relates to a cell culture comprising the mammalian embryonic haploid stem cell and a stem cell line obtainable by proliferation of the stem cell. In a further aspect, the invention relates to the use of the haploid embryonic stem cells in genetic screening.

BACKGROUND OF THE INVENTION

Genetic screening is an important tool to identify new genes or mutant alleles of known genes that underlie biological processes. Increasingly stem cells, particularly embryonic stem cells, have been used in these screens. Stem cells are characterised by two important properties, which are of value in genetic screening. Firstly, they have an ability to proliferate in an undifferentiated state for prolonged periods of time. Secondly, stem cells are pluripotent. This means that they are capable of differentiating into any cell of the mesoderm, ectoderm or endoderm. As a result, pluripotent cells can develop into any cell of the body.

It is at present however, very difficult to screen for recessive mutations in mammalian cells. The main reason is that mammalian cells are diploid, meaning that each cell has two copies of each gene. As a result, the phenotypic traits of heterozygous recessive mutations are masked by the second copy of the gene.

A solution to screen for recessive mutations is to use a haploid mammalian embryonic stem cell. Haploid stem cells are stem cells that in contrast to diploid stem cells possess only one copy of each gene. As a result, the phenotypic traits of recessive mutations are essentially unmasked, and as a result the underlying genes can be easily identified and studied.

Haploid embryonic stem cells have been obtained from fish as described in Yi and Hong (2009). In this paper, the authors developed haploid embryonic stem cell lines from the medaka fish (*Oryzias latipes*).

However, notably, at present, no such cells have been obtained from mammals and fish haploid embryonic stem cells can not be used as a substitute. Unlike placental mammals, fish are oviparous animals and have no placentation. As a result, embryonic development differs substantially from fish to mammals. Furthermore, key features such as sex determination and dosage compensation are also regulated differently and implantation, placentation and genomic imprinting are all absent in Medaka fish.

The use of a near-haploid tumour cell line for genetic screening has been described by Carette et al., (2009). In this paper, insertional mutagenesis was used to generate null alleles in a human cell line haploid for all chromosomes except chromosome 8. Therefore, the cell line described in this paper was not a true haploid. Furthermore, as the cell line carried genetic rearrangements and a transformed phenotype, its usefulness in genetic screening in developmental system is limited.

A number of reports have also found near-haploid cells in a variety of human tumours, Nonetheless, except for one case, no near-haploid cell lines have been derived from these tumours (Sukov et al., 2010).

Finally, Kaufman et al. (1983) describe the production of pluripotent cell lines from haploid embryos from parthenogenetically activated oocytes. However, the cell lines even at early passages of the cells were diploid not haploid.

Accordingly, there exists a need to produce mammalian haploid embryonic stem cells. Such cells would enable genetic screening for recessive mutations in a developmentally relevant context. For example, it is envisaged that such cells would be an important tool in identifying new genes involved in signalling pathways, developmental decisions and cell cycle regulation. Moreover, there is a need to produce haploid stem cells without tumour-derived mutations, genomic rearrangements or oncogenes. Stem cells with such characteristics are obtained when cells are derived from tumour cells. Accordingly, there exists a need to develop mammalian embryonic stem cells with a normal karyotype.

SUMMARY OF THE INVENTION

According to a first aspect of the present invention, there is provided a mammalian haploid embryonic stem cell, wherein the stem cell is pluripotent, capable of proliferation, and can maintain a haploid karyotype during proliferation in culture. After haploid ES cells have been established they can be maintained in a wide range of conditions. Haploid ES cells can be cultured in standard ES cell medium conditions usually including LIF and fetal calf serum or Knock-out serum replacement (Invitrogen; 10828028) or chemically defined media using 2i inhibitors.

In certain embodiments, the haploid ES cells appear to have a smaller size than diploid ES cells.

In a preferred aspect, the stem cell can maintain a haploid karyotype for at least 15, preferably 20, and more preferably at least 25 passages of the stem cell. A passage is the degree of subculturing of a cell.

A further aspect of the invention provides a method for the production of a mammalian embryonic stem cell, wherein the method comprises the following steps—

- activating isolated oocytes in vitro to produce haploid embryos;
- culturing the activated embryos to the 8-cell, morula or blastocyst stage;
- removing the zona pellucida;
- isolating the inner cell mass of the activated embryos; and
- further culturing the inner cell mass to derive a haploid embryonic stem cell.

The method may further comprise the step of flow sorting based on DNA content, to isolate haploid ES cells.

The in vitro activation may comprise incubation in M16 medium, strontium chloride and EGTA. In a further preferred embodiment, the incubation time is no more than 5 hours, preferably 1 to 3 hours. M16 medium may be obtained from Sigma; Cat. no. M7292. Potential other means for oocyte activation include activation with an electric pulse and by using calcium ionophores such as ionomycine.

In a further aspect, the cultured activated embryo is preferably cultured with kinase inhibitors. The kinase inhibitors may be selected from threonine/tyrosine kinase inhibitors and/or glycogen synthase kinase 3β inhibitors. In a preferred embodiment, the kinase inhibitors are PD0325901 and CHIR99021 (CHIR99021 from Stemgent Catalog #04-0004; PD0325901 from Stemgent Catalog #04-0006). The culture will typically include fibroblast feeder cells.

Other culturing methods may include:

a) High glucose DMEM medium (PAA, Cat. No. E15-009) or Knockout™ D-MEM (Invitrogen, Catalog#10829018) with 15% KnockOut™ Serum Replacement (Invitrogen, Catalog#10828028) supplemented with Glutamin (Invitrogen), beta mercapto ethanol (Sigma), penicillin-streptomycine (Invitrogen), non-essential amino acids (Invitrogen) and 500 units per milliliter recombinant mouse LIF (home made).

b) It is possible that conditions as a) but with 15% fetal calf serum (PAA) instead of 15% KnockOut™ Serum Replacement would also be effective.

Potential other culture methods which may be suitable include:

c) Serumfree medium with BMP and LIF (commercially available from Millipore, ESGRO Complete PLUS Clonal Grade Medium, Millipore Cat No. SF001-500P)

d) iSTEM media (Stem Cells, Inc, Cat. No. SCS-SF-ES-01), this is a commercial formulation of the 2i media but does not contain LIF.

e) A combination of 2i culture conditions and KnockOut™ Serum Replacement (Invitrogen) such as the one used in Hanna et al, 2010, PNAS, 107(20):9222-9227

The zona pellucida is preferably removed using acidic Tyrode's solution (Millipore; MR-004-D). Oocytes are incubated in Acidic Tyrode's solution until zona pellucida is dissolved. This usually takes 30 seconds up to one minute.

In a further aspect, the trophectoderm layer of the blastocyst is preferably removed using specific antibodies (immunosurgery) prior to isolation of the inner cell mass. For example, after removal of the zona embryos are incubated with Anti-Mouse Serum antibody produced in rabbit (Sigma, M5774). After washing the trophectoderm layer is lysed using complement (rat serum, home made or commercial such as Complement sera from guinea pig, Sigma S1639). Immunosurgery is not required when ES cells are derived using 2i conditions. The procedure is described in Manipulating the Mouse Embryo, A LABORATORY MANUAL, Second Ed., Hogan, B. et al., 1994, Cold Spring Harbour Laboratory Press, ISBN 0-87969-384-3).

The cells of the inner cell mass may be cultured using either fibroblast feeders in serum-free media, cytokines and kinase inhibitors or using high glucose media supplemented with serum or a serum replacement and cytokines. In a more preferred aspect, the serum-free media is N2B27 medium. The cytokine is preferably LIF (Leukemia Inhibitory Factor). In another embodiment the high glucose media is DMEM and the serum replacement is KnockOut™ Serum Replacement (KSR).

Cell growth may be monitored by microscopy and cell clumps are dissociated using trypsin (0.25%, Invitrogen; 15090046) or Accutase (Invitrogen; A110501). The inner cell mass outgrowth and embryonic stem cells grow as a colony morphology. Haploid embryonic stem cells are obtained when many colonies are obtained in the culture dish which grow rapidly. The cells are passaged every 3 to 4 days, or every 2 to 3 days when growth speeds up. We believe that haploid ES cells are already present at the first passage, but it takes about 4 to 5 passages to expand haploid ES cells from a single ICM to a confluent 6 well sized dish with about $3\times10^6$ cells.

Haploid stem cells may be further be enriched from the culture using cell sorting. Preferably, living cells are stained. Any type of cellular DNA stain may be used. Preferably, the stain may be a fluorescent stain such as a Hoechst stain (Hoechst 33342 at a concentration of 1 microgram per milliliter). Haploid cells can be sorted using a cell sorter, preferably a fluorescence-activated cell sorter. Potential other DNA stains include VYBRANT® DYECYCLE™ STAINS for living cells (Invitrogen, Molecular probes), DRAQ5® (4084, Cell Signaling Technology) and Nuclear-ID™ Red DNA Stain (ENZ-52406, ENZO LIFE SCIENCES INTERNATIONAL, INC.) Other enrichment methods may include separation by cell size such as elutriation or subcloning from single cells.

An additional aspect of the invention provides a cell culture comprising the mammalian haploid embryonic stem cells. The culture conditions for maintaining haploid ES cells include all conditions for derivation (above). Culture in DMEM with 15% serum and LIF has also been successful for maintaining haploid ES cells.

A further aspect of the invention provides a mammalian haploid embryonic stem cell line obtained by proliferation of the mammalian embryonic stem cell. The embryonic stem cell line is pluripotent, capable of proliferation and has a stable haploid karyotype during proliferation.

Another aspect of the invention provides the use of the mammalian embryonic stem cell line in genetic screening. In a preferred embodiment, the genetic screen is a genetic forward screen. We have successfully performed a forward genetic screen in the haploid ES cells as follows. A pool of haploid ES cells is exposed to a mutagen such as an insertional vector. Cells containing mutations can be selected for example using a selection marker of the insertional mutagen. The pool of mutant haploid cells can optionally now be diploidized as mutations will be in a homozygous configuration. Selection of desired mutations can be achieved by appropriate metabolic conditions, reporter genes combined with cell sorting or by phenotypic characteristics including cell adhesion and cell surface markers. We have performed a pilot screen as a proof of principle experiment for genes involved in the mismatch repair pathway. In this screen a Piggybac transposon derived vector was used as the insertional mutagen. Selection for cells with mutations in genes required for mismatch repair was achieved using 2-amino-6-mercaptopurine (Sigma, 6-TG), a substance that is toxic to cells proficient in mismatch repair. The gene mutations were identified by a Splinkerette PCR strategy. This screen identified the two known autosomal mismatch repair genes Msh2 and Fanci (see below) and demonstrates the principle application of haploid mouse ES cells for genetic screening.

Potential other mutagens include: a) Genetrap vectors such as attenuated viruses; b) Chemical mutagens; c) Physical methods for mutagenesis such as ionizing irradiation.

Potential other methods for identifying mutations include: a) Reporter gene activity combined with cell sorting; b) Reporter gene activity combined with antibiotic resistance; c) Cell surface molecules combined with appropriate methods for cell isolation such as antibody based; d) Metabolic conditions; e) Exposure to biological agents such as pathogens for instance for identifying host cell factors or receptors for viruses.

Potential other methods for gene identification include: a) 5 prime race for identification of trapped genes; b) Genome wide expression profiling; c) DNA sequencing; d) directed screening for mutations in specific genes or gene sets such as by DNA sequencing or PCR.

A benefit of using mouse ES cells is the availability of a large number of genetic modifications that have been introduced into the mouse genome and specific mutations can be readily generated. Therefore, genetic modification of haploid ES cell lines or derivation of haploid ES cells lines from genetically modified mouse strains can be utilized to enable complex screens or make screens more specific. Potential uses are (1) the incorporation of sensitizing mutations for finding synthetic lethal combinations of genes for uncovering parallel or redundant pathways and (2) the introduction of appropriate selection markers such as reporter genes for pathway activity that enable or support the isolation of desired mutations.

Potential other uses for haploid ES cells include:

a) Haploid ES cells can be introduced into mice. One way of doing this is by diploidizing them in culture to obtain parthenogenetic diploid ES cells. These can be introduced via blastocyst injection, morula aggregation or 8-cell injection into chimeric mice. Germline transmission of parthenogenetic mouse ES cells has been reported and presents a route for introducing mutations identified in a screen into mice for further study.

b) Haploid ES cells can be used for cell fusion. Two different haploid cells can be combined to give a diploid cell. Similarly, triploid cells result from fusion of a haploid ES cell with a diploid cell. Potential partners for fusion with haploid ES cells are other haploid ES cells for instance to combine two genetic modifications. This could be useful for testing genetic interactions. Other potential applications could be the fusion of naturally haploid cells such as gametes with haploid ES cells to derive diploid cells.

c) Haploid ES cells can be used to derive differentiated cells. Haploid ES cells can differentiate but in the course of differentiation they mostly become diploid.

In a preferred aspect, the mammal is a rodent, preferably a mouse (*Mus musculus*). In a more preferred aspect, the strain of the mouse is CBA/B6. However, a number of different strains of mouse can be used. This would allow different genetic modifications to be introduced, such as selectable marker genes.

Potential other mouse strains include:

a) inbred mouse strains such as 129Sv or C57/BL6 b) outbred mouse strains—We have successfully derived haploid ES cells from a mixed background containing a genetic modification of the Xist gene locus (Xist2LOX).

c) Genetically modified mouse strains such as strains carrying gene deletions or transgenes. Especially, mouse strains containing reporter genes (including antibiotic resistance or GFP) such as Oct4 or Rex1 promoter driven GFP reporter strains could be used for screening. In addition reporters for cell signalling pathways could be introduced from the mouse strain such as a TOPflash reporter for Wnt signalling pathway activity. In addition mutations for sensitizing the genetic background can be introduced by deriving haploid ES cells from mice carrying gene deletions. An important aspect of haploid mouse ES cells is the ability to realize the potential of a large number of preexisting mouse mutations that could be utilized to screen for specific components in mammalian signaling, cell cycle, and metabolic pathways.

ES cells with similar properties as mouse ES cells have been described from rats and rabbits (Telugu et al, 2010, The International Journal of Developmental Biology 54: 1703-1711). The method of the present invention could be applied to these mammals.

BRIEF DESCRIPTION OF THE DRAWINGS

The present invention will now be described, by way of example only, with reference to the accompanying drawings, in which

FIGS. 2A and 2B show the characterisation of a haploid mouse embryonic stem (ES) cell line. FIG. 2A shows three representative pictures of metaphase spreads of a haploid mouse ES cell line showing a haploid set of 20 chromosomes. DNA was stained with DAPI. FIG. 2B shows a FACS analysis of fixed ES cells after DNA staining with propidium iodide. Position of haploid (1n), diploid (2n), and tetraploid (4n) DNA content is indicated. The haploid line (upper panel) shows a predominantly 1n DNA content with some G2 cells after DNA replication showing as 2n. The contamination with diploid cells is low as judged from the 4n peak corresponding to G2 cells. A diploid control ES cell line (lower panel) shows a 2n G1 peak and a 4n G2 peak.

FIG. 3 shows immunofluorescence staining of haploid and control diploid ES cells for detecting Nanog, a marker of pluripotent ES cells, and Gata4, an early ES differentiation marker. Colonies of both haploid and control diploid ES cells express the pluripotency marker Nanog but do not express markers that are indicative of differentiation.

(FIG. 5D) Colony morphology of haploid ESCs (HAP-1). (FIG. 5E AND 5F) Chromosome spreads of HAP-3 (FIG. 5E) and HAP-1 (FIG. 5F), (Scale bar=10 μm). (FIG. 5G) CGH analysis of HAP-1 and HAP-2 ESCs and control male CBA kidney DNA. Relative copy number is plotted at 200 kb resolution using a log 2 scale. Genomic positions indicated by blue bars (top) are enlarged at 40 kb resolution in (FIG. 5H); CBA control (black), HAP-1 (red) and HAP-2 (green).

(FIG. 6A) Immunofluorescence shows Nanog protein (red) in haploid (HAP-1) and diploid ESCs, and Gata4 (green) in differentiated cells (Scale bar=10 μm). (FIG. 6B) Expression of pluripotency markers in haploid and diploid (set to 1) ESCs by real time PCR. Error bars represent standard deviation (n=3). (FIG. 6C) Scatter plot showing log 2 transformed average expression values from gene expression profiles of 3 haploid (HAP-1, HAP-2 and HTG-1) and three diploid J1 ESC lines for 45,001 probe sets (r is the Pearson correlation coefficient; red lines indicate 2-fold up- and down-regulation). (FIG. 6D) Diagram of more than 2-fold up- and down-regulated genes in haploid ESCs.

(FIG. 7A) GFP marked haploid HAP-2 ESCs (p18) contribute to chimeric embryos at E12.5. 6 out of 9 embryos showed GFP contribution. A GFP negative embryo is shown as a control (below). (FIG. 7B) Representative flow analyses of DNA content of all cells (above) and GFP positive cells (below) extracted from a chimeric E12.5 embryo are shown. All 6 embryos gave similar results. (FIG. 7C) Live born chimeric mice were obtained from GFP marked HAP-2 ESCs. (FIG. 7D) Chimeric mice obtained from injection of HAP-1 ESCs into C57BU6 blastocysts (black) show coat colour contribution from the ESCs (agouti).

DETAILED DESCRIPTION OF THE INVENTION

Example 1

Oocyte Activation

Figure 1:
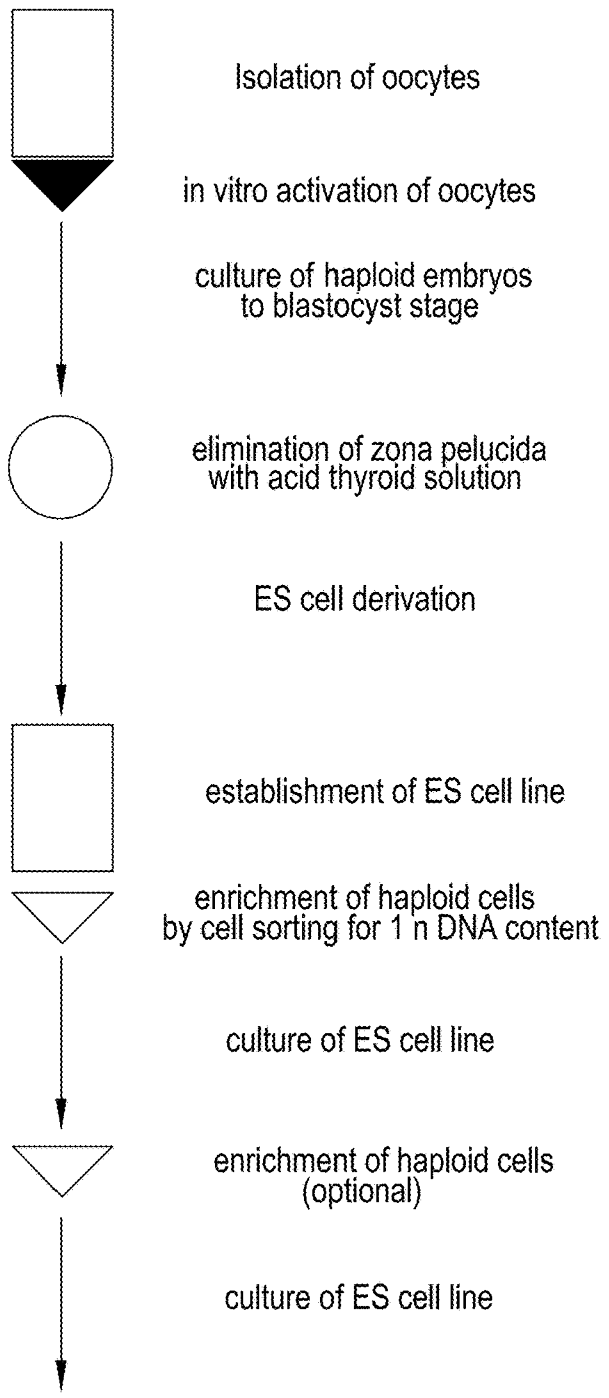
FIG. 1 shows a strategy for the derivation of the mammalian haploid embryonic stem cells.

Oocytes were isolated in the morning from mouse oviducts after hormonal induction of ovulation. Ovulation was induced by intraperitoneal injection of PMS and hCG 48 hours later (this superovulation procedure is described in Manipulating the mouse embryo, ISBN 0-87969-384-3). A potential other method for obtaining unfertilized oocytes could be through natural matings with vasectomised males.

Activation of oocytes was carried out by incubation in M16 medium to which 5 mM (millimolar) $SrCl_2$ and 2 mM EGTA were added. Incubation times of 1 to 3 hour were found to be efficient. Shorter incubation led to lower activation rates whereas 5 hour incubation appeared to affect subsequent development. After activation oocytes were cultured in groups of 50 using microdrop culture. For this 80 microliter drops of M16 medium were overlayed with mineral oil. All culture media were preequilibrated and incubation was at 37° C., 5% $CO_2$ in a tissue culture incubator (SANYO). Blastocyst stage embryos were obtained at day 3 to 4 and used for ES cell derivation.

Activation of freshly ovulated oocytes in vitro is mediated by induction of Calcium (Ca) waves. This can be achieved by prolonged culture in medium without Ca. The addition of Strontium (Sr) has been used to increase activation rates and enhance the development of diploid parthenogenetic embryos (Bianchi et al., 2010). Complexing the Ca with EGTA has made it possible to use preformulated media in combination with Sr for efficient activation of mouse oocytes (Kishigami and Wakayama, 2007). Similar protocols are established based on permeabilization of the oocyte membrane for Ca by ionomycine treatment. These protocols are more relevant for other mammalian species including human where Sr does not lead to efficient oocyte activation.

ES Cell Derivation in Chemically Defined Medium

For derivation of ES cells in chemically defined medium 8-cell embryos were cultured for two days in M16 supplemented with the following inhibitors: 1 μM PD0325901 and 3 μM CHIR99021 (M16-2i). 2i is a composition that enhances the efficiency of ES cell line derivation and thereby reduces the number of embryos required (see, for example, Nature. 2008 May 22; 453(7194):519-23. The ground state of embryonic stem cell self-renewal. Ying QL, Wray J, Nichols J, Batlle-Morera L, Doble B, Woodgett J, Cohen P, Smith A).

This step expanded the inner cell mass of the blastocyst. The zona pellucida was then removed with acidic Tyrode's solution (Hogan et al., 1994). Optionally, the trophectoderm was removed by immunosurgery. Isolated inner cell masses or embryos were then cultured on mitotically inactivated embryonic fibroblast feeders in chemically defined N2B27 medium containing above 2i inhibitors and LIF (N2B27-2i plus LIF). LIF is a cytokine that inhibits embryonic stem cell differentiation and stimulates stem cell growth. Outgrowths were passaged repeatedly every 3 to 4 days until ES cell lines emerged. In 2i ES cell lines emerged after the first passage.

ES cell culture in defined medium with signal inhibition (Ying et al., 2008) can be used to derive ES cells from recalcitrant mouse strains (Nichols et al., 2009) and rats (Buehr et al., 2008). Recently, similar approaches have led to a culture of an embryonic stem cell state from humans that have similar properties with mouse ES cells (Hanna et al., 2010).

ES Cell Derivation in Standard Conditions

For ES cell derivation the zona pellucida was removed from morula and blastocyst stage embryos with acidic Tyrode's solution (Hogan et al., 1994). After removal of the trophectoderm by immunosurgery (Hogan et al., 1994) the inner cell mass was explanted and cultured in high glucose DMEM supplemented with fetal bovine serum or serum replacement (KSR) and LIF. Outgrowths were passaged every 3-4 days until ES cell lines were obtained.

Enrichment for Cells with 1n Content Using Cell Sorting

HOECHST 33342 stained living cells were sorted using a DAKO MoFlo high speed sorter. Cells with a haploid (1n) DNA content were selected. Diploid cell lines (2n) were used as controls. For analysis the FlowJo Flow Cytometry Analysis Software was used (Tree Star Inc.).

Additionally, ES cell lines can be subcloned.

Characterization of Haploid ES Cell Lines

DNA content was investigated by analytical FACS (Fluorescence Activated Cell Sorting). Karyotypes were identified by metaphase chromosome spreads. Haploid ES cell lines display a characteristic colony morphology and growth rate comparable to diploid mouse ES cells. In addition these cells express markers of mouse ES cells (FIG. 3).

Forward Genetic Screen to Identify Genes Involved in Mismatch Repair.

This proof of principle screen was designed according to a screen performed previously (Genome Res. 2009 April; 19(4):667-73. Epub 2009 Feb. 20. A piggyBac transposon-based genome-wide library of insertionally mutated Blm-deficient murine ES cells. Wang W, Bradley A, Huang Y).

$5\times10^6$ haploid ES cells were co-transfected with a gene trap cassette embedded in a PiggyBac vector and a vector carrying the PiggyBac transposase gene. Integration of the gene trap cassette into a transcribed locus brings a puromycin resistance cassette under control of the endogenous promoter. This allows selection for successful integration of gene trap cassettes into the genome using puromycin (Sigma; P8833) at a concentration of 2 microgram per milliliter. The pool of puromycin resistant haploid ES cells was used for further screening. Cells were seeded at a density of $1.5\times10^6$ per 15 cm plate and selection for mutations in MMR genes was performed using 2 μM, 2-amino-6-mercaptopurine (Sigma, 6-TG). Selection was initiated 24 h after plating and continued for 8d. Colonies were picked and expanded before analysis. PiggyBac integrations were mapped by Splinkerette PCR. (Mikkers, H., et al (2002) High-throughput retroviral tagging to identify components of specific signaling pathways in cancer. Nat. Genet. 32:153-159.) Results are shown in table 2.

Conclusion

The above results describe the successful production of a mouse haploid embryonic stem cell. As discussed previously, to date there has been no prior description of a mammalian haploid cell and cell line. Indeed, it was previously believed that the derivation of such cells was impossible. Moreover, the above-described methods allow haploid embryonic stem cells to be derived from unfertilised oocytes. As a result, such cells do not contain tumour derived mutations, genomic rearrangements or oncogenes. We therefore describe a means for deriving embryonic stem cells with a normal haploid karyotype. Haploid ES cells provide a platform for highly efficient forward genetic screening in mammalian cells. Further, we believe that haploid ES cells are maintained most purely if they are sorted every few passages. Haploid ES cells also have a tendency to diploidize, which could enable the generation of developmental models.

TABLE 1

| Derivation of haploid mouse ES cell lines | | | | | | |
|---|---|---|---|---|---|---|
| derivation protocol | genetic background | Oocytes activated | Nr of blastocysts | ES cell lines obtained | ES cell lines with haploid contribution | max. haploid contribution (%) |
| 2i/immuno-surgery | CBA/B6 | 132 | 30 | 27 | 6 | 40 |
| 2i | CBA/B6 | 22 | 10 | 5 | 1 | 15 |
| 2i | mixed | 50 | 32 | 3 | 3 | 60 |
| KSR/immuno-surgery | CBA/B6 | 273 | 48 | 22 | 6 | 10 |

TABLE 2

| Forward genetic screen in haploid ES cells to identify genes involved in mismatch repair | |
|---|---|
| cell line number | genes identified |
| | known MMR genes |
| 1 | Msh2 |
| 2 | Fanci |
| 3 | Msh2 |
| | novel MMR candidates or false positives |
| 4 | Zfp462, Lypd1, nlgn1, Slc44a3 |
| 5 | Acbd6, Lypd1, nlgn1 |
| 6 | Usp14, Atl1, 7SK |
| 7 | Wdr40a, Sorbs2 |

Example 2

Figure 4:
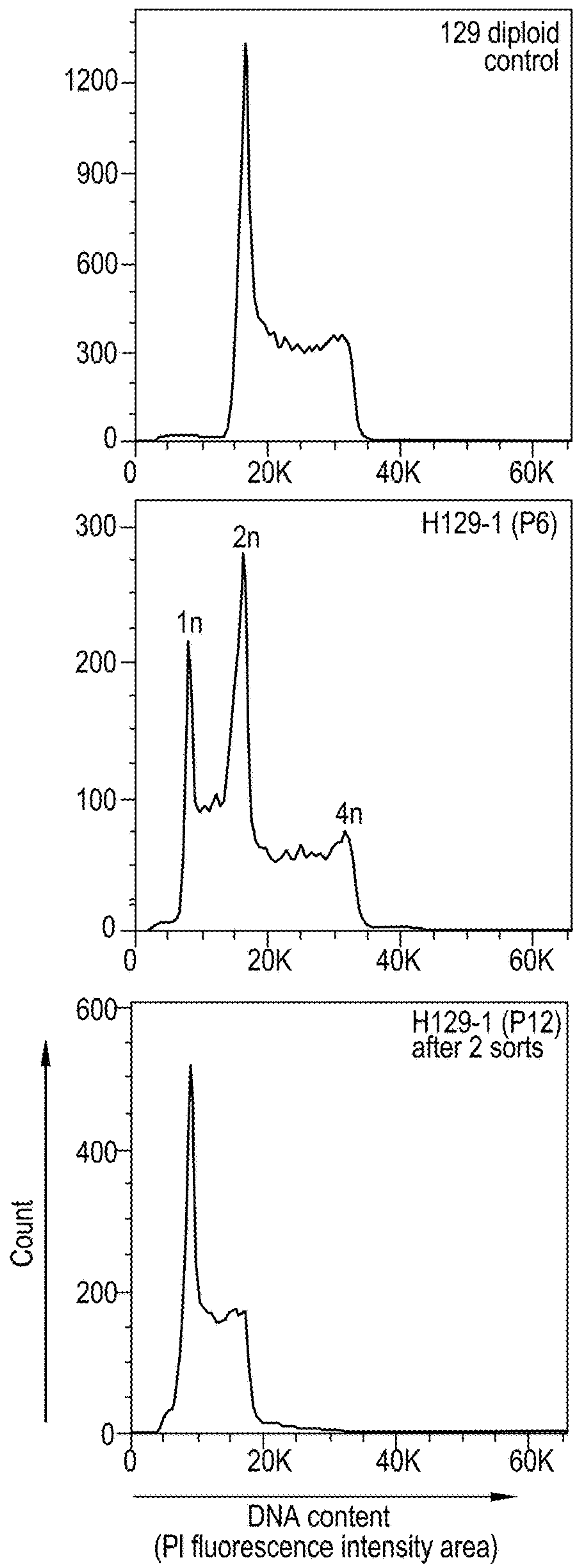
FIG. 4 shows analytic flow profiles after DNA staining with PI for 129Sv derived diploid control embryonic stem cells, the haploid H129-1 ES cell line at passage 6 and at passage 12 after two rounds of sorting the 1n peak.

Derivation of Haploid Embryonic Stem Cells from the 129Sv Inbred Mouse Strain 140 oocytes were collected from superovulated 129Sv female mice and activated using strontium chloride and EGTA in M16 medium for 2 hours. Embryos were cultured in M16 medium until the blastocyst stage. 13 blastocysts were obtained, the zona was removed and the inner cell masses were cultured in 2i medium in the presence of LIF and BSA. Form a total of 10 embryonic stem cell lines obtained, 3 showed a substantial content of cells with a haploid genome equivalent. The haploid cell content was estimated between 40% and 60%. Sorting of the haploid 1n peak allowed the establishment of pure haploid 129Sv mouse embryonic stem cells cultures. FIG. 4 shows analytic flow profiles after DNA staining with PI for 129Sv derived diploid control embryonic stem cells, the haploid H129-1 ES cell line at passage 6 and at passage 12 after two rounds of sorting the 1n peak.

Example 3

Most animals are diploid but haploid-only and male-haplo species have been described[1]. Diploid genomes of complex organisms limit genetic approaches in biomedical model species such as in mice. To overcome this problem experimental induction of haploidy has been used in fish[2,3]. In contrast, haploidy appears less compatible with development in mammals[4,5]. Here we describe haploid mouse embryonic stem cells and show their application in forward genetic screening.

Experimentally induced haploid development in zebrafish has been utilized for genetic screening[2]. Recently, haploid pluripotent cell lines from medaka fish have also been established[3]. In contrast to fish, haploidy is not compatible with development in mammals. Although haploid cells have been observed in egg cylinder stage parthenogenetic mouse embryos[6] the majority of cells in surviving embryos become diploid. Previous attempts to establish pluripotent stem cell lines from haploid embryos have resulted in the isolation of parthenogenetic embryonic stem cells (ESCs) with a diploid karyotype[4]. These studies reported the development of apparently normal haploid mouse blastocysts with a defined inner cell mass (ICM)[4,5]. In order to investigate the haploid ICM, we cultured haploid mouse blastocysts in chemically defined medium with inhibitors of mitogen activated protein kinase kinase (MEK) and glycogen synthase kinase 3 (GSK3). This 2i medium[7] has previously been used for isolating ESCs from recalcitrant mouse strains[8] and rats[9] and may help to maintain certain characteristics of early mouse epiblast cells[10,11].

Figure 5A:
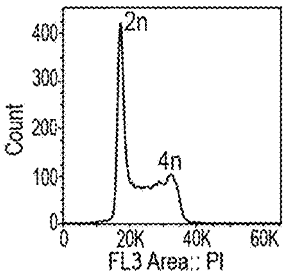
FIGS. 5A-5H show derivation of haploid ESCs. Flow analysis of DNA after PI staining of (FIG. 5A) diploid control ESCs, (FIG. 5B) haploid ESC line HAP-1 at passage 7 (p7) and (FIG. 5C) HAP-1 (p11) after sorting at p7.
Figure 5B:
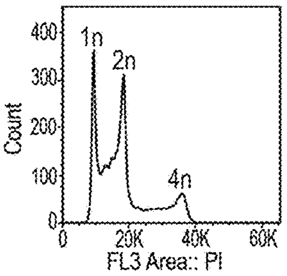
Figure 5C:
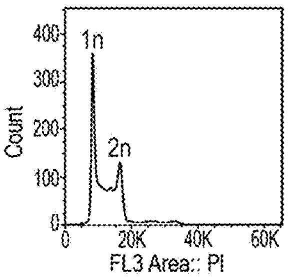

We generated haploid mouse embryos by activation of unfertilized oocytes isolated from superovulated B6CBAF1 hybrid female mice using strontium chloride. After culture in M16 medium 30 blastocysts (22%) were obtained from 132 activated oocytes and used for ESC derivation. After removal of the zona and trophectoderm, ICMs were cultured in gelatinized 96 well dishes in 2i medium in the presence of LIF. 27 ESC lines were obtained (93%). Individual ESC lines were expanded and their DNA content was analysed by flow analysis using diploid ESCs as controls (FIGS. 5A and 5B). In 6 ESC lines, at least 10% of the cells had a haploid DNA content and the proportion of haploid cells could reach a conservatively estimated 60% (FIG. 5B). Further enrichment was achieved by flow sorting of cells with a haploid DNA content after staining with HOECHST 33342 (FIG. 5C). This allowed expansion of haploid ESC lines for over 35 passages.

Figure 8A:
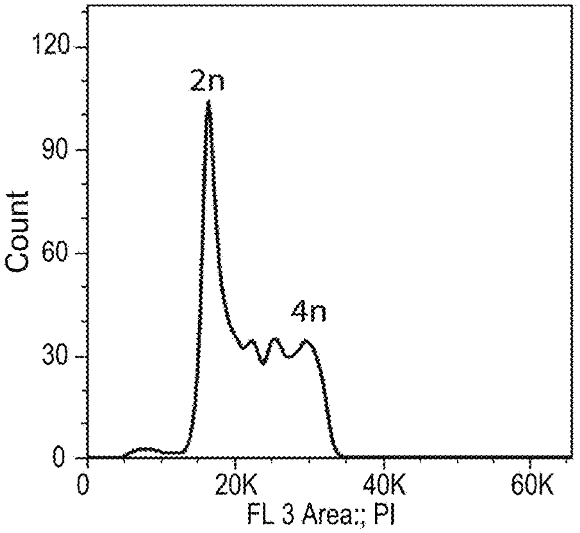
Figure 8B:
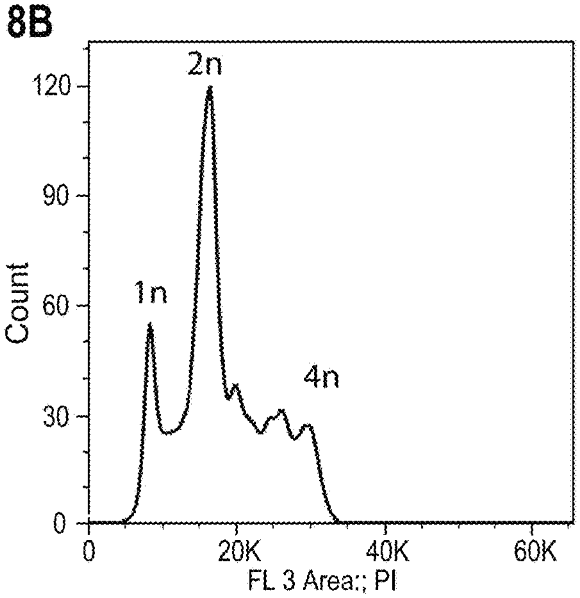
Figure 9A:
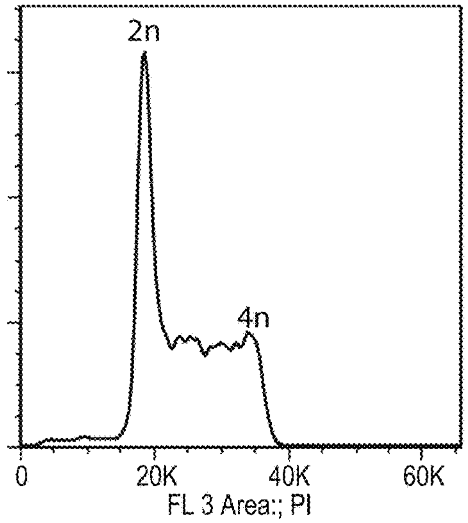
Figure 9B:
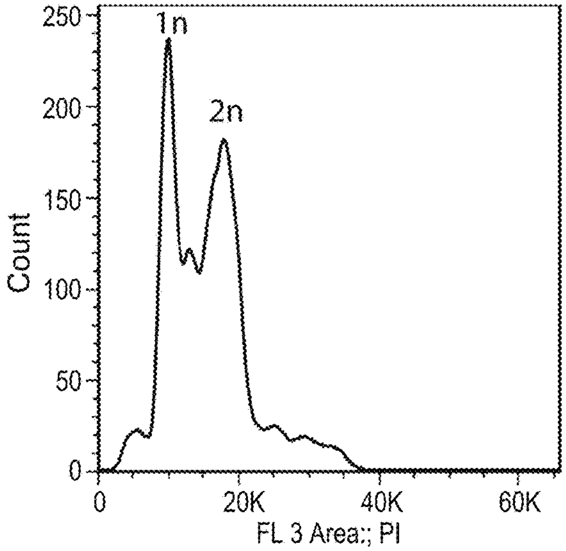
Figure 11:
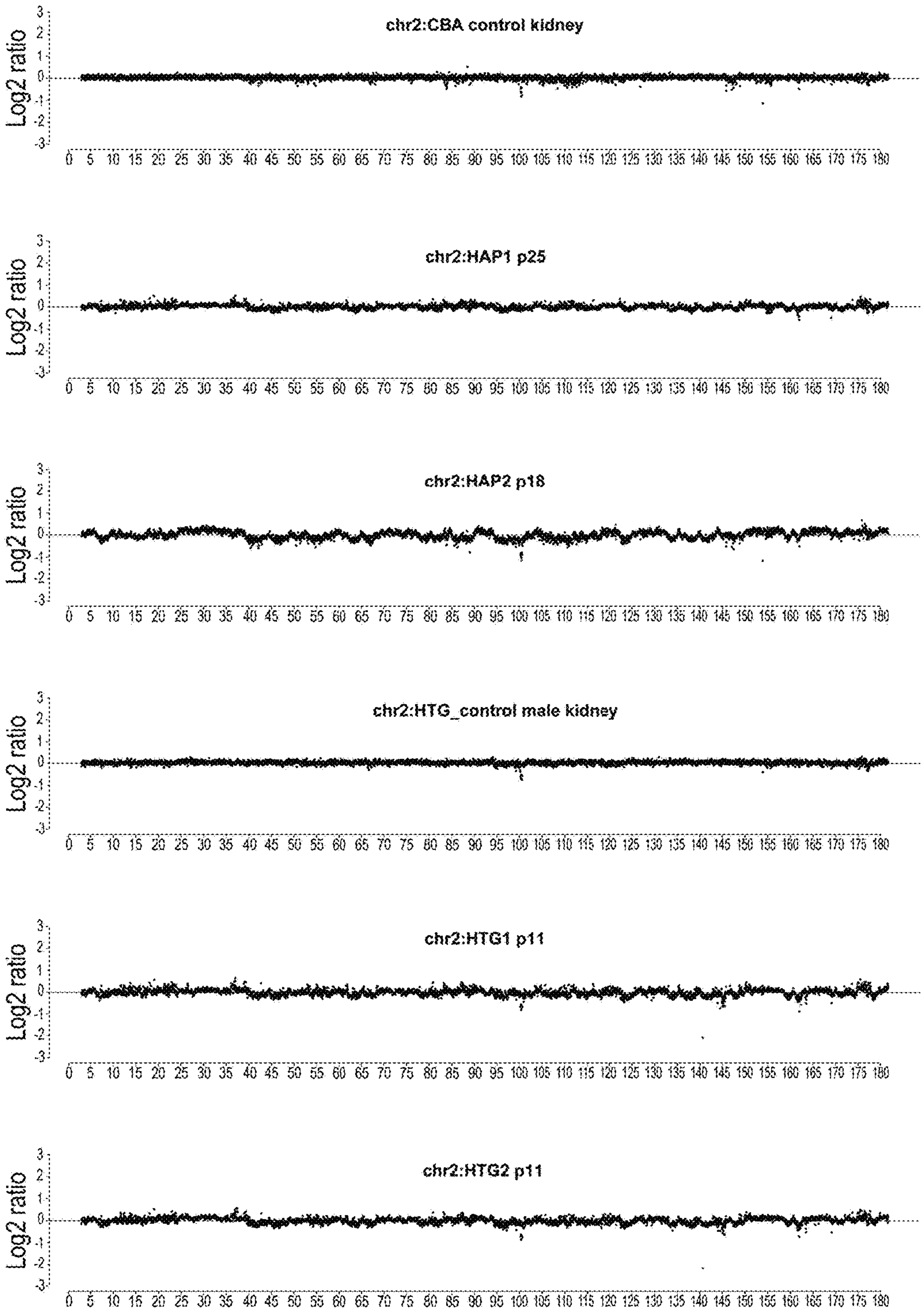
Figure 11:
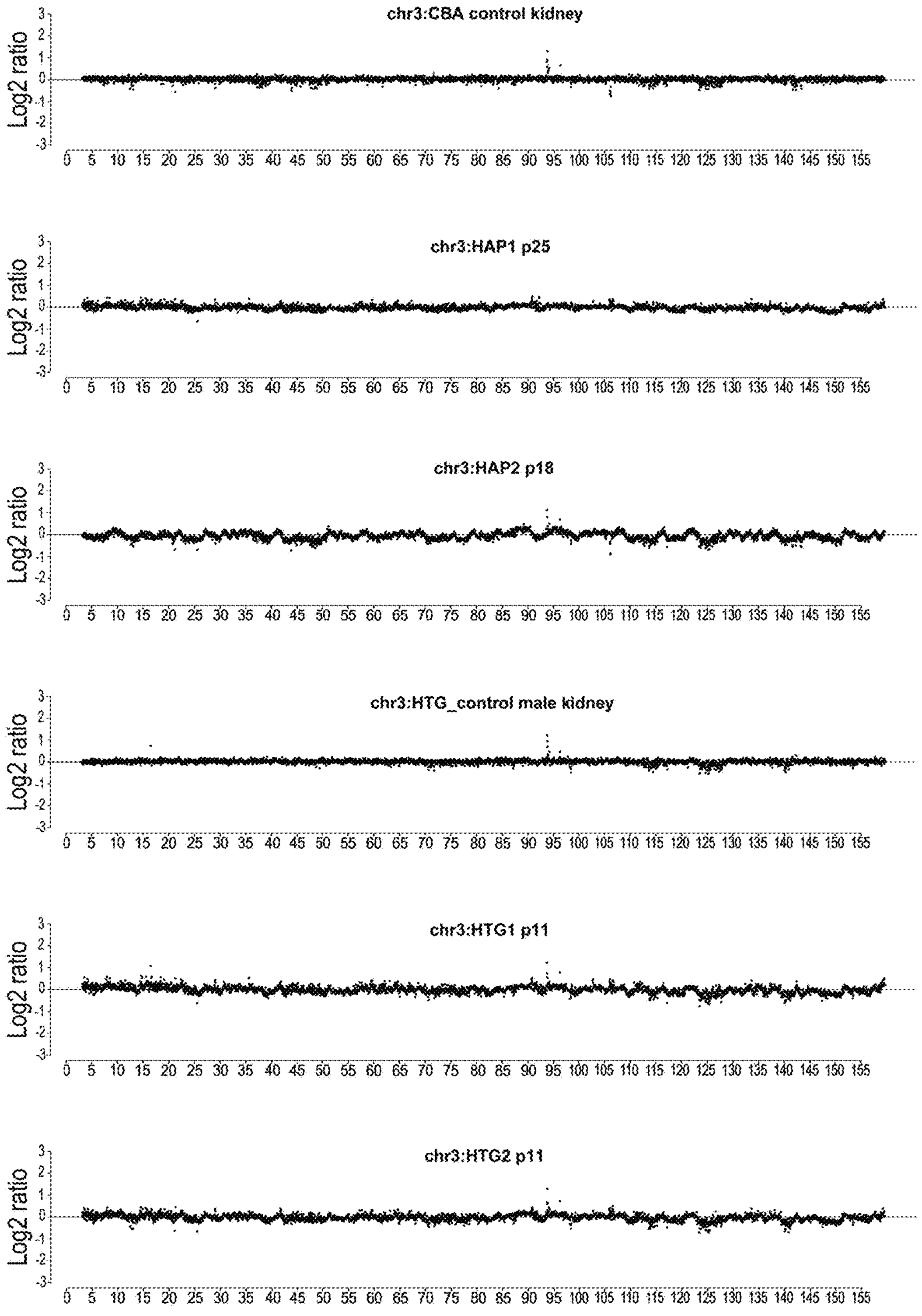
Figure 11:
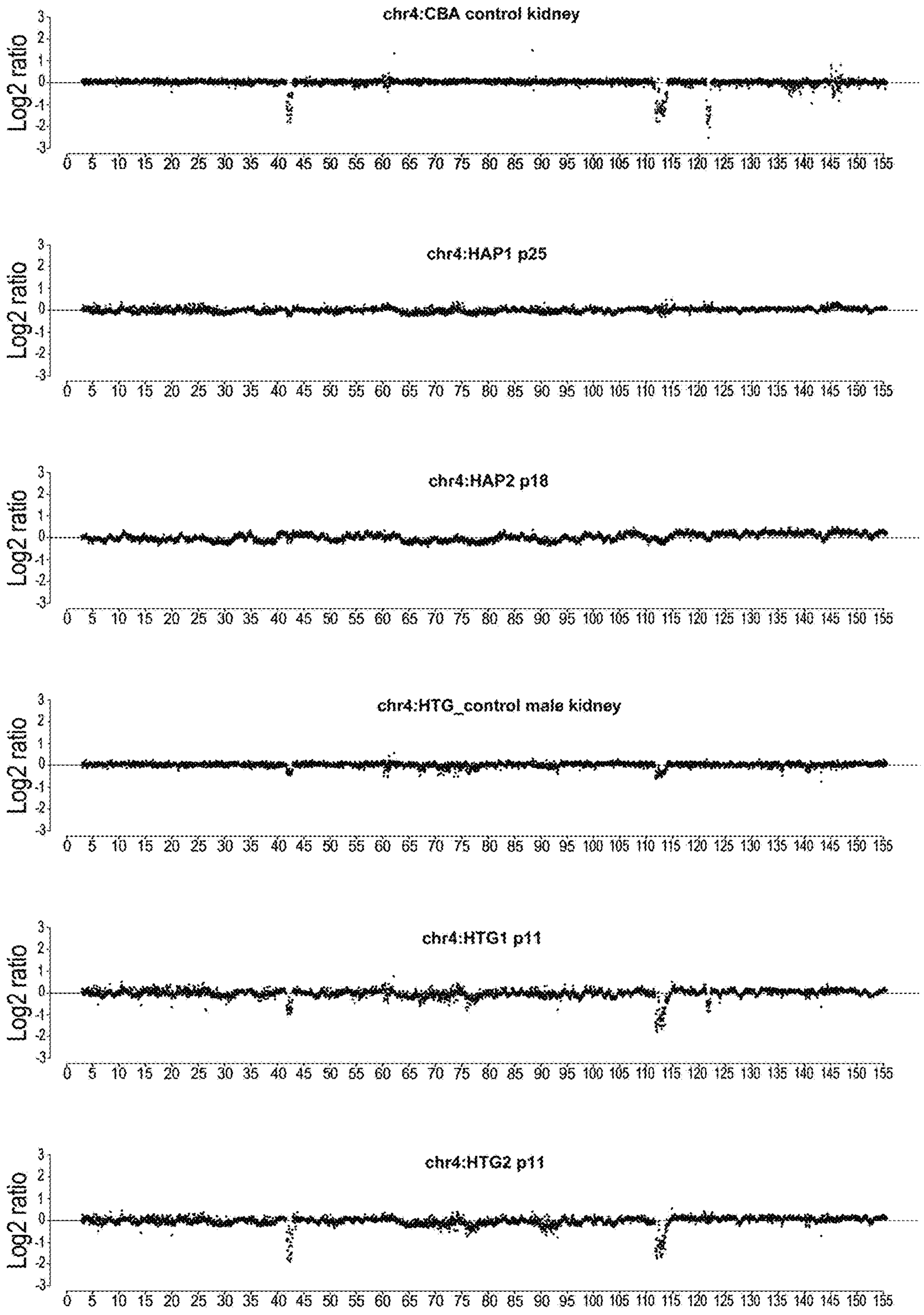
Figure 11:
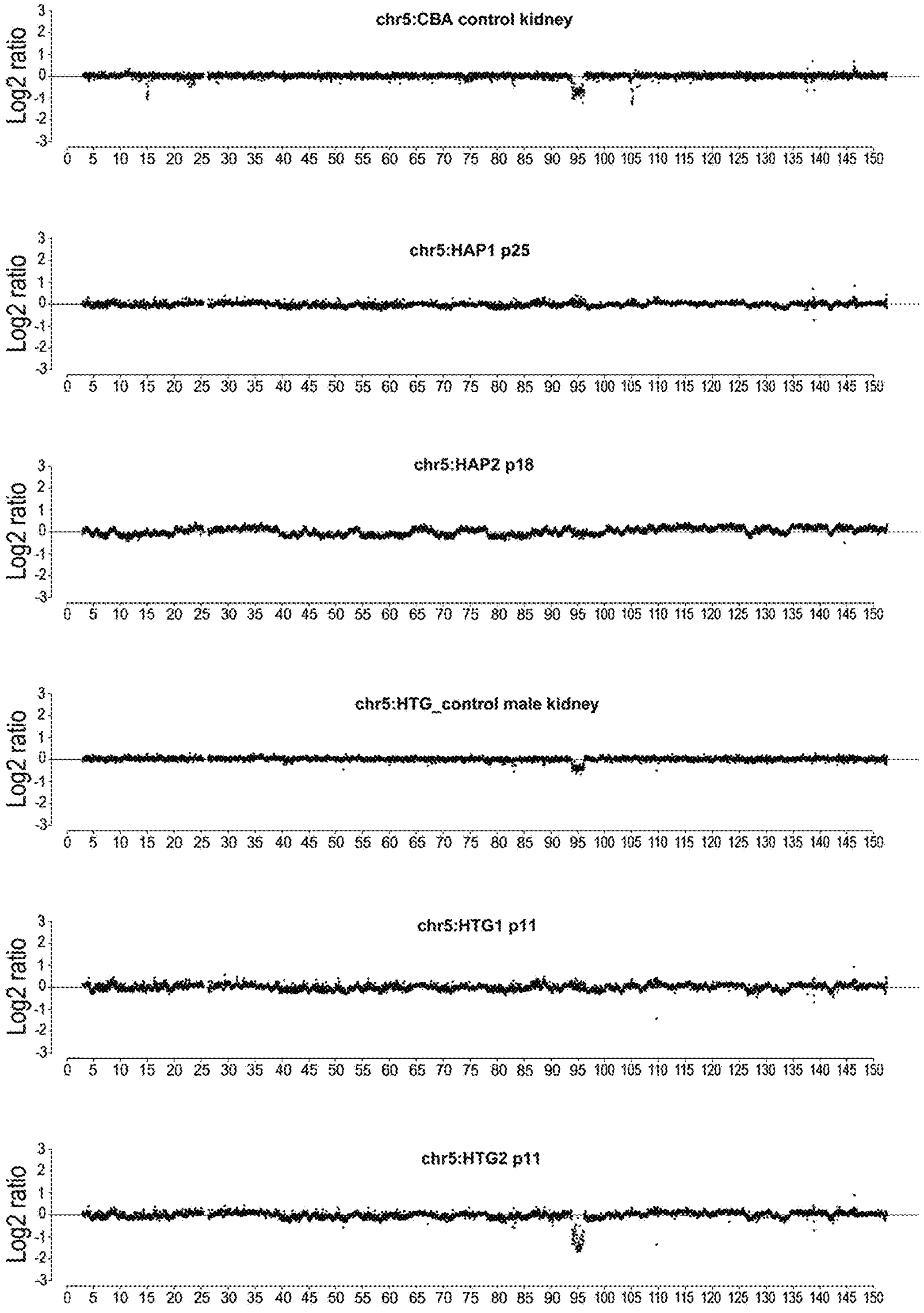
Figure 11:
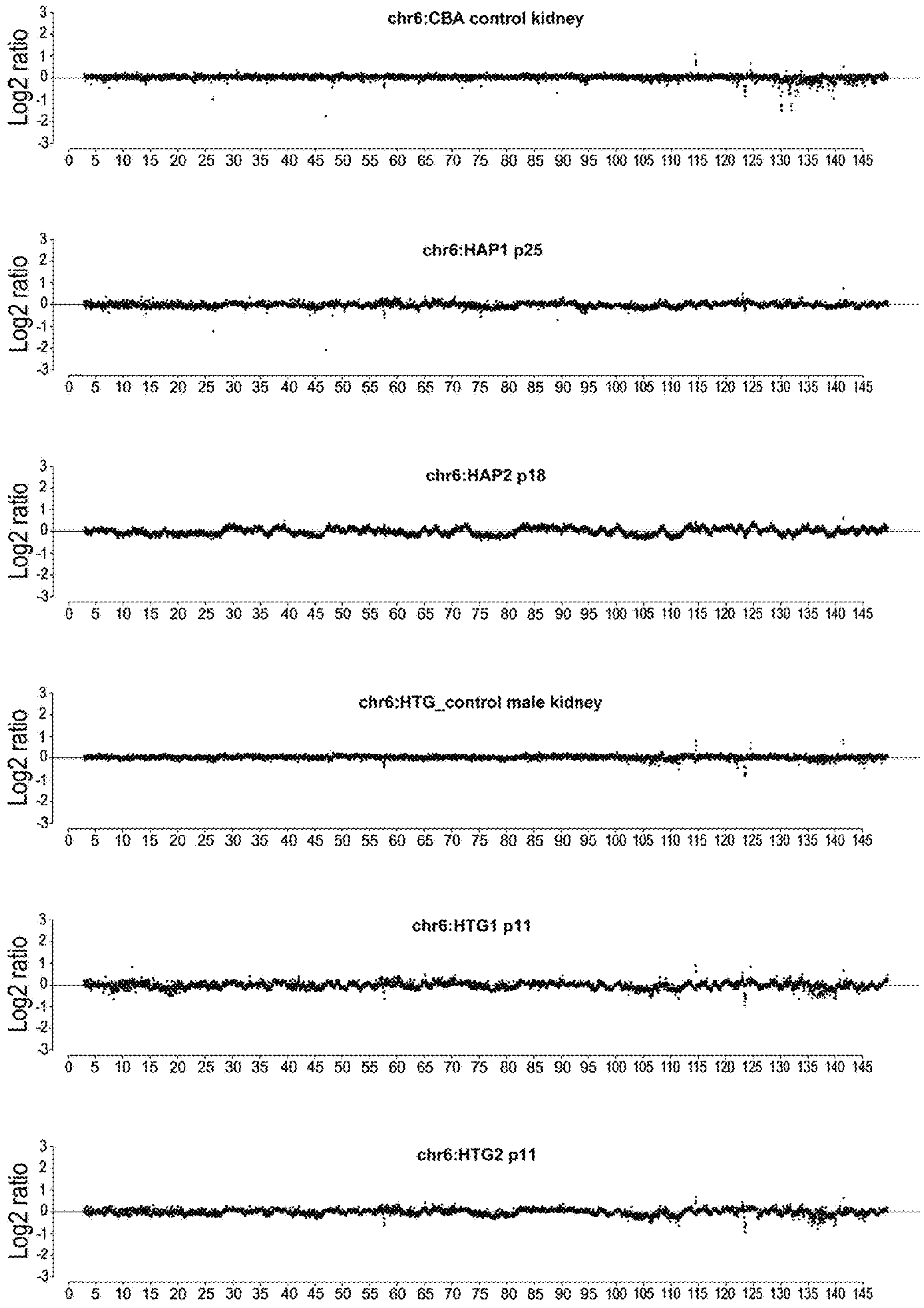
Figure 11:
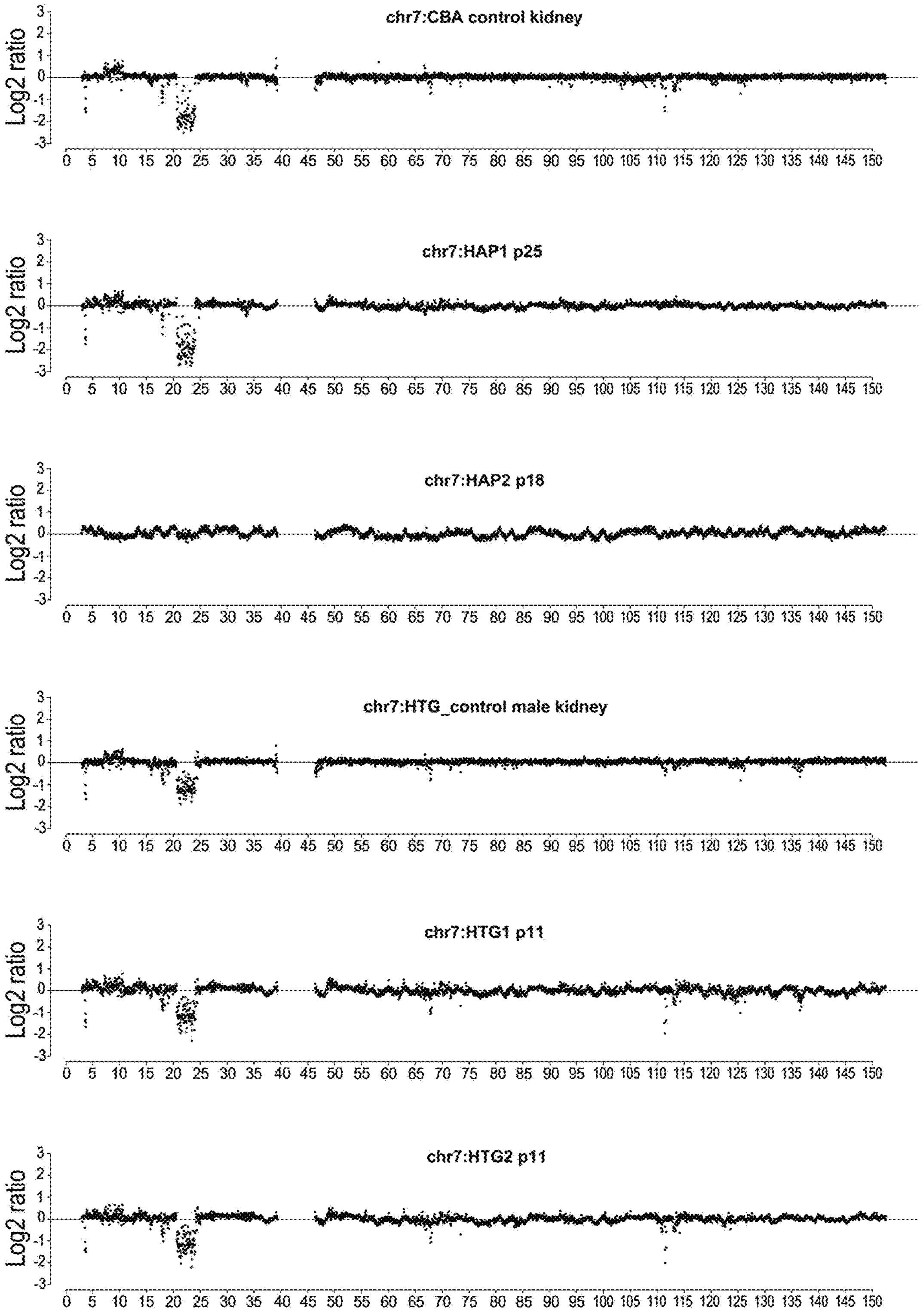
Figure 11:
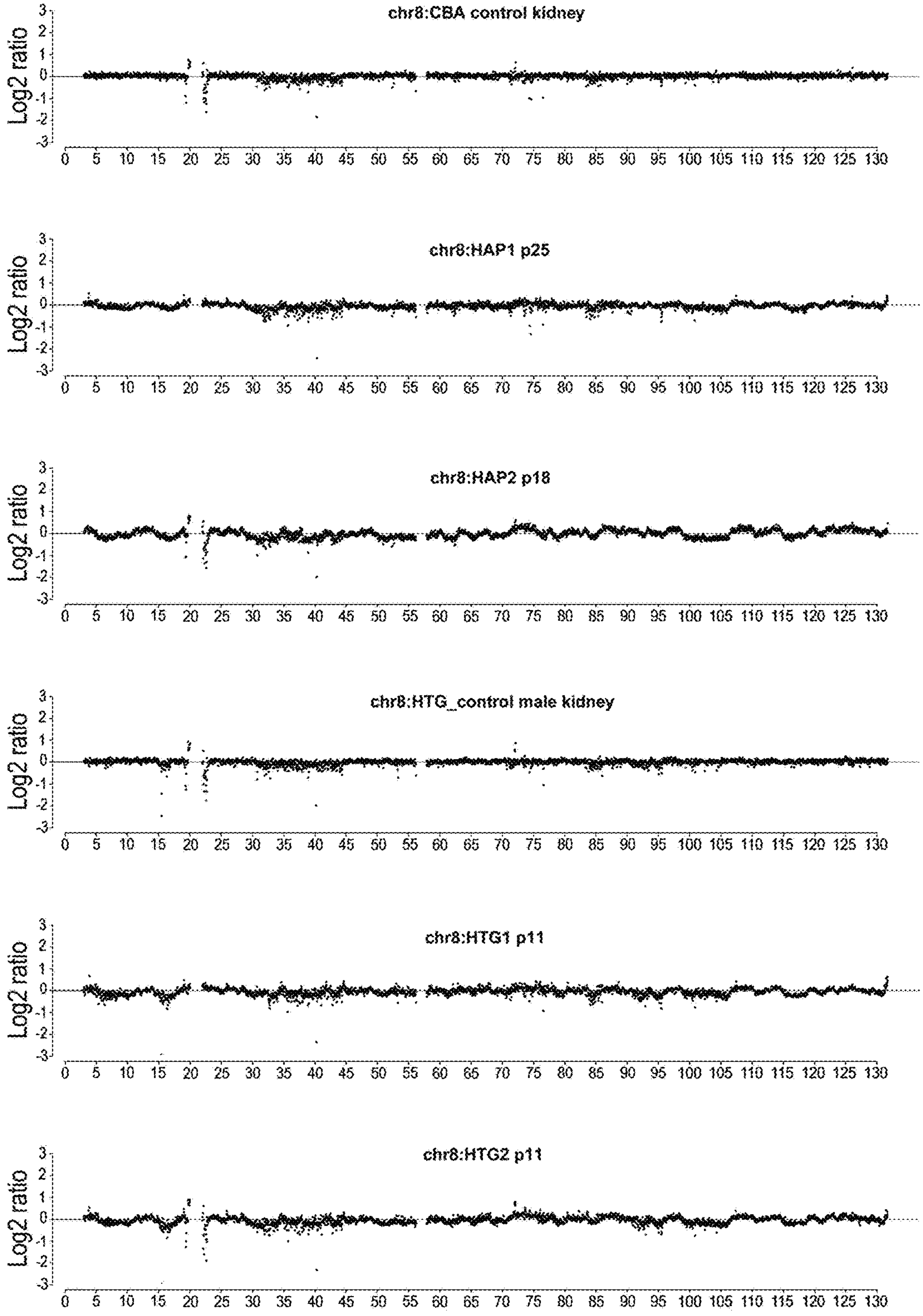
Figure 11:
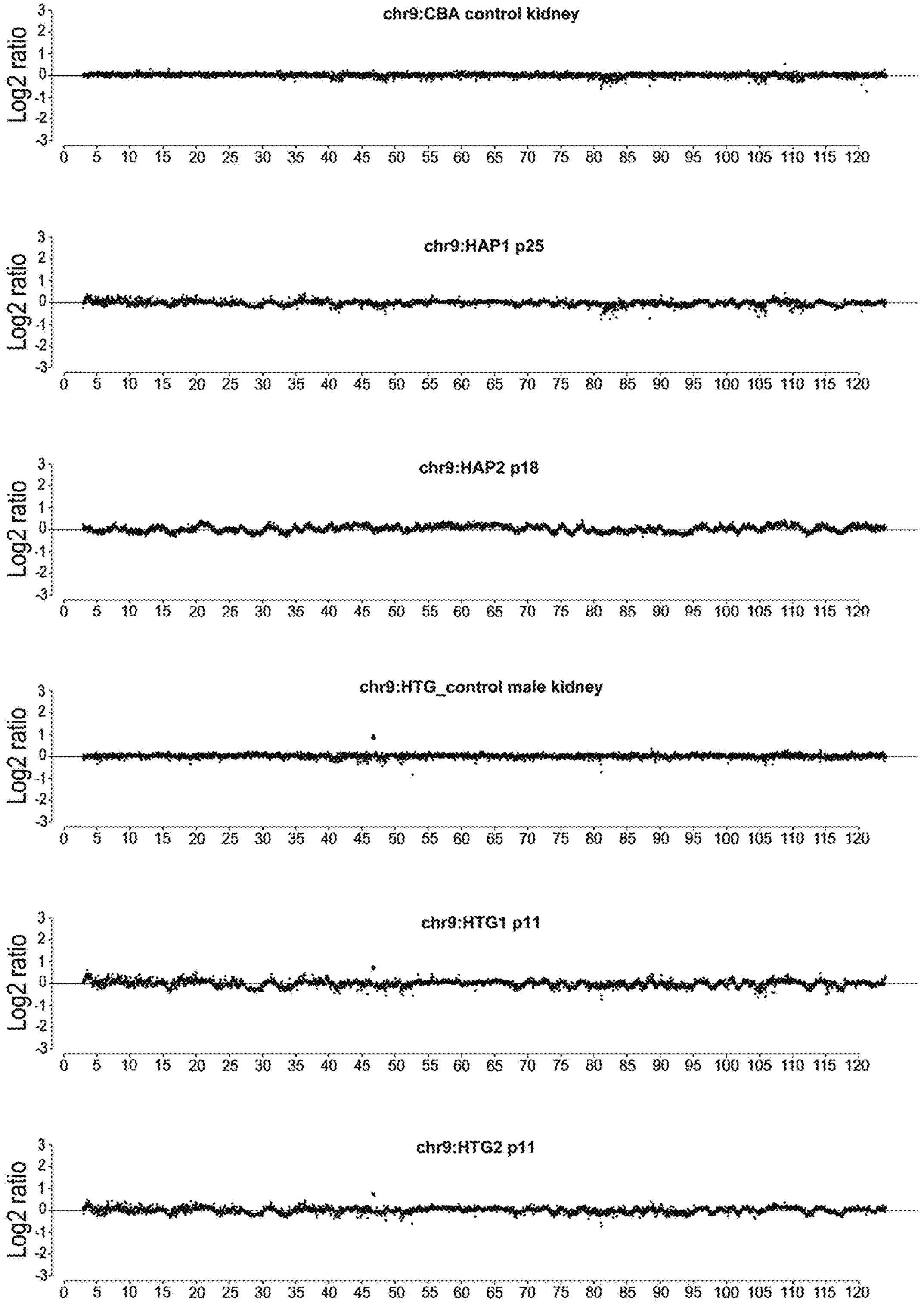
Figure 11:
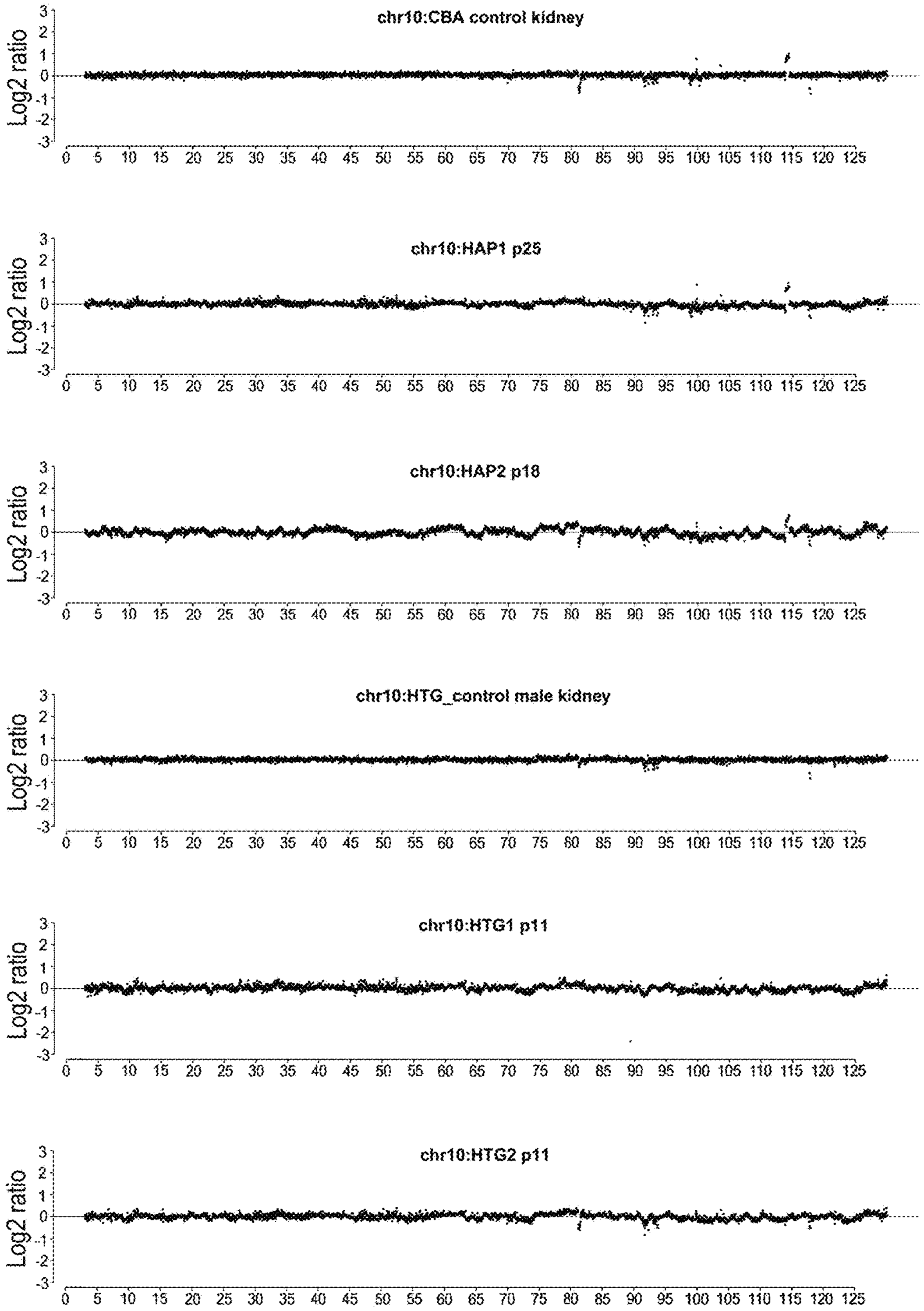
Figure 11:
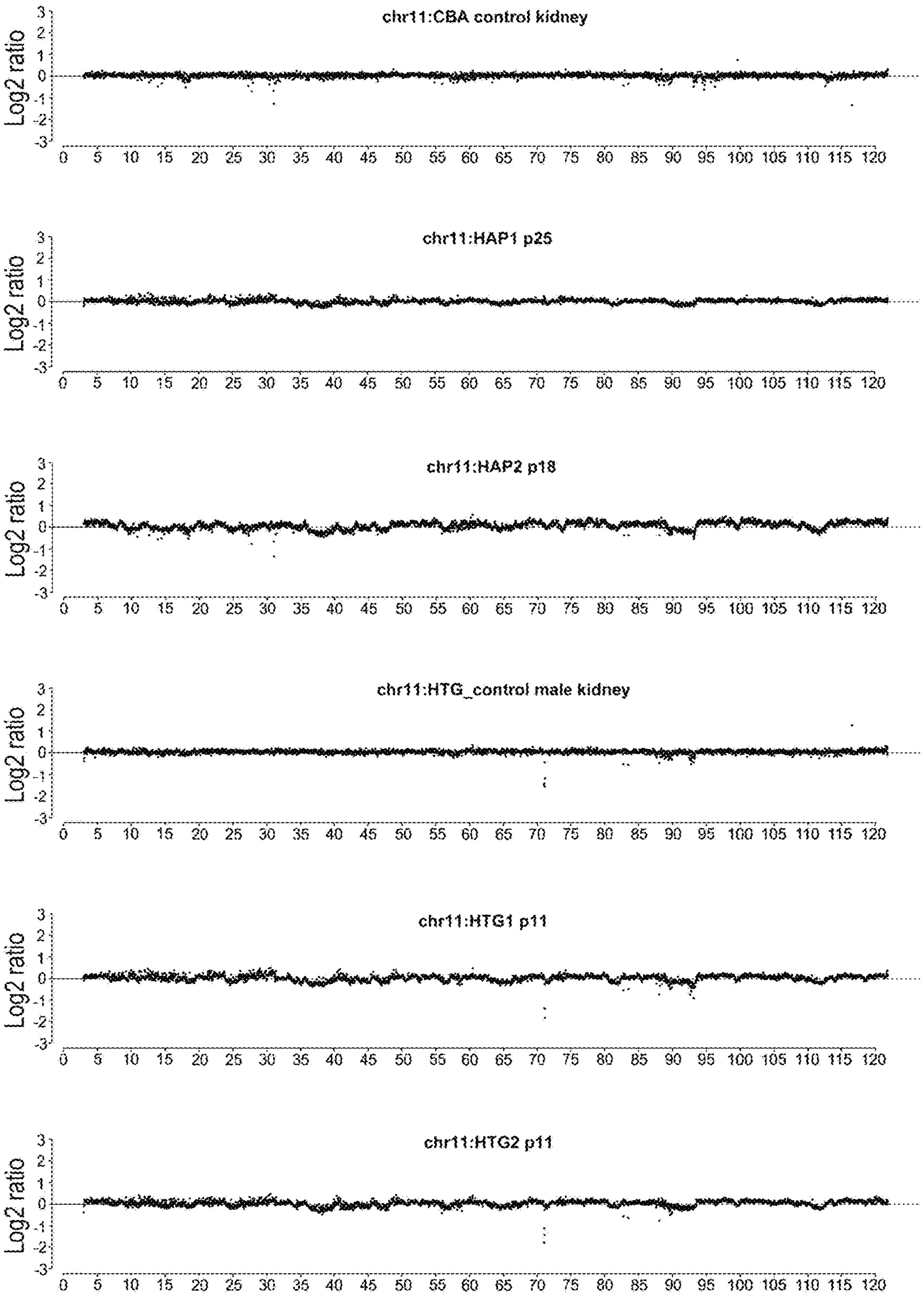
Figure 11:
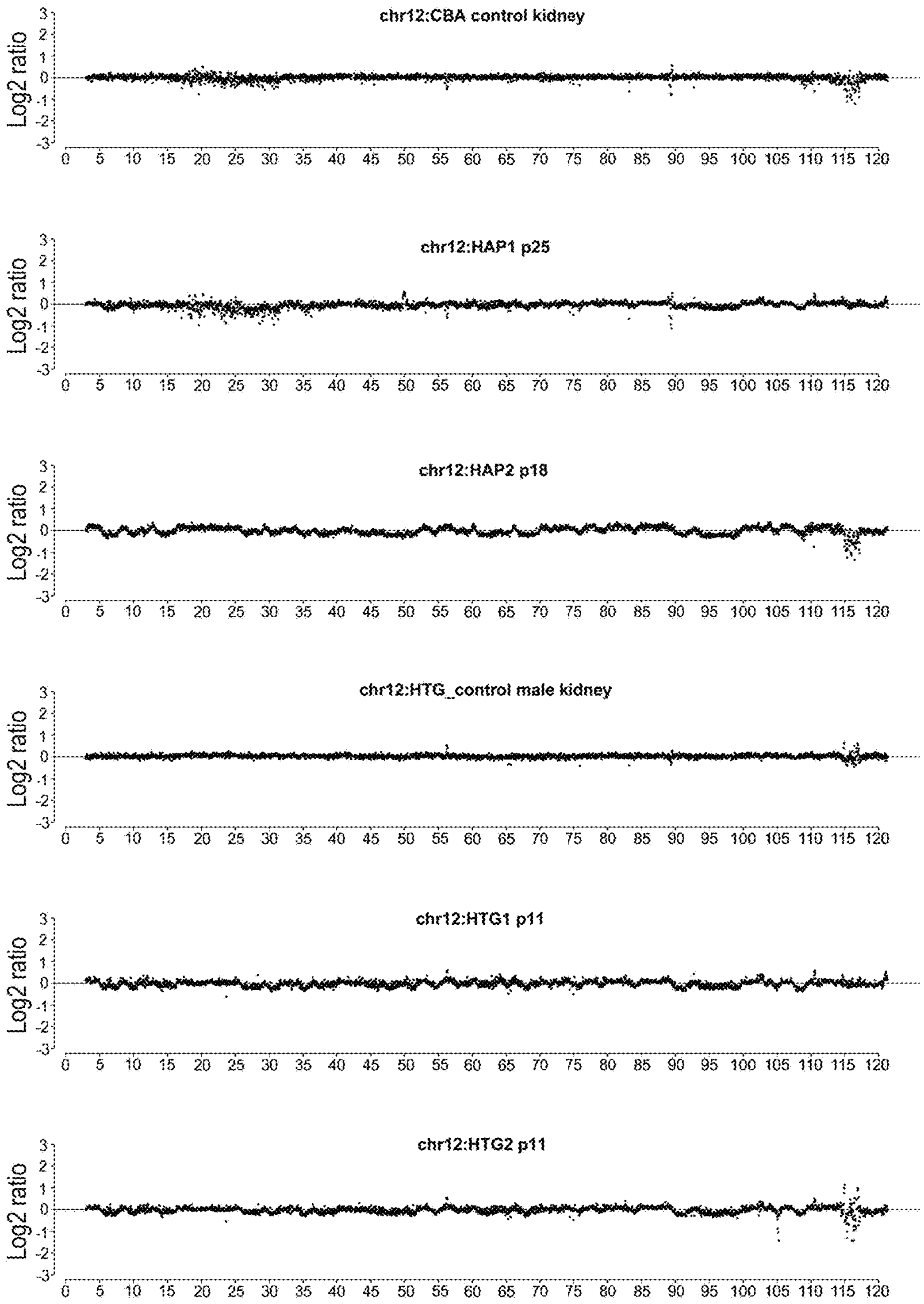
Figure 11:
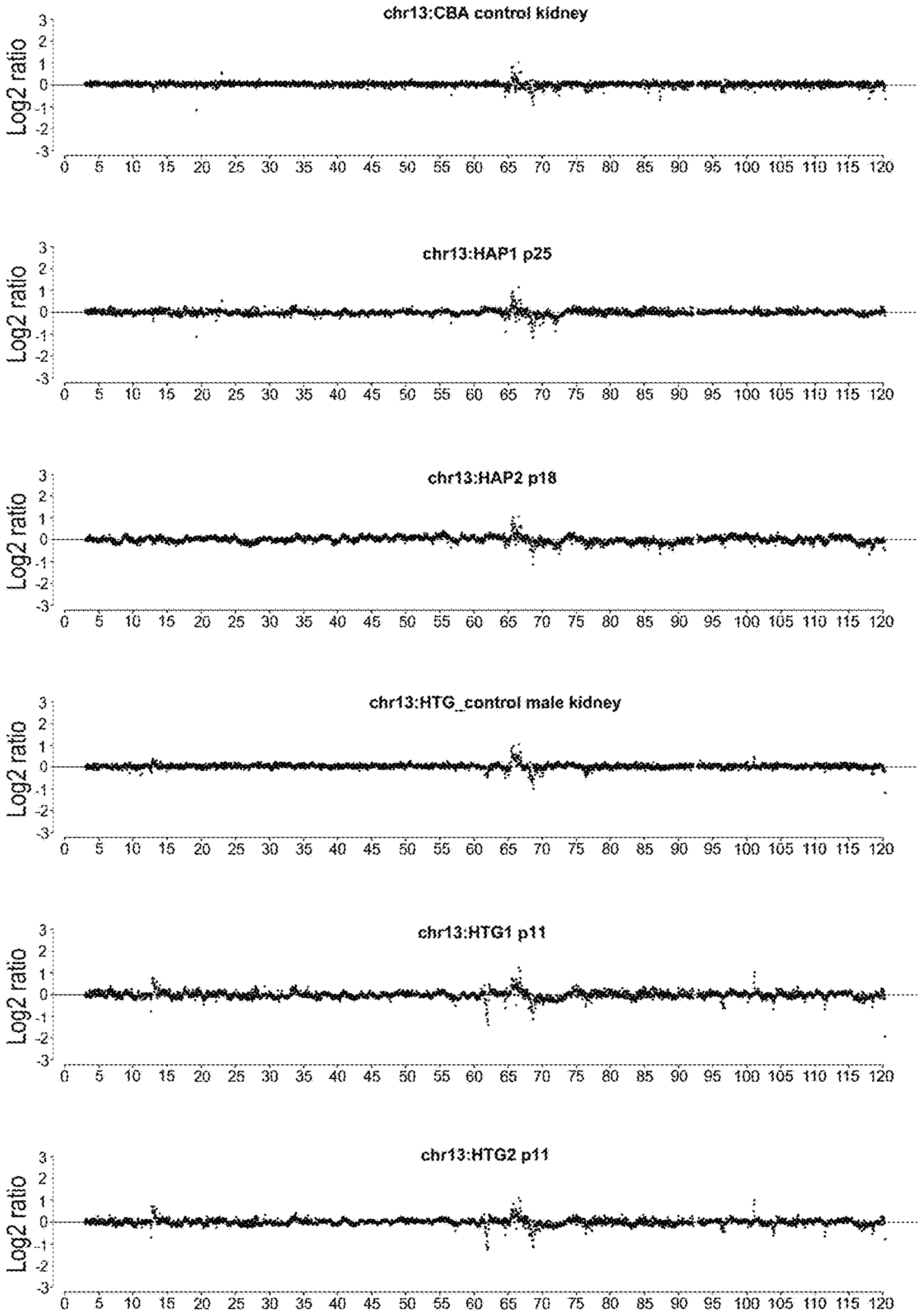
Figure 11:
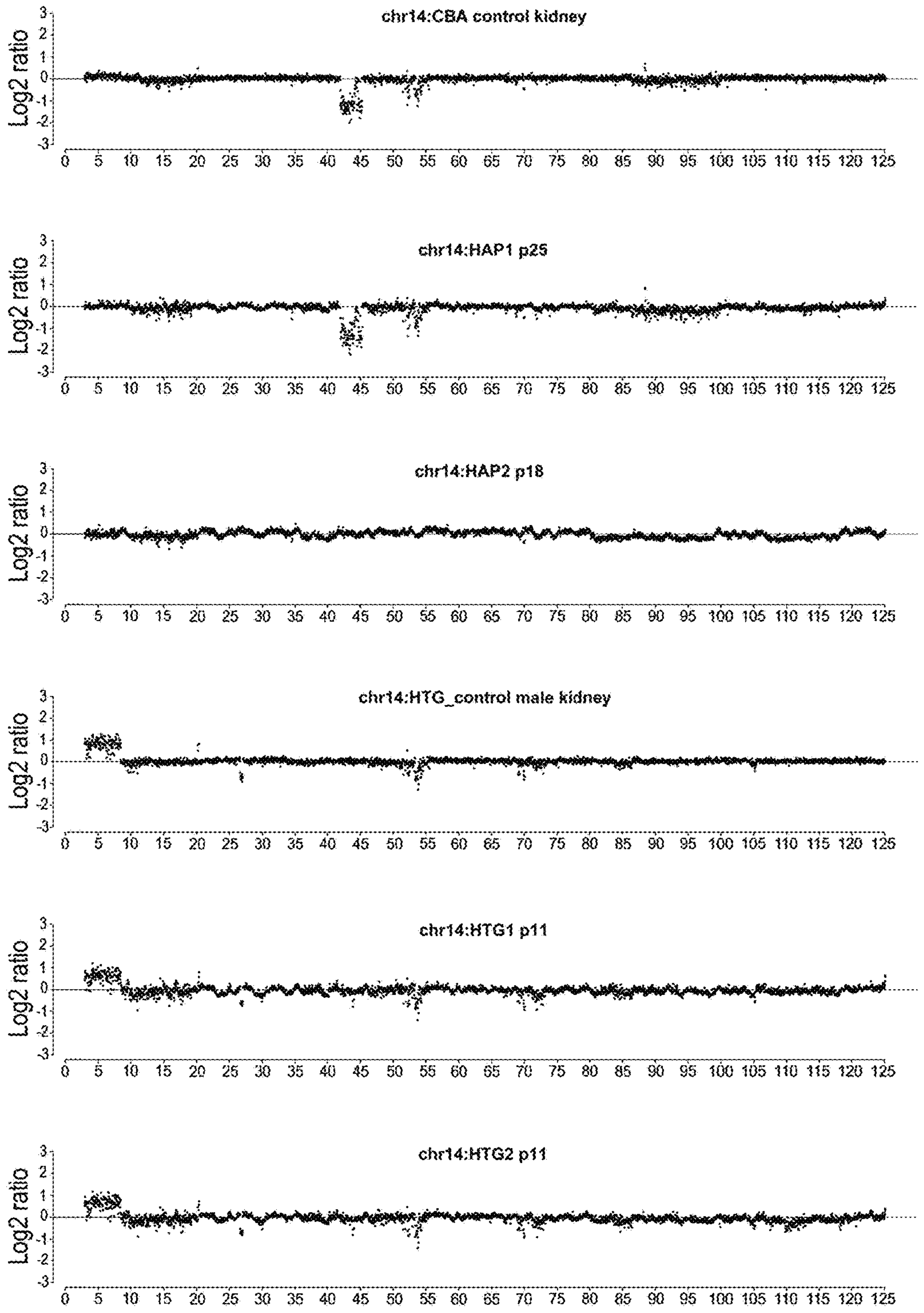
Figure 11:
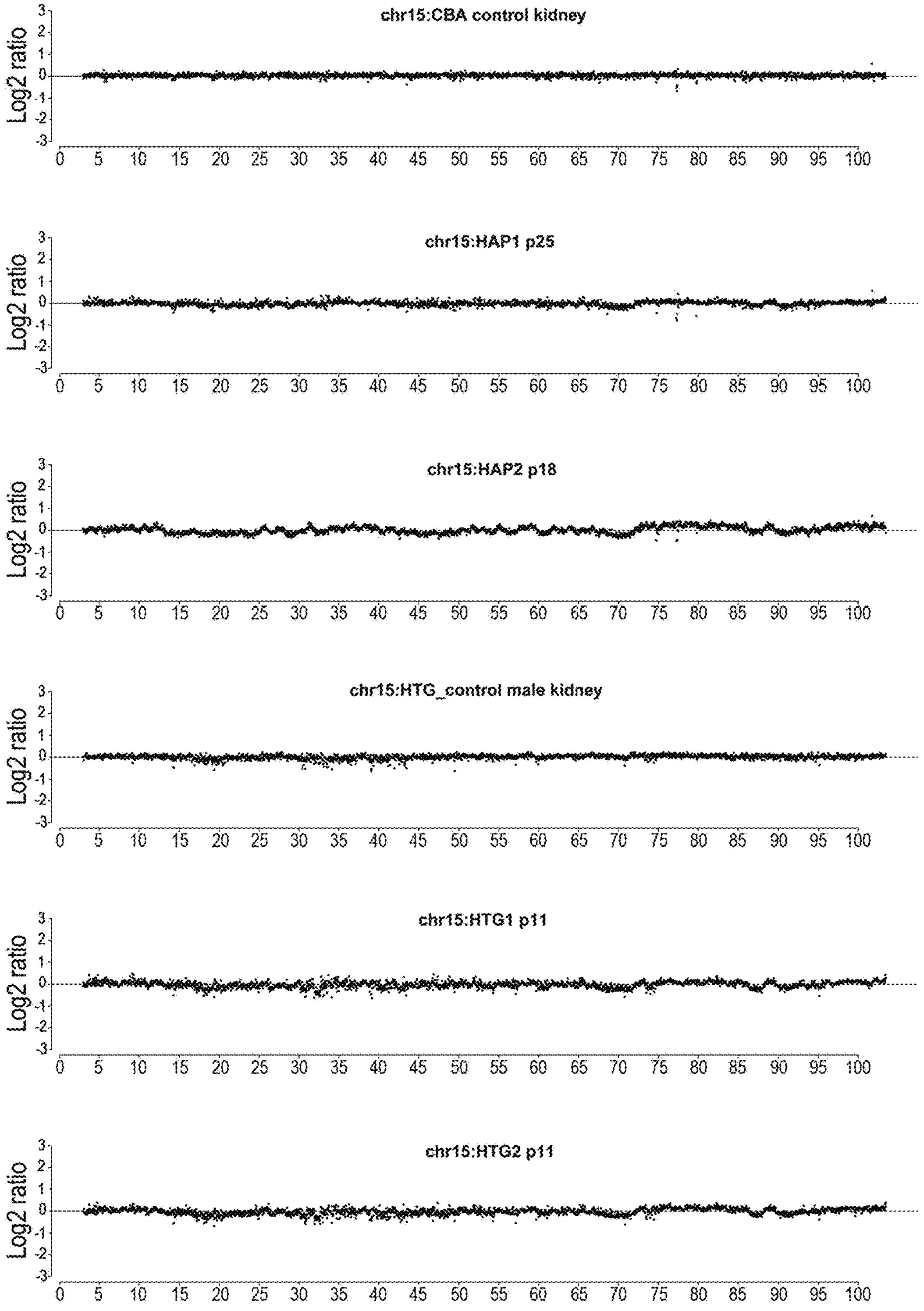
Figure 11:
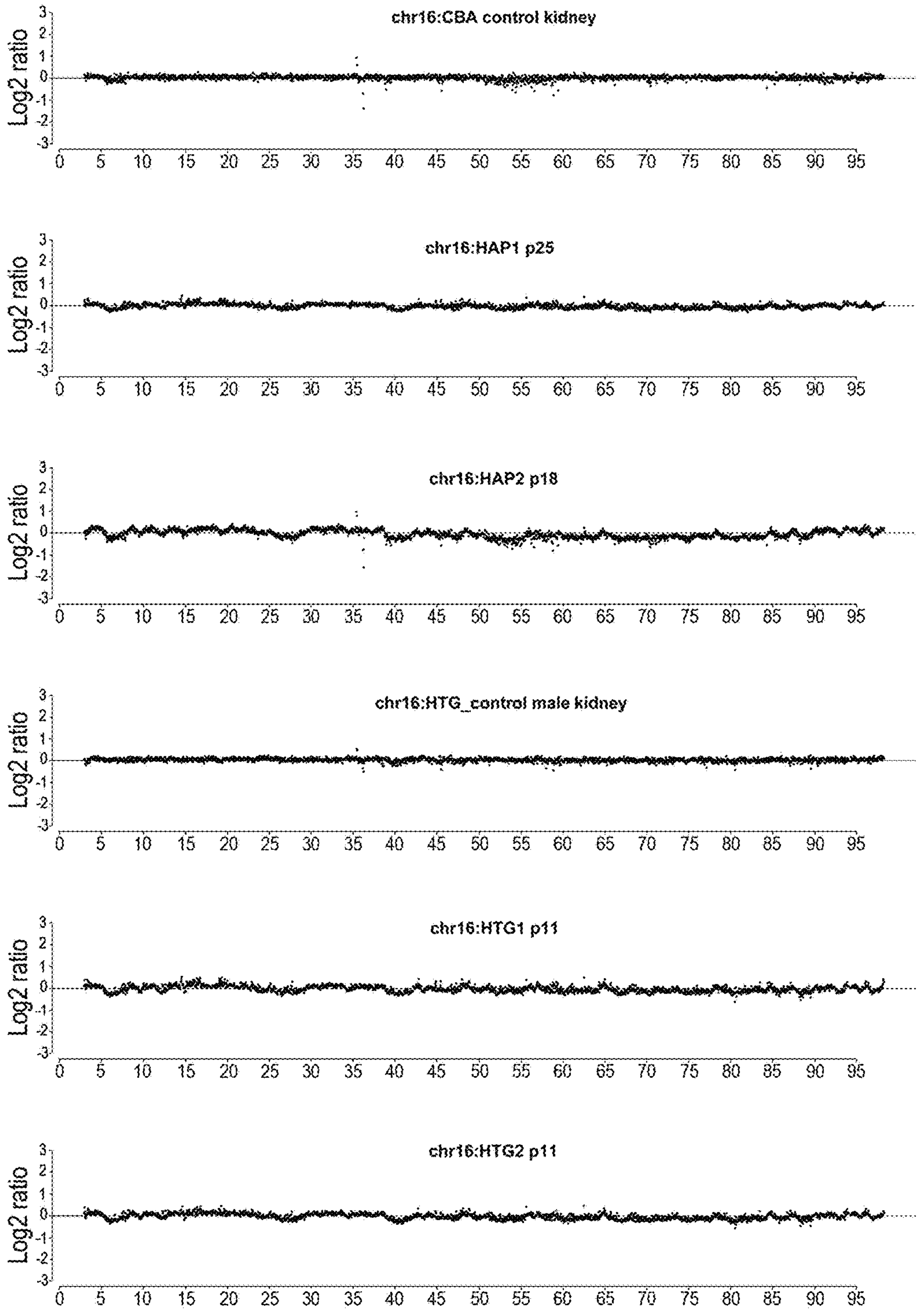
Figure 11:
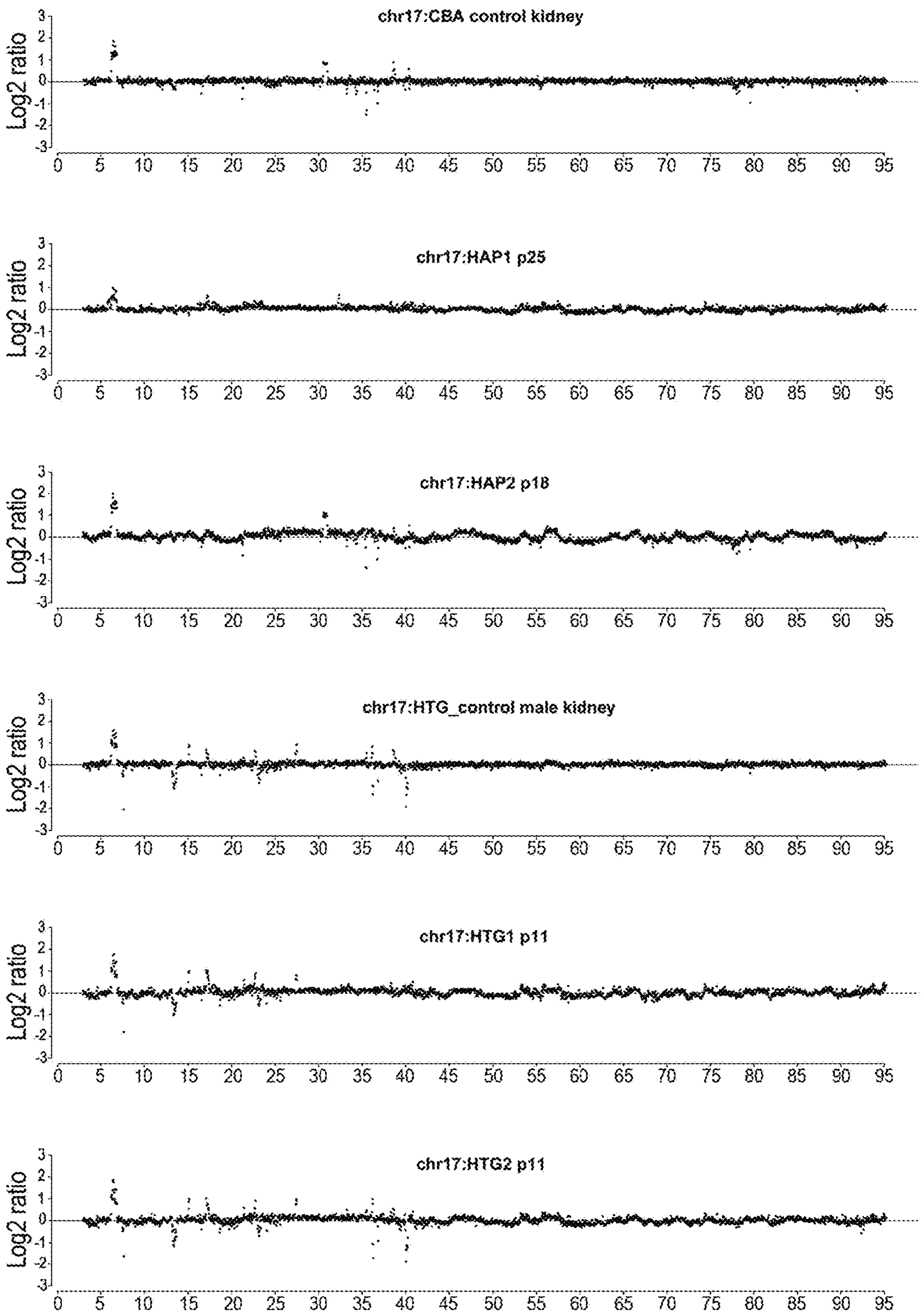
Figure 11:
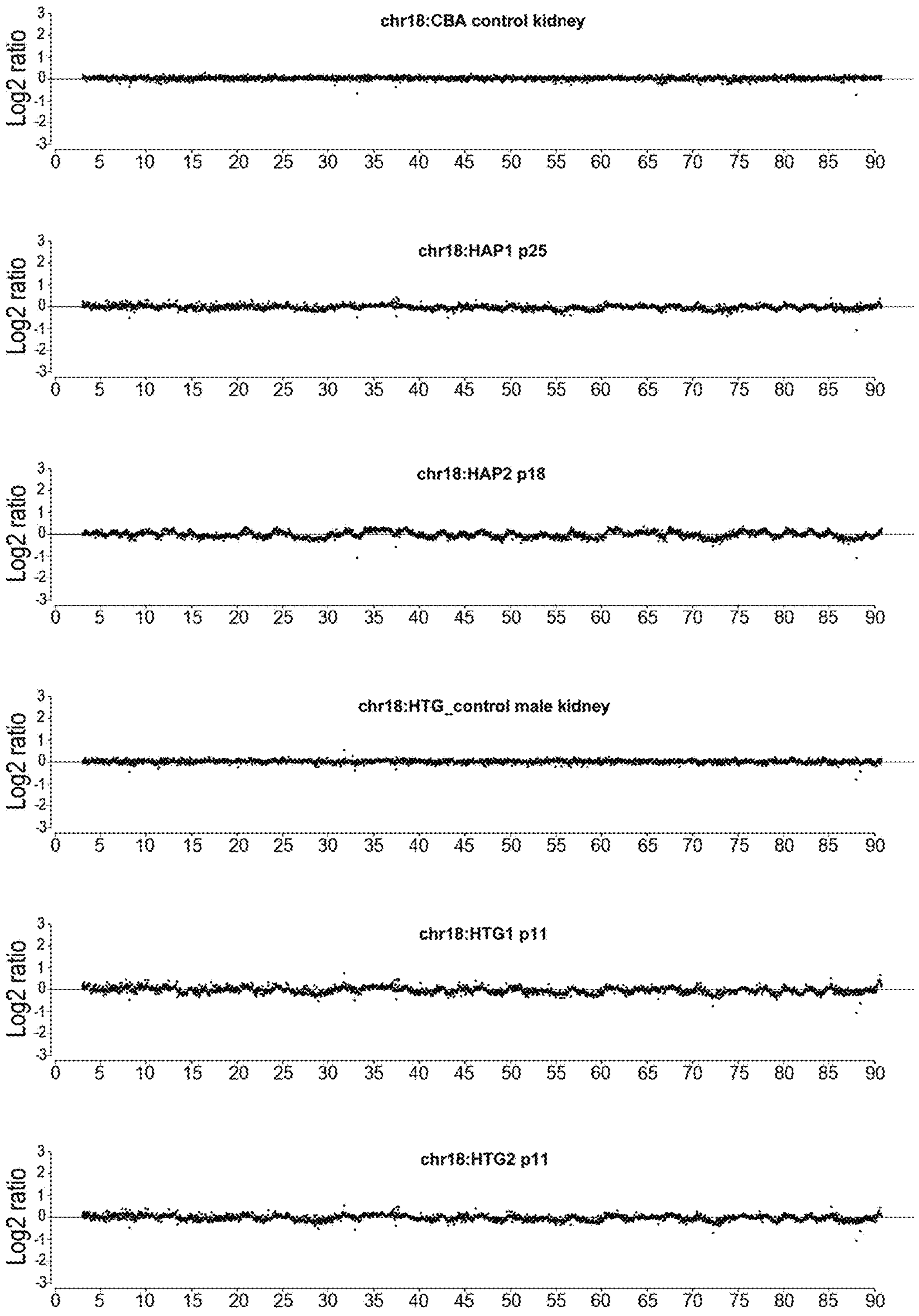
Figure 11:
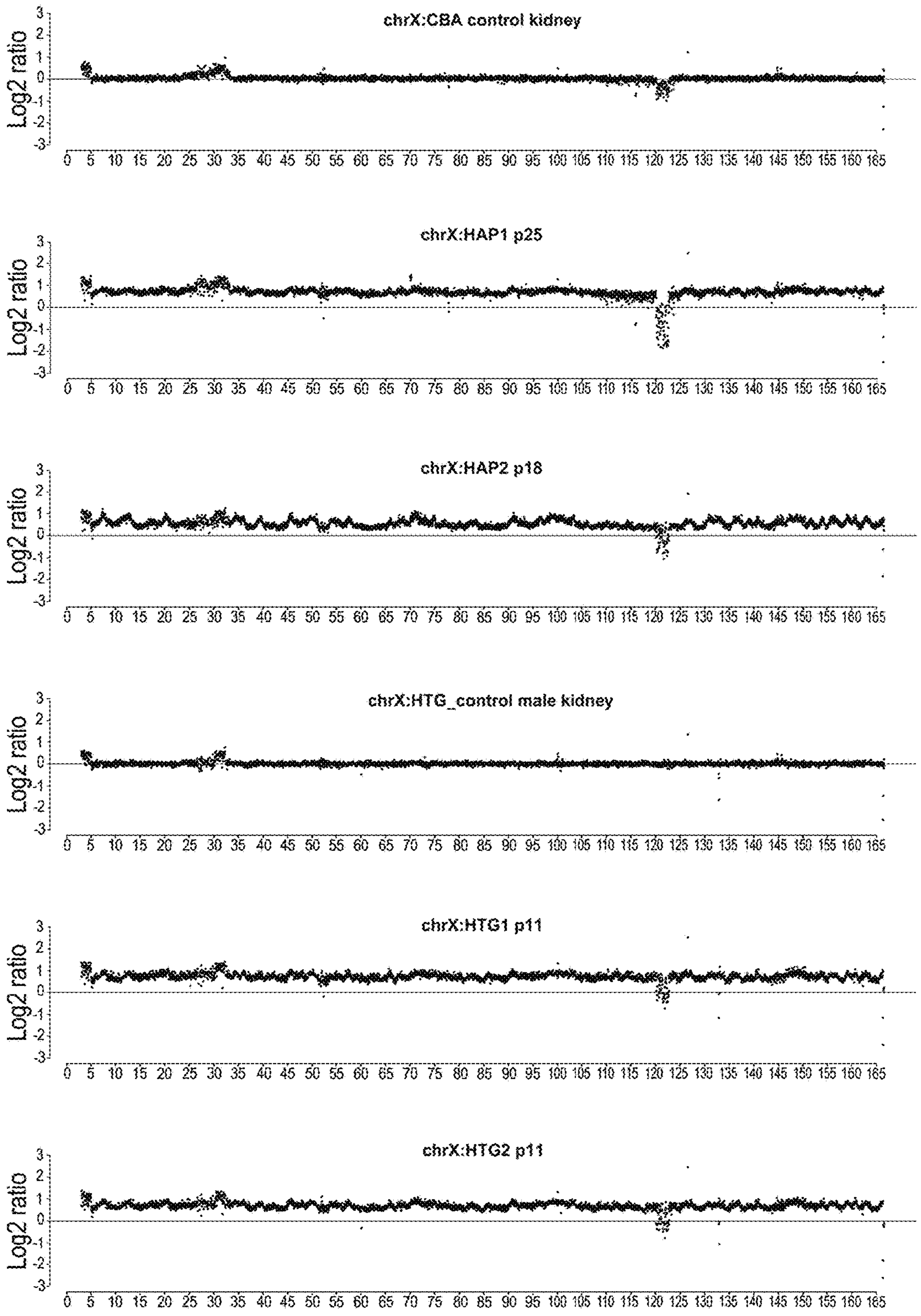
Figure 11:
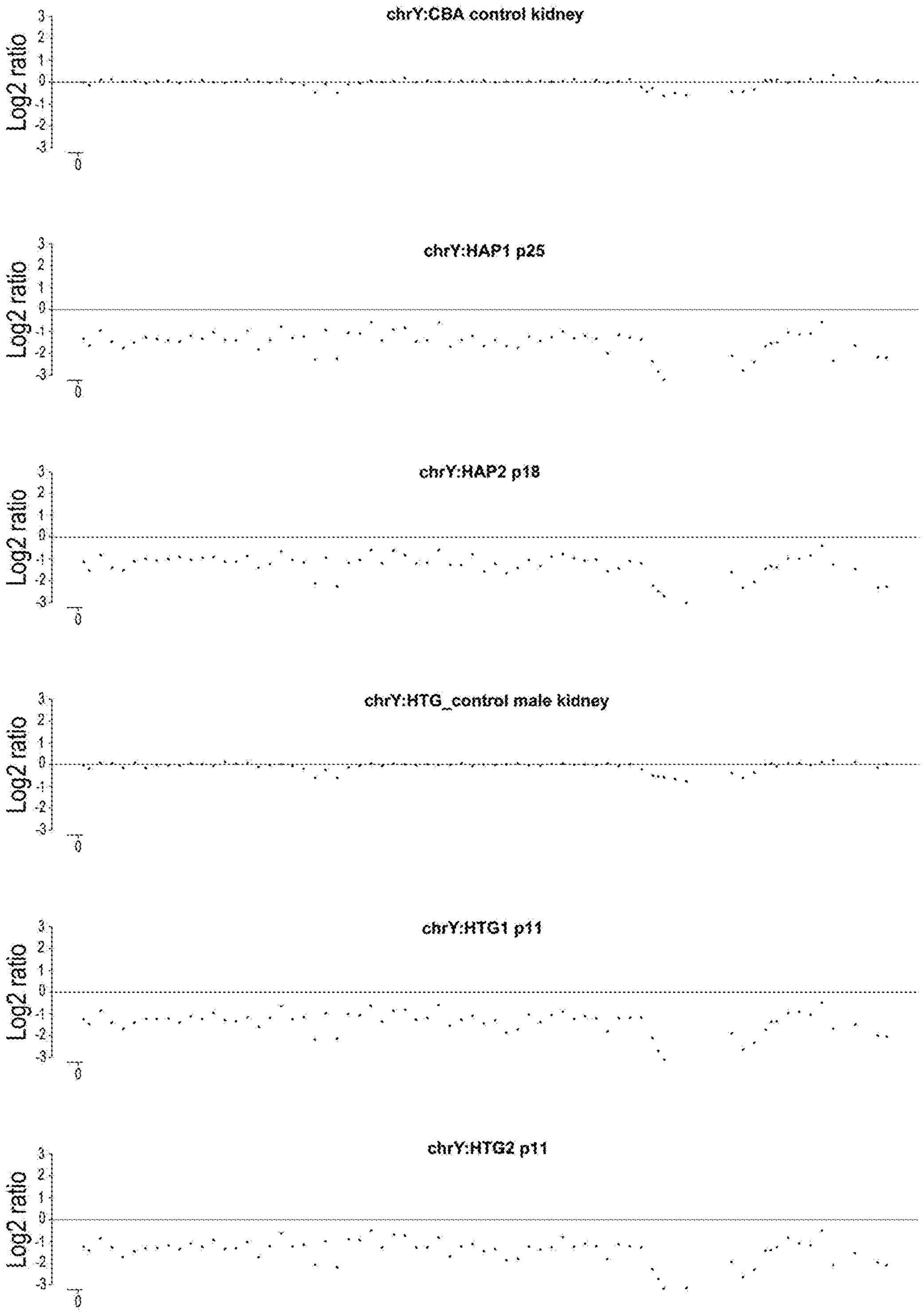
Figure 11:
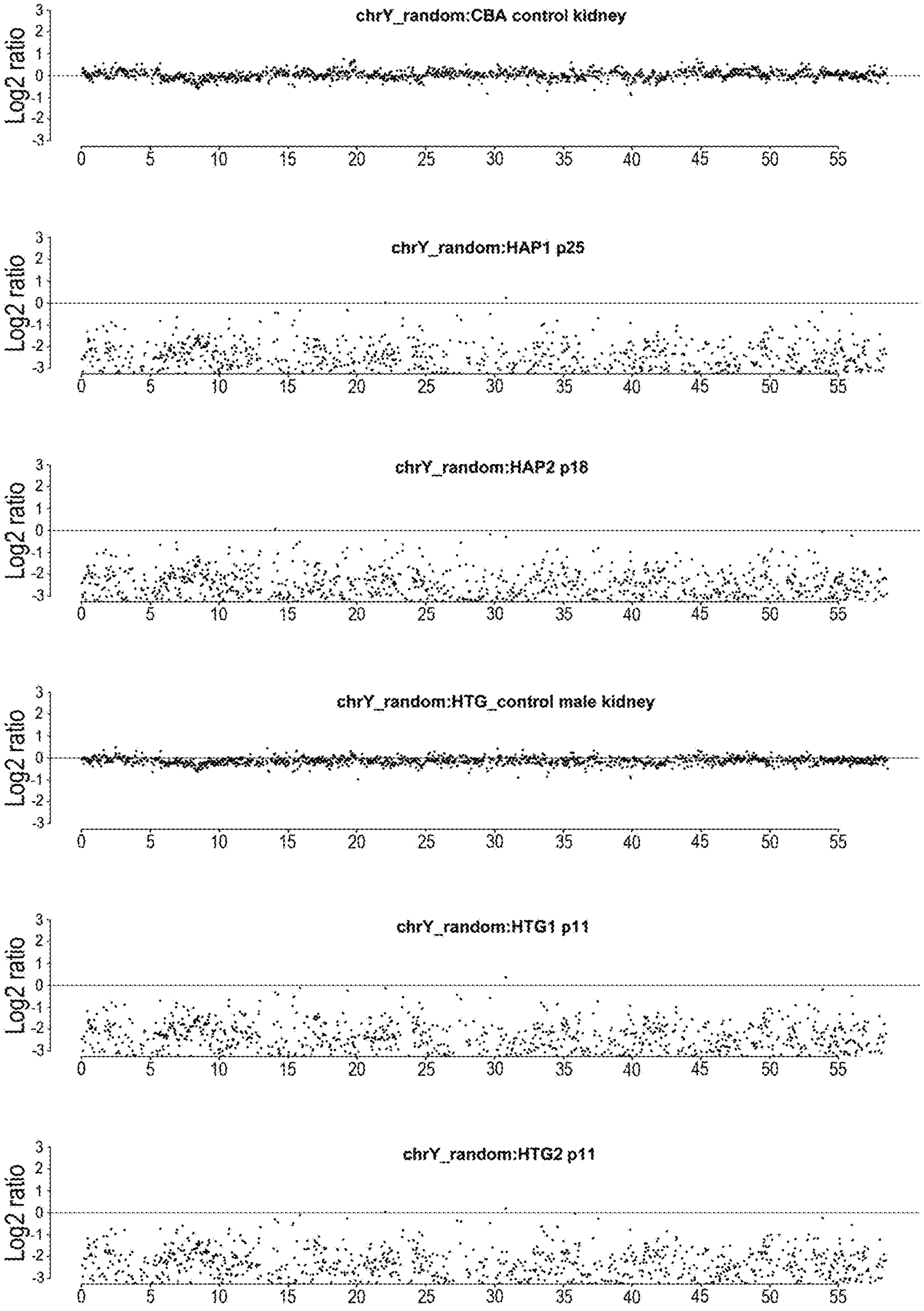

We further tested the requirements for deriving haploid mouse ESCs (Table 3). These experiments showed that removal of the trophectoderm by immunosurgery was not essential. Haploid ESCs could also be established using DMEM medium supplemented with Knockout Serum Replacement (KSR) and LIF showing that derivation without kinase inhibitors is possible (Table 3 and FIGS. 8A and 8B). We further succeeded in isolating haploid ESCs from the 129Sv inbred mouse strain and two genetically modified mouse lines. In the latter several alleles had been bred to homozygosity and maintained on a mixed genetic background for several generations (Table 3, and FIGS. 9A and 9B). In summary, we derived 25 haploid ESC lines in 7 independent experiments. Haploid ESC cultures could also be maintained on feeders in serum containing DMEM supplemented with LIF.

Figure 5D:
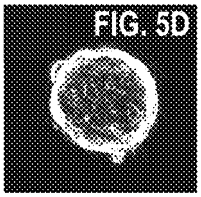
Figure 5E:
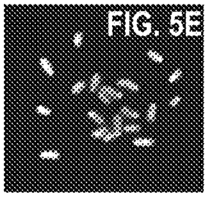
Figure 5F:
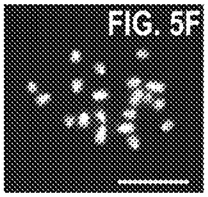
Figure 5G:
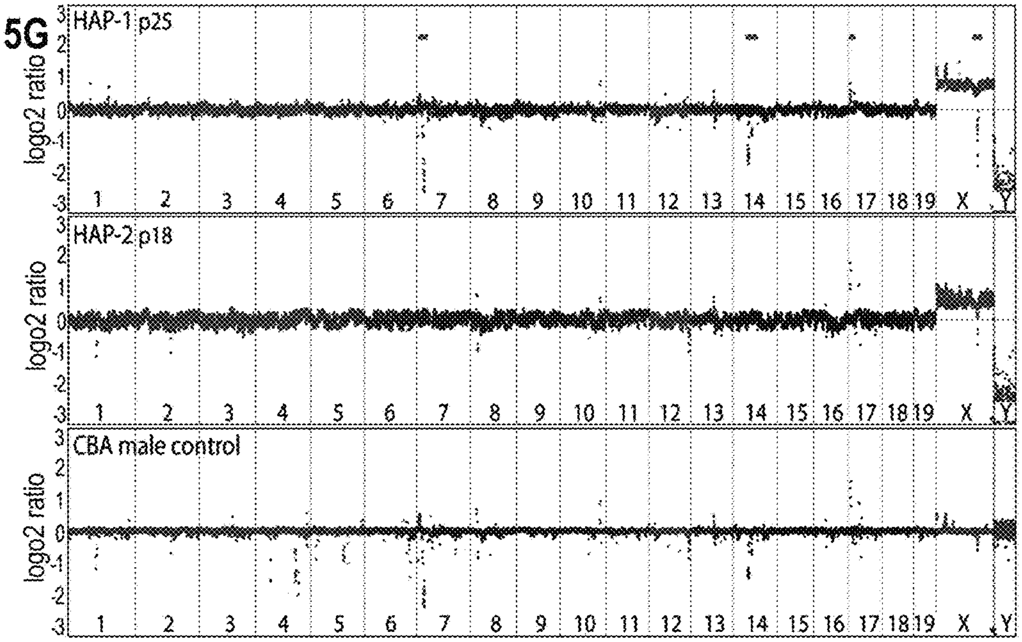
Figure 5H:
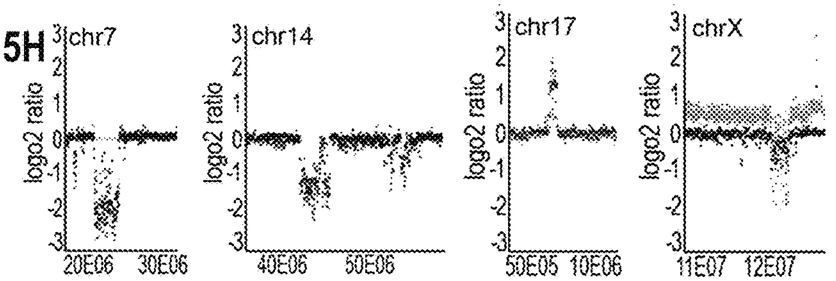

Haploid ESCs exhibited a typical mouse ESC colony morphology (FIG. 5D). Chromosome spreads showed 20 chromosomes corresponding to the haploid mouse chromosome set (FIGS. 5E and 5F). For further characterizing the genetic integrity we performed comparative genomic hybridization (CGH) of 4 haploid ESC lines and control DNA from the CBA strain and the mixed transgenic mouse line from which HTG-1 and HTG-2 ESCs were derived (FIGS. 5G and 5H and FIGS. 10A, 10B, and 11). Copy number variations (CNVs) that were detected in the genome of haploid ESC lines were also present in the strains of origin (FIG. 16). Albeit some CNVs appeared haploid ESC specific, inspection of the actual signals (FIG. 11) suggested that these CNVs were also present in the CBA or HTG control DNAs but not detected with the threshold applied. CNVs between the C57BL6 and CBA strain of mice were consistent with a previously reported analysis[12]. Taken together these data show that haploid ESCs maintained an intact haploid genome without amplifications or losses.

Figure 6A:
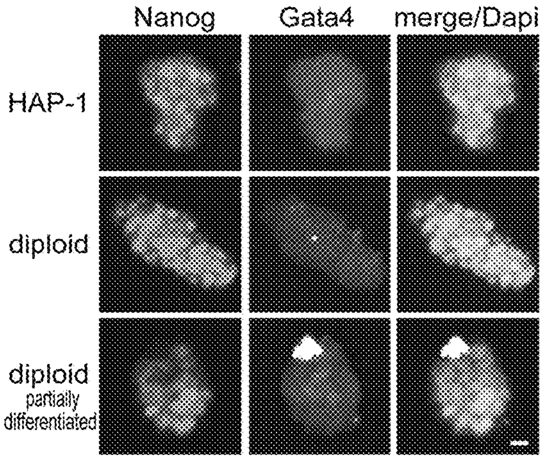
FIGS. 6A-6D show expression analysis of haploid ESCs.
Figure 6C:
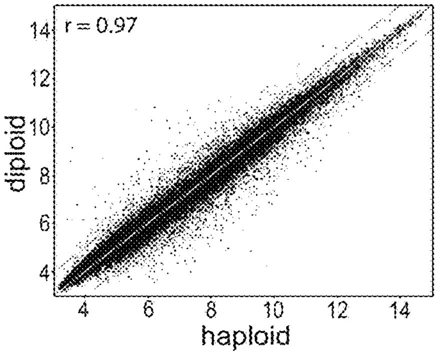
Figure 6B:
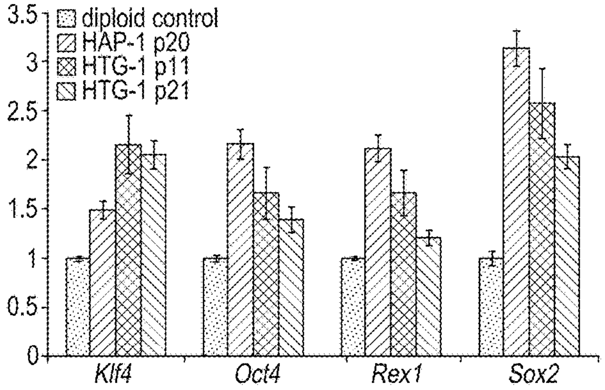
Figure 6D:
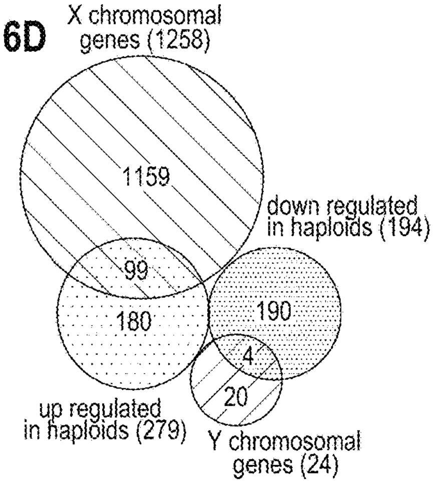

On the molecular level, haploid ESCs expressed pluripotency markers including Oct4, Rex1, Klf4, Sox2 and Nanog (FIGS. 6A and 6B). Genome-wide expression analysis showed a high correlation (Pearson correlation coefficient r=0.97 over all genes) between haploid ESCs and control diploid male ESCs (FIG. 6C and FIG. 12). In haploid ESCs 279 and 194 genes were more than 2-fold up- or down-regulated ($p<0.05$), respectively (FIG. 17). Among these, 99 X-linked genes were overexpressed and 4 Y-linked genes were lost in haploid ESCs consistent with different sex chromosome constitutions (FIG. 6D). Thus, haploid ESCs largely maintain a mouse ESC transcription profile.

Figure 7A:
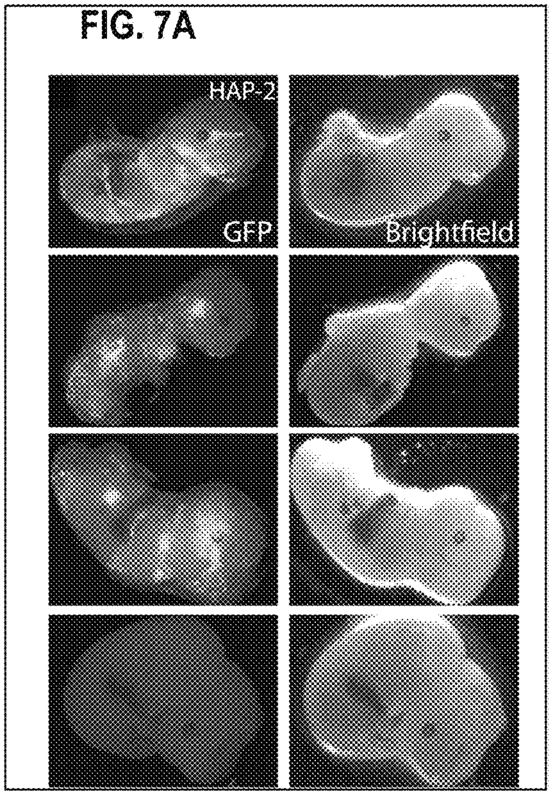
FIGS. 7A-7D show developmental potential of haploid ESCs.
Figure 7B:
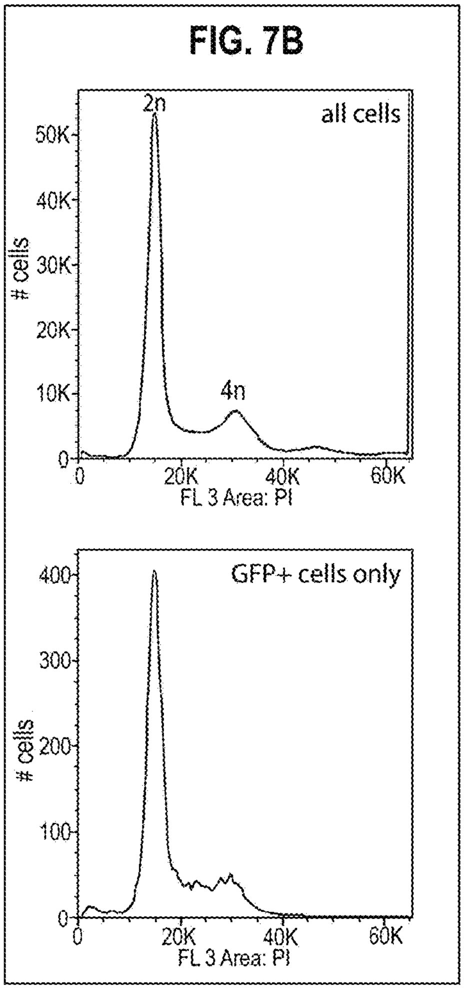
Figure 7C:
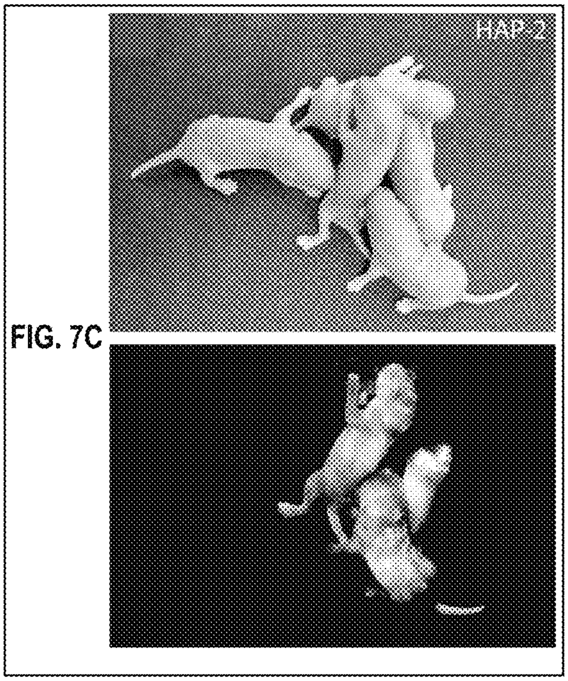
Figure 7D:
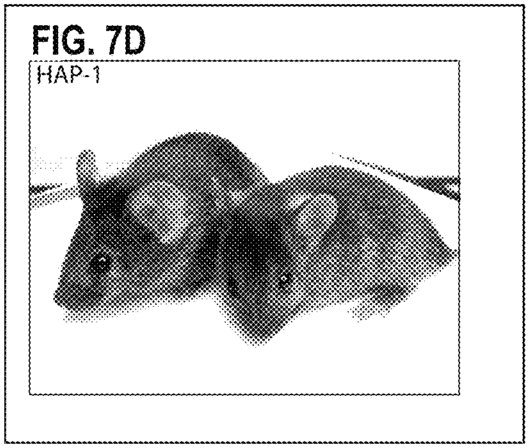
Figure 13A:
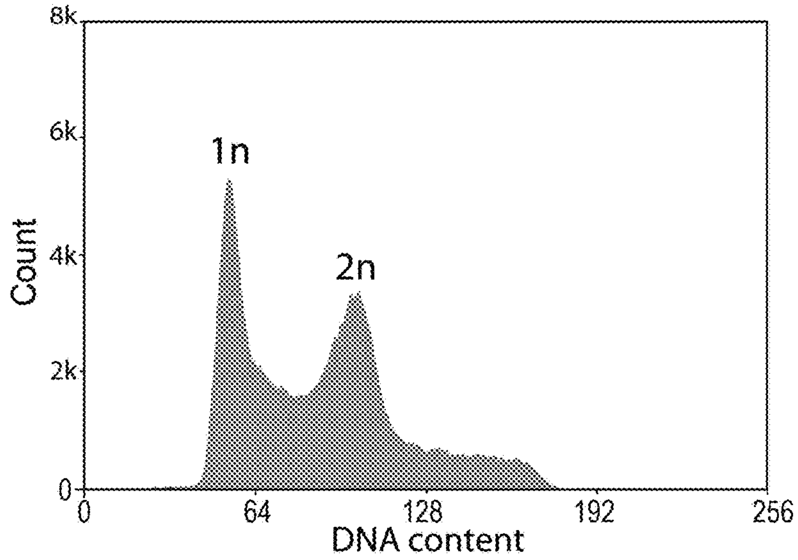
Figure 13B:
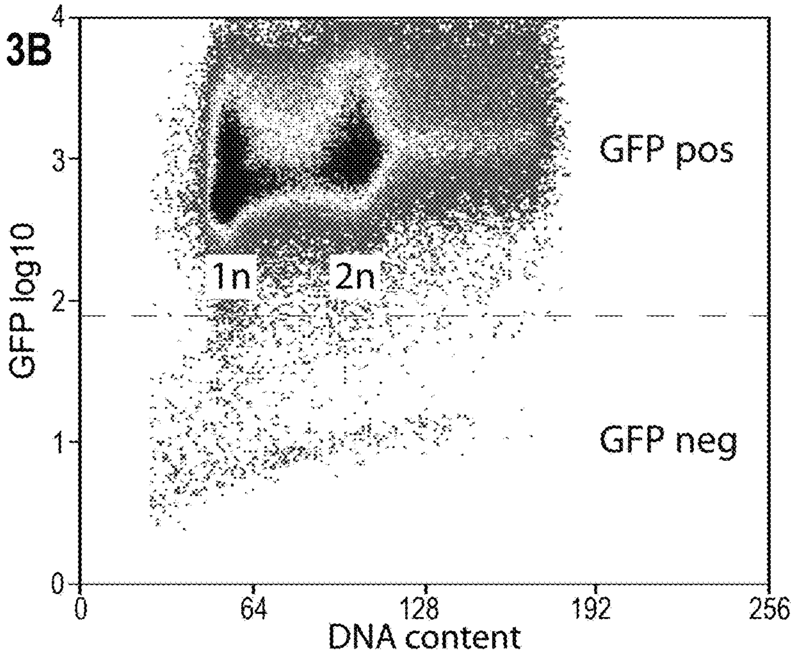

This prompted us to investigate the developmental potential of haploid ESCs. For this we introduced a piggyBac transposon vector for expressing green fluorescent protein (GFP) into HAP-2 ESCs. Flow sorting of cells for GFP fluorescence and DNA staining with Hoechst 33342 yielded a haploid ESC population that expressed GFP at high level showing that a haploid genome content was maintained during the transfection procedure (FIGS. 13A and 13B). GFP marked haploid ESCs contributed substantially to chimeric embryos when injected into C57BL/6 blastocysts (FIG. 7A). The great majority of GFP positive cells extracted from chimeric embryos had a diploid DNA content (FIG. 7B) indicating that haploid ESCs contributed extensively to development after diploidization. We also obtained 2 male and 2 female live born chimeras with a substantial contribution from haploid ESCs (FIG. 7C). These mice developed normally with apparent coat colour chimerism. Similar results were obtained with the HAP-1 and HTG-2 ESCs (FIG. 7D and FIG. 14A). Furthermore, the diploid fraction of HAP-2 ESCs at passage 31 could be differentiated into Nestin positive cells following a neural in vitro differentiation protocol[13] (FIG. 14B). Taken together these findings demonstrate that haploid ESCs maintain a wide differentiation potential. These chimeric mice have transmitted the GFP transgene from the GFP transgenic HAP-1 haploid embryonic stem cell line to two of their offspring. This is evidence for the ability of introducing mutations or genetic modifications into mice via haploid ES cells.

To investigate the utility of haploid ESCs for genetic screening we performed a pilot screen for mismatch repair genes following a previously published strategy[14]. For this, $5\times10^6$ haploid ESCs were co-transfected with a gene trap piggyBac transposon vector (FIG. 15A) and a plasmid for expressing an optimized piggyBac transposase[15]. Gene trap insertions were selected with puromycin. A pool of $1\times10^7$ cells was then cultured in the presence of 2-amino-6-mercaptopurine (6-TG) which is toxic to mismatch repair proficient cells. After 8 days 20 6-TG resistant colonies were isolated and the integration sites were mapped using Splinkerette PCR[16]. Of 7 clones analysed we identified two independent insertions in Msh2 and one in Hprt (FIG. 15B). Msh2 is a known mismatch repair gene and Hprt is required for converting 6-TG into a toxic metabolite[14]. Thus, identification of mutations in autosomal genes was possible suggesting a potential for haploid ESCs in forward genetic screening in mammals.

The difficulty in obtaining haploid ESC lines in previous attempts might be explained by aberrant gene regulation such as aberrant dosage compensation and genomic imprinting. However, diploid ESCs from mouse and human parthenogenetic embryos have been established[17,18]. Misregulation of X inactivation has been observed to some extent in haploid mouse embryos[5] and has also been shown to reduce the efficiency of producing cloned mice[19]. Thus, it is conceivable that X inactivation is initiated aberrantly in haploid embryos during some ESC derivation procedures. Direct capture of naive pluripotent cells from ICM outgrowths as accentuated by the use of 2i conditions[11] could have contributed to the success of our study.

Previously, near-haploid cells have been observed in human tumours (for literature review see[20]) and a near-haploid human tumour derived cell line has been described[21,22]. These tumour cells carry genomic rearrangements and mutations that might stabilize the haploid genome. An interesting aspect of haploid ESCs is their developmental potential. We have observed rapid diploidization when haploid ESCs differentiate. The resulting diploid parthenogenetic cells can contribute to development[23]. It is interesting to speculate whether differentiated haploid lineages can be generated perhaps through suppression of X inactivation and whether it is possible to derive haploid human ESCs.

Methods Summary

For the derivation of haploid ESCs mouse oocytes were activated in M16 medium as described[24]. ESC culture in chemically defined 2i medium has been described previously[7,8]. Cell sorting for DNA content was performed after staining with 15 μg/ml Hoechst 33342 (Invitrogen) on a MoFlo flow sorter (Beckman Coulter) selecting the haploid 1n peak. For analytic flow profiles cells were fixed in ethanol, RNase treated, and stained with propidium iodide (PI). For karyotype analysis cells were arrested in metaphase with demecolcine (Sigma). After incubation in hypotonic KCl buffer cells were fixed in methanol-acetic acid (3:1) and chromosome spreads were prepared and stained with DAPI. RNA was extracted using the RNeasy Kit (Quiagen). Transcription profiles were generated using Affymetrix GeneChip 430.2 arrays. Sample preparation, hybridization, and basic data analysis were performed by Imagenes (Berlin, Germany). Further analysis was performed using the Genespring GX software (Agilent). For CGH analysis genomic DNA was isolated from haploid ESC lines and hybridized to NimbleGen 3×720K whole-genome tiling arrays by Imagenes (Berlin, Germany) using C57BU6 kidney DNA as a reference. For chimera experiments GFP labelled HAP-1 (p29), HAP-2 (p18) and HTG-2 (p23) ESCs were injected into C57BU6 host blastocysts. Live born chimaeras were analysed for expression of GFP at postnatal day 2. Genetic screening was performed following a previously published strategy[25]. In brief, HAP-1 ESCs were co-transfected with 2

µg piggyBac transposase expression vector[15] and 1 µg piggyBac gene trap vector (FIGS. 15A and 15B) using Lipofectamine 2000 (Invitrogen). Selection for transposon insertions was performed using 2 µg/ml puromycin for 8 days. $1 \times 10^7$ puromycin resistant ESCs were plated in two 15 cm dishes and mutations in mismatch repair genes were selected using 0.3 µg/ml 6-TG (Sigma). piggyBac integration sites in seven 6-TG resistant clones were mapped by Splinkerette PCR[16].

References for Example 3
1. Otto, S. P. & Jarne, P. Evolution. Haploids—hapless or happening? *Science* 292, 2441-3 (2001).
2. Wiellette, E. et al. Combined haploid and insertional mutation screen in the zebrafish. *Genesis* 40, 231-40 (2004).
3. Yi, M., Hong, N. & Hong, Y. Generation of medaka fish haploid embryonic stem cells. *Science* 326, 430-3 (2009).
4. Kaufman, M. H., Robertson, E. J., Handyside, A. H. & Evans, M. J. Establishment of pluripotential cell lines from haploid mouse embryos. *J Embryol Exp Morphol* 73, 249-61 (1983).
5. Latham, K. E., Akutsu, H., Patel, B. & Yanagimachi, R. Comparison of gene expression during preimplantation development between diploid and haploid mouse embryos. *Biol Reprod* 67, 386-92 (2002).
6. Kaufman, M. H. Chromosome analysis of early postimplantation presumptive haploid parthenogenetic mouse embryos. *J Embryol Exp Morphol* 45, 85-91 (1978).
7. Ying, Q. L. et al. The ground state of embryonic stem cell self-renewal. *Nature* 453, 519-23 (2008).
8. Nichols, J. et al. Validated germline-competent embryonic stem cell lines from nonobese diabetic mice. *Nat Med* 15, 814-8 (2009).
9. Buehr, M. et al. Capture of authentic embryonic stem cells from rat blastocysts. *Cell* 135, 1287-98 (2008).
10. Nichols, J., Silva, J., Roode, M. & Smith, A. Suppression of Erk signalling promotes ground state pluripotency in the mouse embryo. *Development* 136, 3215-22 (2009).
11. Nichols, J. & Smith, A. The origin and identity of embryonic stem cells. *Development* 138, 3-8 (2011).
12. Cutler, G., Marshall, L. A., Chin, N., Baribault, H. & Kassner, P. D. Significant gene content variation characterizes the genomes of inbred mouse strains. *Genome Res* 17, 1743-54 (2007).
13. Pollard, S. M., Benchoua, A. & Lowell, S, Neural stem cells, neurons, and glia. *Methods Enzymol* 418, 151-69 (2006).
14. Li, M. A., Pettitt, S. J., Yusa, K. & Bradley, A. Genome-wide forward genetic screens in mouse ES cells. *Methods Enzymol* 477, 217-42 (2010).
15. Cadinanos, J. & Bradley, A. Generation of an inducible and optimized piggyBac transposon system. *Nucleic Acids Res* 35, e87 (2007).
16. Mikkers, H. et al. High-throughput retroviral tagging to identify components of specific signaling pathways in cancer. *Nat Genet* 32, 153-9 (2002).
17. Mai, Q. et al. Derivation of human embryonic stem cell lines from parthenogenetic blastocysts. *Cell Res* 17, 1008-19 (2007).
18. Revazova, E. S. et al. Patient-specific stem cell lines derived from human parthenogenetic blastocysts. *Cloning Stem Cells* 9, 432-49 (2007).
19. Inoue, K. et al. Impeding Xist expression from the active X chromosome improves mouse somatic cell nuclear transfer. *Science* 330, 496-9 (2010).
20. Sukov, W. R. et al. Nearly identical near-haploid karyotype in a peritoneal mesothelioma and a retroperitoneal malignant peripheral nerve sheath tumor. *Cancer Genet Cytogenet* 202, 123-8 (2010).
21. Kotecki, M., Reddy, P. S. & Cochran, B. H. Isolation and characterization of a near-haploid human cell line. *Exp Cell Res* 252, 273-80 (1999).
22. Carette, J. E. et al. Haploid genetic screens in human cells identify host factors used by pathogens. *Science* 326, 1231-5 (2009).
23. Jiang, H. et al. Activation of paternally expressed imprinted genes in newly derived germline-competent mouse parthenogenetic embryonic stem cell lines. *Cell Res* 17, 792-803 (2007).
24. Kishigami, S. & Wakayama, T. Efficient strontium-induced activation of mouse oocytes in standard culture media by chelating calcium. *J Reprod Dev* 53, 1207-15 (2007).
25. Guo, G., Wang, W. & Bradley, A. Mismatch repair genes identified using genetic screens in Blm-deficient embryonic stem cells. *Nature* 429, 891-5 (2004).

TABLE 3

Derivation of haploid mouse ESC lines

| Exp. No | derivation protocol | Names of ESC lines used in study | genetic background | Oocytes activated | number of blastocysts | ESC lines obtained | ESC lines with haploid contribution (max. % haploid before sorting) |
|---|---|---|---|---|---|---|---|
| 1 | 2i/immunosurgery | HAP-1 to 6 † | B6CBAF1 | 132 | 30 | 27 | 6 (>60%) |
| 2 | 2i | HAP-7 | B6CBAF1 | 22 | 10 | 5 | 1 (>15%) |
| 3 | 2i | HTG-1 to 3 ‡ | mixed TG* | 50 | 32 | 3 | 3 (>90%) |
| 4 | KSR/immunosurgery | HAP-8 to 13 | B6CBAF1 | 273 | 48 | 22 | 6 (>10%) |
| 5 | 2i | H129B6-1 to 5 | 129B6F1 | 250 | 37 | 8 | 5 (>10%) |
| 6 | 2i | HTX-1 | mixed TG** | 70 | 11 | 1 | 1 (>40%) |
| 7 | 2i | H129-1 to 3 | 129Sv | 140 | 13 | 10 | 3 (>60%) |

† Contribution to chimeric mice was confirmed for the HAP-1 and HAP-2 haploid ESC lines.
‡ Contribution to chimeric mice was confirmed for the HTG-1 haploid ESC line.
*Derived from ROSA26$^{nlsrtTA}$ LC1 Xist$^{2LOX}$ homozygous female mice.
**Derived from ROSA26$^{nlsrtTA}$ tetOPXist homozygous female mice[30].

Methods for Example 3
Derivation of Haploid ESCs

Oocytes were isolated from superovulated females and activated in M16 medium using mM strontium chloride and 2 mM EGTA as described[24]. Embryos were subsequently cultured in M16 or KSOM medium microdrops covered by mineral oil. Under these conditions around 80% of oocytes reached the 2-cell stage on the next morning. Thereafter development of preimplantation embryos was variable with a large number of embryos showing unequal sized blastomeres or unusual embryo morphology. Removal of the zona, immunosurgery for removal of the trophectoderm and ESC derivation was performed as described previously[7,8]. ESCs were cultured in chemically defined 2i medium plus LIF as described[7,8] with minor modifications. 2i medium was supplemented with non essential amino acids and 0.35% BSA fraction V. Culture of ESCs on feeders was performed as previously described[26]. Knockout serum replacement (KSR) was obtained from Invitrogen. Cell sorting for DNA content was performed after staining with 15 μg/ml Hoechst 33342 (Invitrogen) on a MoFlo flow sorter (Beckman Coulter). The haploid 1n peak was purified. Diploid cells did arise in cultures to various extents in all ESC lines. Periodic purification by flow sorting every four to five passages allowed us to maintain cultures containing a great majority of haploid ESCs in all cases. Analytic flow profiles of DNA content were recorded after fixation of the cells in ethanol, RNase digestion, and staining with propidium iodide (PI) on a Cyan analyser (Beckman Coulter). For karyotype analysis cells were arrested in metaphase using demecolcine (Sigma). After incubation in hypotonic KCl buffer cells were fixed in methanol-acetic acid (3:1) and chromosome spreads were prepared and stained with DAPI. Immunostaining was performed as described[27] using Nanog (Abcam; 1:100), Oct4 (Santa Cruz; 1:100), Nestin (Developmental Studies Hybridoma bank, Iowa City; 1:30) and Gata4 (Santa Cruz; 1:200) antibodies.

Microarray Analysis

RNA from biological triplicates of diploid ESCs and three independently derived haploid ESCs (HAP-1p21, HAP-2 p24, HTG-1 p11) was extracted using the RNeasy kit (Quiagen). Gene expression analysis on Affymetrix GeneChip 430 2.0 arrays was performed by Imagenes Ges.m.b.H. (Berlin, Germany). Additional gene expression profiles of neural progenitors, mesodermal progenitors and mouse embryonic fibroblasts (MEF) were obtained from a previously published dataset (GEO accession number GSE12982[28]). The data was analysed using Genespring GX software (Agilent Technologies). Data were normalized using the RMA algorithm. Lists showing differentially regulated genes (>2 fold change; $p<0.05$) are provided in FIG. 17. p-values were established by an unpaired t test followed by FDR adjustment by the Benjamini Hochberg method. Hierarchical clustering was performed based on the Euclidean distances and complete linkage analysis. The relatedness of transcription profiles was determined by calculating the Pearson correlation coefficient (r). DNA samples for comparative genomic hybridization (CGH) experiments were extracted and sent to Imagenes Ges.m.b.H. (Berlin, Germany) for CGH analysis using NimbleGen 3×720K mouse whole-genome tiling arrays with an average probe spacing of 3.5 kb. Adult male C57BL/6 kidney DNA was used as a reference. A genomic overview of these analyses is presented in FIG. 5G and FIGS. 10A and 10B at 200 kb resolution and selected zoomed in regions at 40 kb resolution. The complete data set at 40 kb resolution is included in FIG. 11.

Accession of Datasets

Gene expression and CGH data sets can be accessed as the GEO reference series GSE30879 (http://www.ncbi.nlm.nih.gov/geo/query/acc.cgi?acc=GSE30879). This series includes the GSE30744 (Expression analysis of haploid and diploid ES cells in 2i medium) and the GSE30749 (CGH analysis of haploid ES cells) data sets.

Quantitative Gene Expression Analysis

RNA was extracted using the RNeasy kit (Quiagen) and converted into cDNA using the Quantitect reverse transcription kit (Quiagen). Real time PCR was performed on a StepOnePlus machine (Applied Biosystems) using the Fast Sybr green master mix (Applied Biosystems) and previously published primers[27]. The ddCt method was used for quantification of gene expression. Expression levels were normalized to L32 ribosomal protein mRNA and values in diploid control ESCs were set to 1.

Embryo Analysis

Haploid ESCs were co-transfected with a piggyBac vector carrying a CAG-GFP—IRES-hygro transgene and a piggyback transposase expression plasmid. Stable integrants were selected using 150 μg/ml Hygromycin for 7 days. The haploid fraction of HAP-1 (p29), HAP-2 (p18) and HTG-2 (p23) GFP positive cells were purified by flow sorting (FIGS. 13A and 13B). GFP labelled ESCs were expanded and injected into C57BL/6 host blastocysts which were transferred to recipient females. Embryos were analysed at E9.5 and E12.5. Dissociation to single cells was performed by incubation in 0.25% Trypsin/EDTA for 15 min. Prior to PI staining cells were fixed in 4% PFA and permeabilized in PBS/0.25% Triton X-100. Live born chimeras were analysed at postnatal day 2 (P2) for expression of GFP using UV illumination. Images were obtained using a Canon Powershot S5 IS camera with a FHS/EF-3GY2 filter (BLS). All mouse experiments were conducted in accordance with institutional guidelines of the University of Cambridge. All necessary UK home office licenses were in place.

Gene Trap Screen

The screen was performed based on a previously published protocol[25]. $5\times10^6$ HAP-1 ESCs were co-transfected with 2 μg piggyBac transposase plasmid[15] and 1 μg piggyBac gene trap vector (FIG. 15A) using Lipofectamine 2000. piggyBac insertions into expressed genes were selected with 2 μg/ml puromycin for 8 days. $1\times10^7$ ESCs corresponding to approximately 5,000 puromycin resistant colonies were then plated onto two 15 cm dishes. Selection for mismatch deficient integrants was performed using 0.3 μg/ml 6-TG (Sigma). 20 colonies were picked and piggyBac integration sites of seven clones were identified by Splinkerette PCR and mapped using iMapper[29].

References Used Only in the Methods Section

26. Wutz, A. & Jaenisch, R. A shift from reversible to irreversible X inactivation is triggered during ES cell differentiation. *Mol Cell* 5, 695-705 (2000).

27. Leeb, M. et al. Polycomb complexes act redundantly to repress genomic repeats and genes. *Genes Dev* 24, 265-76 (2010).

28. Shen, X. et al. EZH1 mediates methylation on histone H3 lysine 27 and complements EZH2 in maintaining stem cell identity and executing pluripotency. *Mol Cell* 32, 491-502 (2008).

29. Kong, J., Zhu, F., Stalker, J. & Adams, D. J. iMapper: a web application for the automated analysis and mapping of insertional mutagenesis sequence data against Ensembl genomes. *Bioinformatics* 24, 2923-5 (2008).

30. Savarese, F., Flahndorfer, K., Jaenisch, R., Busslinger, M. & Wutz, A. Hematopoietic precursor cells transiently reestablish permissiveness for X inactivation. *Mol Cell Bio*126, 7167-77 (2006).

The invention claimed is:

1. A mammalian haploid embryonic stem cell line, wherein the stem cell line is pluripotent, proliferates, and maintains a haploid karyotype during proliferation in culture for a minimum of 45 days, wherein the cell line is cultured in conditions selected from:

a) a N2B27 chemically defined medium comprising LIF and one or more 2i inhibitor;

b) a N2B27 chemically defined medium comprising 15% KnockOut Serum Replacement supplemented with Glutamin, betamercaptoethanol, penicillin-streptomycin, non-essential amino acids, and 500 units per milliliter recombinant mouse LIF;

c) a N2B27 chemically defined medium comprising 15% fetal calf serum supplemented with Glutamin, betamercaptoethanol, penicillin-streptomycin, non-essential amino acids, and 500 units per milliliter recombinant mouse LIF;

d) high glucose DMEM medium or KnockOut DMEM medium comprising 15% fetal calf serum supplemented with Glutamin, betamercaptoethanol, penicillin-streptomycin, non-essential amino acids and 500 units per milliliter recombinant mouse LIF; or e) high glucose DMEM medium or KnockOut DMEM medium comprising 15% KnockOut Serum Replacement supplemented with Glutamin, betamercaptoethanol, penicillin-streptomycin, non-essential amino acids, and 500 units per milliliter recombinant mouse LIF.

2. The mammalian haploid embryonic stem cell line of claim 1, wherein the proliferation conditions further comprise a fibroblast feeder layer.

3. The mammalian haploid embryonic stem cell line of claim 1, wherein the stem cell is capable of maintaining a haploid karyotype for at least 25 passages.

4. The mammalian haploid embryonic stem cell line of claim 1, wherein the mammalian haploid embryonic stem cell line is derived from *Mus musculus* of a CBA/B6 strain.

5. A cell culture comprising the mammalian haploid embryonic stem cell line of claim 1.

6. The mammalian haploid embryonic stem cell line of claim 1, wherein the mammalian haploid embryonic stem cell line is prepared according to the steps of activating one or more isolated oocytes in vitro to produce a haploid embryo;

culturing the activated haploid embryo to an 8-cell stage, a morula stage, or a blastocyst stage;

removing the zona pellucida from the activated haploid embryo;

isolating the inner cell mass of the activated haploid embryo; and further culturing the inner cell mass to derive the mammalian haploid embryonic stem cell line.

* * * * *